United States Patent
Skak et al.

(10) Patent No.: US 12,070,566 B2
(45) Date of Patent: Aug. 27, 2024

(54) ORAL DELIVERY OF ACTIVE DRUG SUBSTANCES

(71) Applicant: Biograil ApS, Roskilde (DK)

(72) Inventors: Nikolaj Skak, Rungsted Kyst (DK); Karsten Lindhardt, Haslev (DK); Torben Elhauge, Kobenhavn K (DK); Martin Rex Olsen, Farevejle (DK)

(73) Assignee: Biograil ApS, Roskilde (DK)

( * ) Notice: Subject to any disclaimer, the term of this patent is extended or adjusted under 35 U.S.C. 154(b) by 85 days.

(21) Appl. No.: 17/820,750

(22) Filed: Aug. 18, 2022

(65) Prior Publication Data
US 2023/0073256 A1    Mar. 9, 2023

Related U.S. Application Data

(63) Continuation of application No. 16/771,965, filed as application No. PCT/EP2018/085502 on Dec. 18, 2018, now Pat. No. 11,452,851.

(30) Foreign Application Priority Data

Dec. 18, 2017 (DK) .............................. PA 201770955

(51) Int. Cl.
*A61M 31/00* (2006.01)
*A61K 9/00* (2006.01)

(52) U.S. Cl.
CPC ......... *A61M 31/002* (2013.01); *A61K 9/0053* (2013.01)

(58) Field of Classification Search
CPC ........................... A61M 31/002; A61K 9/0053
USPC ........................................ 604/890.1; 424/408
See application file for complete search history.

(56) References Cited

U.S. PATENT DOCUMENTS

| 4,251,506 A | 2/1981 | Laby |
| 4,687,480 A | 8/1987 | Laby et al. |
| 8,157,788 B2 | 4/2012 | Gonzales et al. |
| 11,452,851 B2 | 9/2022 | Skak et al. |
| 2009/0306473 A1 | 12/2009 | Tanaka et al. |
| 2012/0296280 A1 | 11/2012 | Eum |
| 2015/0209180 A1 | 7/2015 | Prausnitz et al. |
| 2015/0342877 A1 | 12/2015 | Menachem et al. |
| 2021/0290918 A1 | 9/2021 | Skak et al. |

FOREIGN PATENT DOCUMENTS

| JP | 2009-291373 A | 12/2009 |
| JP | 2011-245055 A | 12/2011 |
| JP | 2013-517889 A | 5/2013 |
| WO | WO 2013/003824 | 1/2013 |

OTHER PUBLICATIONS

Danish Search Report, Application No. PA 2017 70955, dated Feb. 23, 2018, 3 pages.
International Search Report and Written Opinion, PCT/EP2018/085502, dated Apr. 2, 2019, 12 pages.
Examination Report No. 1 issued on Oct. 12, 2023 in corresponding Australian Patent Application No. 2018387769 Filed Dec. 18, 2017.

*Primary Examiner* — Raymond J Henley, III
(74) *Attorney, Agent, or Firm* — Knobbe, Martens, Olson & Bear, LLP

(57) ABSTRACT

The present disclosure relates to a delivery device capable of delivering compositions. In some embodiments, the delivery device may deliver compositions to the gastrointestinal tract. In some embodiments, the compositions contain active drug substances. In some embodiments, the active drug substances are low permeable active drug substances.

20 Claims, 18 Drawing Sheets

ORAL DELIVERY OF ACTIVE DRUG SUBSTANCES

FIELD

The present disclosure relates to a delivery device capable of delivering compositions. In some embodiments, the delivery device may deliver compositions to the gastrointestinal tract. In some embodiments, the compositions contain active drug substances. In some embodiments, the active drug substances are low permeable active drug substances.

BACKGROUND

A number of for example low permeable active drug substances are currently delivered by i.e. subcutaneous, intradermal, intramuscular or intravenous route. Oral administration has the potential for the widest patient acceptance thus attempts to deliver low permeable active drug substances through the preferred oral route of administration has been tried but with limited success. This is mainly due to two things. Lack of stability and limited absorption from the gastrointestinal tract.

Stability both relates to the stability of the active drug substance during manufacturing and storage of the delivery device, and to the stability of the active drug substance during the passage in the gastrointestinal tract before it become available for absorption.

Limited gastrointestinal absorption is due to the gastrointestinal wall barrier preventing active drug substance from being absorbed after oral dosing because of the low permeability of the active drug substance, which is for example due to pre-systemic metabolism, size and/or the charges and/or because of the water solubility of the active drug substance.

Multiple approaches to solve these stability and absorption challenges have been suggested, but an effective solution to the challenges remain unresolved. Especially, where the delivery device is stable and at the same time facilitate effective absorption from the gastrointestinal tract after oral administration. It will be beneficial to promote delivery devices suitable for such use through the oral route.

U.S. Pat. No. 4,251,506 describes a delivery device for a therapeutic composition (see abstract). The device (capsule) comprises a tubular body which has two resilient arms attached thereto at one end, which arms project outwardly from said body at an angle of approximately 45 degrees (see column 5, lines 57-60; column 7, lines 3-7; FIG. 1). In an embodiment, the body has a length of 9 cm (see column 5, lines 59-62). The capsules are administered orally (see Example 4).

U.S. Pat. No. 4,687,480 describes a delivery device for a therapeutic composition (see abstract). The device (capsule) comprises an elongate, tubular body member and a plurality of elongated wings, each wing being pivotally attached at one end thereof to the body member (see claim 1 and FIG. 1). The angle (A) between the longitudinal extent of the body and the wing is about 70-75 degrees (see column 6, lines 33-37 and FIG. 1). In an embodiment, the capsule has a length of 9 cm (see column 6, line 66-column 7, line 1). The wings are of arcuate form transversely of its longitudinal extent to define a concave surface (see claim 1 and FIG. 2).

Thus, there is an unmet need to provide a novel delivery device, which is capable of delivering stable low permeable active drug substances for absorption in the gastrointernal tissue. More generally, there remains a need for delivery devices and methods that enable enhanced drug delivery, when delivery devices are administered orally to patients.

SUMMARY

A delivery device for a composition is disclosed. The delivery device may have a first end and a second end with a longitudinal axis there between, and may comprise a body and a delivery part, the body may extend along a body axis from a first body end and may have a body surface. The delivery part may comprise one or more attachment parts including a first attachment part, the first attachment part may have a first distal end, e.g. configured to position and/or attach the delivery part in an internal surface of a subject.

Also disclosed is a pharmaceutical composition comprising an excipient and one or more delivery devices as described herein.

In some embodiments, the delivery device may be administered orally.

In some embodiments, the delivery device may provide an improved delivery of for example low permeable active drug substances in particular for oral delivery.

In some embodiments, the delivery device, such as the body and/or attachment part(s), may comprise one or more barb elements. A barb element may assist in keeping the attachment device secured or attached to the internal surface.

In some embodiments, the delivery device may comprise a delivery part constructed to protect a payload. In some embodiments, the delivery device may comprise a delivery part constructed to protect a payload through to the gastrointestinal tract by carrying the payload from the stomach to the intestinal lumen into the intestinal wall.

In some embodiments, the delivery device may be constructed in a way that secures the adapted delivery part to deliver its payload into the internal tissue or internal surface for distribution of the active drug substance in the subject through the blood vessels.

In some embodiments, bowel movements may provide the physical forces generated by the musculature in and around the gastrointestinal tract to facilitate the correct positioning of the delivery device in the gastrointestinal tract and to comprise the physical force needed to position the delivery part into the intestinal wall to release the active drug substance in the gastrointestinal tissue.

In some embodiments, the force applied to the delivery device for example the device body from the peristaltic forces can either be dragging or pushing the delivery part into the gastrointestinal tissue.

In some embodiments, the delivery device utilizes the peristaltic forces posterior to the delivery part to drag the attachment part into the gastrointestinal tissue and/or utilization of peristaltic forces anterior to the delivery part to push the delivery part into the gastrointestinal tissue by utilizes the device body.

In some embodiments, the transport of the active drug substance across the gastrointestinal wall may be localized at the site of attachment in the gastrointestinal tract and consequently this will be the site of release of the active drug substance.

BRIEF DESCRIPTION OF THE FIGURES

The above and other features and advantages of the present disclosure will become readily apparent to those skilled in the art by the following detailed description of exemplary embodiments thereof with reference to the attached drawings, in which.

DETAILED DESCRIPTION

Figure 1:
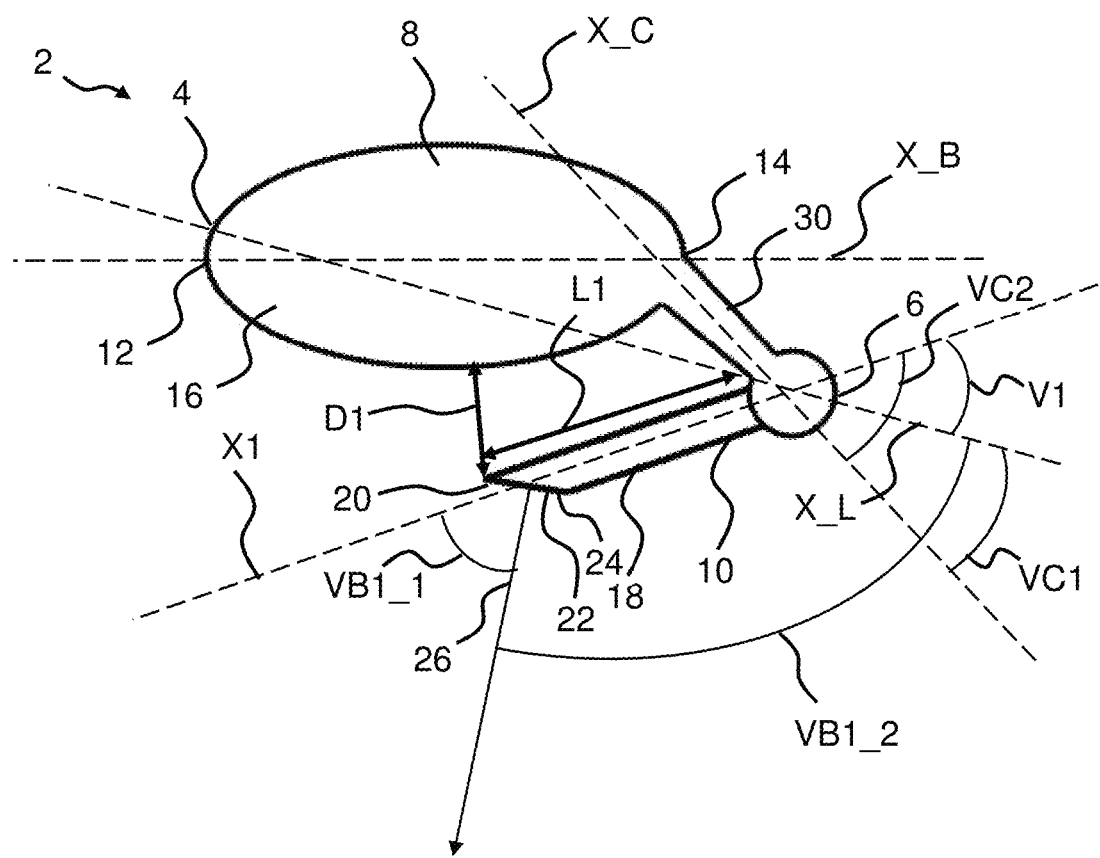
FIG. 1—schematically illustrates an exemplary delivery device

A delivery device used according with the present disclosure may, in theory, be of any shape or design.

The Delivery Device

The present disclosure relates to a delivery device for a composition. The composition may contain an active drug substance.

In some embodiments, the delivery device for a composition, may have a first end and a second end, with a longitudinal axis there between, and may comprise a body and a delivery part, the body may extend along a body axis from a first body end and may have a body surface, the delivery part may comprise a first attachment part, the first attachment part may have a first distal end configured to position the delivery part in an internal tissue of a subject. The first distal end may be arranged at a distance from the body surface. The distance may be at least 0.5 mm.

Internal Tissue/Internal Surface

In some embodiments, internal tissue or internal surface refers to cells, tissue, including mucosal tissues, vascular tissues, lymphatic vessels, gastrointestinal (GI) tissue, vaginal tissue, and cell membranes internal to a subject (for example a human or an animal). In some embodiments, the internal tissue is in an organ selected from the gastrointestinal tract selected for example from the esophagus, stomach, duodenum, small intestine, caecum, large intestine, colon, rectum. In some embodiments, the internal tissue is in the internal gastrointestinal tract.

In some embodiments, the delivery device size and geometry including the body and the delivery part may be designed to fit into a pharmaceutical composition.

In some embodiments, the delivery device size and geometry including the body and the delivery part may be designed to fit into a pharmaceutical composition for oral administration.

Dimension

In some embodiments, the greatest dimension or at least one dimension of the delivery device may be about or less than about 30 mm, about 29 mm, about 28 mm, about 27 mm, about 26 mm, about 25 mm, about 24 mm, about 23 mm, about 22 mm, about 21 mm, about 20 mm, about 19 mm, about 18 mm, about 17 mm, about 16 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm or even about 0.5 mm.

In some embodiments, the greatest dimension or at least one dimension of the delivery device may be more than about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm or about 30 mm.

In some embodiments, the greatest dimension or at least one dimension of the delivery device may be within a range of about 0.5 mm to about 30 mm, about 1 mm to about 30 mm, about 2 mm to about 30 mm, about 3 mm to about 30 mm, about 4 mm to about 30 mm, about 5 mm to about 30 mm, about 6 mm to about 30 mm, about 6 mm to about 29 mm, about 6 mm to about 28 mm, about 6 mm to about 27 mm, about 6 mm to about 26 mm, about 6 mm to about 25 mm, about 6 mm to about 24 mm or about 6 mm to about 23 mm.

In some embodiments, the dimensions of the delivery devices may be represented by a length, a width or a height in X, Y and Z axis where each dimension may be within a range of about 3 mm to about 26 mm in the length, of about 1 mm to about 12 mm in the width and of about 1 mm to about 12 mm in the height.

Material

In some embodiments, the delivery device, the body and/or the delivery part may comprise of for example water soluble, water insoluble, biodegradable, non-biodegradable and/or pH dependent soluble materials.

In some embodiments, water soluble material may allow immediate dissolution or controlled dissolution of the body depending of the material selected. In some embodiments, water insoluble and/or biodegradable material may preserve the body shape throughout the passage though the gastrointestinal tract. In some embodiments, pH dependent soluble material may allow the body to stay intact at pH conditions below the pH at which the material may dissolve for example in the stomach or upper intestinal lumen, but then to dissolve in the upper or lower intestinal lumen after detachment of the delivery part inside the intestinal wall at pH conditions above the pH at which the material dissolves.

In some embodiments, the delivery device may substantially be insoluble in an aqueous medium. In some embodiments, the body may be insoluble to an aqueous medium, such as water. In some embodiments, the delivery part may be insoluble to an aqueous medium, such as water. This ensures that the payload may only be in contact with surrounding aqueous media by one or more openings in the delivery part.

In some embodiments, the delivery device may be biodegradable, disintegrate, crumble or dissolve during the release of the active drug substance. In some embodiments, the delivery part may be biodegradable, disintegrate, crumble or dissolve during the release of the active drug substance. In some embodiments, the body may be biodegradable, disintegrate, crumble or dissolve during the release of the active drug substance.

In some embodiments, the delivery device may be applied for delivery the active drug substance and may remain intact if it is supported by the payload containing the active drug substance. In some embodiments, the delivery device may lack the ability to remain intact after the payload has delivered the active drug substance. In some embodiments, the delivery device may not remain in the subject for any significant amount of time after completed the delivery of the active drug substance.

In some embodiments, the delivery device i.e. body and the delivery part may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators.

Further details of the materials used is also described below in the General production materials section.

The Body

In some embodiments, the delivery device may be made of a material comprising one or more thermoplastic polymers. In some embodiments, the delivery device may be reinforced by fibers or similar.

In some embodiments, the delivery device may comprise a body. In some embodiments, the body may be made of a material comprising one or more thermoplastic polymers. In some embodiments, the body may have a shape and size assisting in positioning the delivery part (attachment part(s)) in a suitable angle and position to ensure that the distal end(s) of the attachment part(s) to position in the internal surface of the subject, such that the delivery part may be attached to the internal surface for example for delivery of an active drug substance through the internal surface. In other words, the body may be constructed such that secure attachment of attachment part(s) to the internal surface, for example tissue of the gastrointestinal wall, may be provided, thus allowing the delivery device to deliver payload or an active drug substance in the internal tissue.

Dome-Shaped Body

Figure 20:
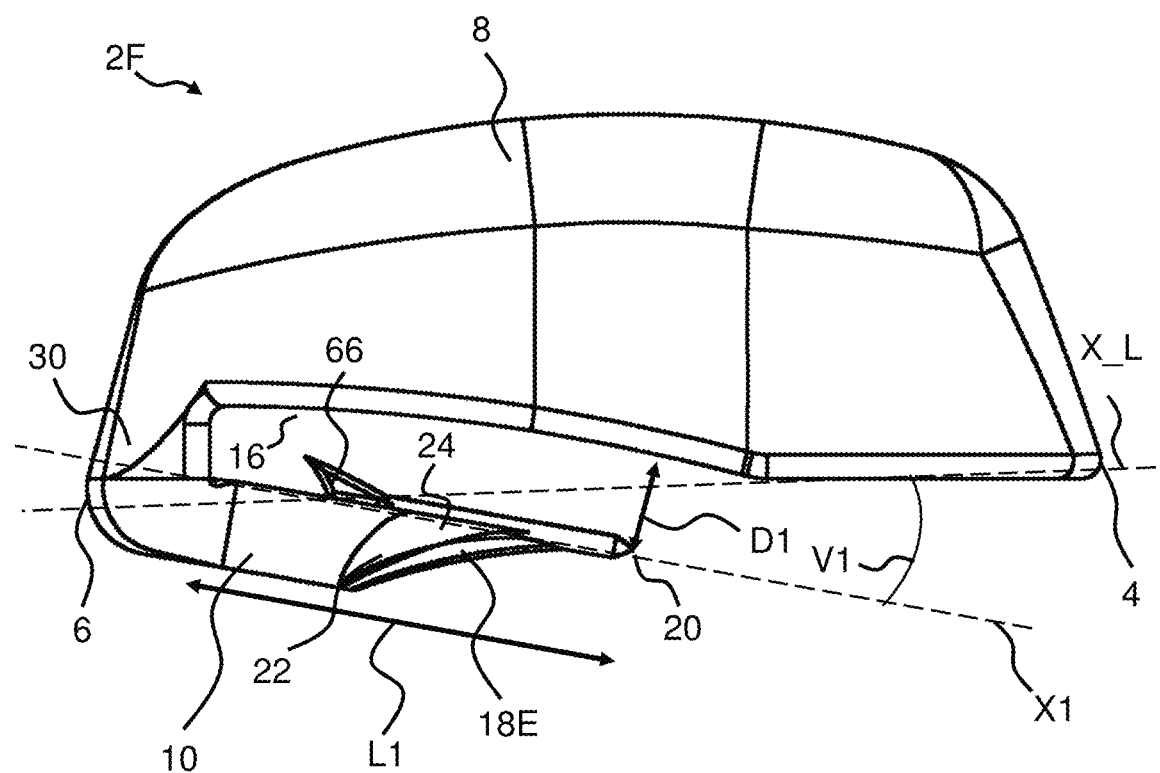
FIG. 20—is a view of an exemplary delivery device

The body may have a dome shaped or curved outer surface part facing away from the first attachment part and optionally a substantially planar surface part facing the first attachment part e.g. as illustrated in FIG. 20.

Droplet Shape

In some embodiments, the body may have droplet shape with a wide end towards the first body end. Thus, the body may have a decreasing cross-sectional extension (largest extension perpendicular to the body axis) from a first point at a first body distance from the first body end. The body may have a first cross-sectional extension at the first point in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm, for example with the first body distance being in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm.

In some embodiments, the body may have a maximum cross-sectional extension along the body axis in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm.

Figure 5:
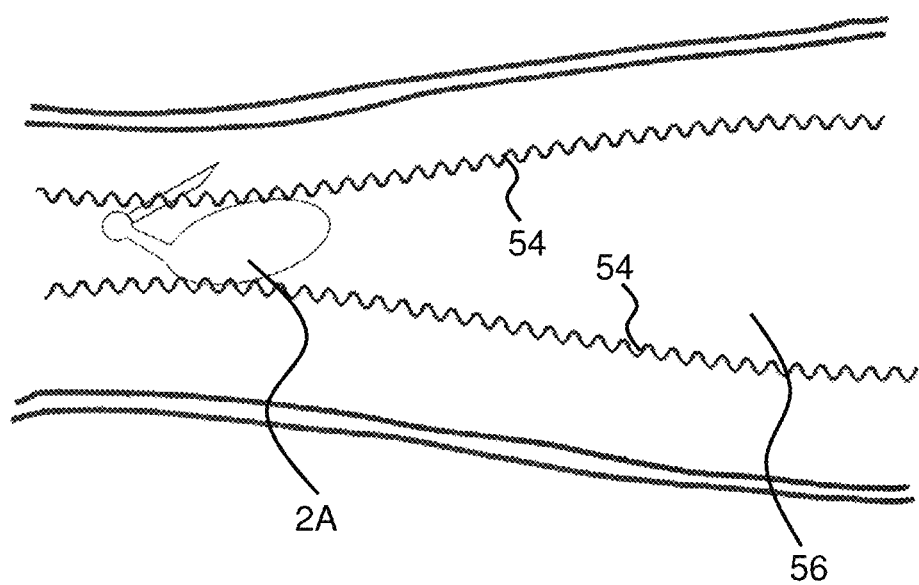

In some embodiments, the body of the delivery device may be constructed to secure the delivery part to deliver the payload into the gastrointestinal tissue of a subject. In some embodiments, the body size and shape of the delivery device may be designed in a way that bowel movements impact the position of the body, so that the body may be aligned in the gastrointestinal tract at the time of position the delivery part in the gastrointestinal wall and positions inside the gastrointestinal wall in a safe and reproducible manner. In some embodiments, the body size and shape of the delivery device may also be designed in a way that the forces from bowel movements has an impact on the body that secures appropriate directed force is put into the delivery part for it to position itself in the gastrointestinal wall, as illustrated in FIG. 5, which shows the delivery device in a gastrointestinal lumen.

Other Shapes

In some embodiments, various body designs of the delivery device may achieve a reproducible release of the payload from the delivery part in the gastrointestinal tissue.

In some embodiments, the body may for example be round, squared, triangular, cylindric, oval or curved shape. In some embodiments, the body may be flat for example like a patch. In some embodiments, the body may have attached hook(s) and/or barb(s) on the flat surface or in the perimeter of the edges for efficient anchor to the gastrointestinal wall, to secure alignment and optimal forces to be directed into the delivery part for it to position itself in the gastrointestinal wall.

Barb

In some embodiments, the body may contain a delivery part with barb to secure the same position of the body at the site of position the delivery part in the gastrointestinal wall for the time required for the delivery part to detach or for the payload from the delivery part to be released in the gastrointestinal tissue or for the payload from the body to be delivered through the delivery part.

In some embodiments, the body may contain one or more barbs.

Enhancer

In some embodiments, the body and/or the delivery part may contain one or more enhancers.

Adhesive Material

In some embodiments, the body and/or the delivery part may contain one or more adhesive materials.

Electrical Element

In some embodiments, the body may contain an electrical element. In such embodiment, the electrical element may provide electro-radiation (i.e. UV radiation) or electroporation abilities that enhances the absorption of the active drug substance.

Connection Part

In some embodiments, the delivery device may comprise a connection part arranged between the body and the delivery part. The connection part may extend along a connection axis. The connection axis may form a first connection angle with the longitudinal axis. The first connection angle may be in the range from 30 degrees to 60 degrees.

In some embodiments, the connection axis may form a second connection angle with the first axis. The second connection angle may be larger than 45 degrees, such as larger than 60 degrees.

In some embodiments, the connection part may be strengthened, for example by thickening the connection part, to secure prolonged attachment of the delivery part to the body after the delivery part is positioned in the inner gastrointestinal wall.

In some embodiments, the connection part and the first distal end of the delivery part may control the depth of which the delivery part position itself in the inner gastrointestinal wall.

In some embodiments, the length of the connection part may control the depth of which the delivery part is positioned in the inner gastrointestinal wall.

The Delivery Part

The delivery device may comprise a delivery part. The delivery part may be configured to deliver a composition or a substance, such as an active drug substance, in an internal surface of the subject.

Shape

In some embodiments, the delivery part may refer to a protruding shape from the delivery device.

In some embodiments, the shape of the delivery part may be designed to secure reproducible penetration of the delivery part from the internal lumen into the internal tissue for example the inner gastrointestinal lumen into the gastrointestinal wall, without penetrating the outer internal tissue for example the outer gastrointestinal wall. In some embodiments, the shape of the delivery part may be designed to reproducibly attach to the internal tissue for example the gastrointestinal wall and once attached for example remain attached, detach or break from the body in such a way that the delivery part may remain inside the internal tissue for example gastrointestinal tissue until the payload may be released. In some embodiments, the shape of the delivery part may be designed to secure minimal physical impact on the internal tissue for example the inner gastrointestinal wall in such a way that the delivery device may safe to administrate for the subject.

In some embodiments, the delivery device may be arranged and constructed so that two or more delivery parts may protrude in different directions in the three-dimensional space. In some embodiments, the delivery part may protrude from the delivery device at an angle below 90 degrees.

In some embodiments, the delivery part may protrude at angle from a body surface, the delivery part may have a base-integrally connected to the surface of the body.

In some embodiments, the shape of the delivery part may be bended/curved and/or rounded in such a way that it may be able to position itself in the internal tissue for example the gastrointestinal wall.

In some embodiments, the delivery part may protrude from the delivery device at an angle below 90 degrees to allow the delivery part to be longer than the thickness of the internal tissue for example the gastrointestinal wall.

Material

The delivery part may be made of a material comprising one or more thermoplastic polymers. The material of the delivery part may comprise one or more active drug substances. Thus, an active drug substance may be embedded in the material of the delivery part.

In some embodiments, the delivery part may comprise for example water soluble, water insoluble, biodegradable, non-biodegradable and/or pH dependent soluble materials.

In some embodiments, the delivery part may comprise a water soluble, biodegradable and/or pH-dependent material that may dissolve and/or degrade so that the delivery part lodged in the intestinal tissue may gradually degrade and/or dissolve.

In some embodiments, the delivery part may comprise a water-soluble material to allow immediate release or modified release of the payload depending of the material selected. In some embodiments, a water insoluble or biodegradable material may allow depot of the payload in the delivery part for longer release duration (for example days, weeks or months). In some embodiments, a pH dependent soluble material may allow the delivery part to stay intact at pH conditions below the physiologic for example a pH of approximately 7.4 to remain intact in the gastrointestinal lumen, but then may dissolve once inside the gastrointestinal wall. In some embodiments, one or more water soluble, water insoluble, biodegradable and/or pH dependent materials may optionally be combined to control release of the active drug substance for example by diffusion or erosion of the delivery part for controlled release duration (for example minutes, hours, days, weeks, or months).

In some embodiments, the delivery part may be made from different compositions such as for example an outer part of the delivery part may be made of one composition and an inner core of the delivery part may be made from another composition. In some embodiments, the outer part and the inner core of the delivery part may be composed of for example a water soluble, a water insoluble, a biodegradable, and/or a pH dependent material. In some embodiments, one or more water soluble, water insoluble, biodegradable and/or pH dependent materials may be combined to control the release of the active drug substance from the payload once the delivery part may move its position from the lumen to the internal tissue for example the gastrointestinal lumen to the gastrointestinal tissue.

Further details of the materials used is also described below in the General production materials section.

Hooking Zone

In some embodiments, the first attachment part comprises a first distal end (hooking zone) and a cutting zone. In some embodiments, the first distal end (hooking zone) of the delivery part may be sharp enough to ensure the delivery part hooks easily into the internal tissue for example the gastrointestinal wall, the first distal end may have an angel or curvature, so the delivery part facilitate this. Cutting zone of the delivery part may have a pointy sharpness, cutting edge and/or sharp edges to cut the tissue without rupture, and the steady zone of the delivery part may contain payload and/or a separation part.

In some embodiments, the dimensions of the delivery part may be designed for the particular way in which it may be used. Without wishing to be bound by any particular theory, parameters such as the length of the delivery part such as the distance between the delivery device surface where the delivery part protrudes from to the first distal end of the delivery part, and the shape/size of the delivery part (for example, gauge size/width, first distal end shape, etc.) may influence the interaction of the delivery part, and thus the efficiency of delivery of a payload.

In some embodiments, the sharpness of the delivery part may be balanced in such a way that it may have the ability or properties to position itself in the internal tissue for example into the gastrointestinal wall. In some embodiments, the delivery part may include a first distal end.

Gauge

In some embodiments, the gauge (for example the largest cross section) of the delivery part may be about or less than about 10 mm, about 9 mm, about 8 mm, about 7 mm, about 6 mm, about 5 mm, about 4 mm, about 3 mm, about 2 mm, about 1 mm or even about 0.5 mm.

In some embodiments, the gauge (for example the largest cross section) of the delivery part may be more than about 0.5 mm, about 1 mm, about 2 mm, about 3 mm, about 4 mm, about 5 mm, about 6 mm, about 7 mm, about 8 mm, about 9 mm or even about 10 mm.

In some embodiments, gauge (for example the largest cross section) of the delivery part may be within a range of about 0.5 mm to about 10 mm, about 0.5 mm to about 9 mm, about 0.5 mm to about 8 mm, about 0.5 mm to about 7 mm, about 0.5 mm to about 6 mm, about 0.5 mm to about 5 mm, about 0.5 mm to about 4 mm, about 0.5 mm to about 3 mm, about 1 mm to about 3 mm.

Barb

In some embodiments, the delivery part may contain one or more protruding barbs to secure the same position of the delivery part and/or fix the delivery part in the internal tissue for the time required for the payload to be released in the internal tissue.

Tubular

In some embodiments, the delivery part may be tubular and may include a tubular body and the tubular body may comprise a payload for example a liquid payload connected to a tubular delivery part so the payload may flow though the delivery part into the internal tissue for example the intestinal tissue. In some embodiments, the tubular body may contain expandable excipients that may expand by a chemical reaction for example when mixed expand in volume and/or produce a gas to advance the delivery of the payload. In some embodiments, the expansion is by osmosis.

Enhancers or Adhesive Materials

In some embodiments, the delivery part may contain one or more enhancers and/or one or more adhesive materials to disrupt the internal tissue for example the inner gastrointestinal wall and release the active drug substance in the periphery of the internal tissue for example the inner gastrointestinal wall to provide access to the blood vessels in the internal tissue for example the gastrointestinal tissue.

Length of the Delivery Part

In some embodiments, the length of the delivery part may be about or less than about 30 mm, about 29 mm, about 28 mm, about 27 mm, about 26 mm, about 25 mm, about 24 mm, about 23 mm, about 22 mm, about 21 mm, about 20 mm, about 19 mm, about 18 mm, about 17 mm, about 16 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm or even about 0.5 mm.

In some embodiments, the length of the delivery part may be more than about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm or even about 30 mm.

In some embodiments, the length of the delivery part may be within a range of about 0.5 mm to about 30 mm, about 1 mm to about 30 mm, about 1 mm to about 29 mm, about 1 mm to about 28 mm, about 1 mm to about 27 mm, about 1 mm to about 26 mm, about 1 mm to about 25 mm, about 1 mm to about 24 mm, about 1 mm to about 23 mm, about 1 mm to about 22 mm, about 1 mm to about 21 mm, about 1 mm to about 20 mm, about 1 mm to about 19 mm, about 1 mm to about 18 mm, about 1 mm to about 17 mm, about 1 mm to about 16 mm, about 1 mm to about 15 mm, about 1 mm to about 14 mm, about 1 mm to about 13 mm, about 1 mm to about 12 mm, about 1 mm to about 11 mm, about 1 mm to about 10 mm, about 0.5 mm to about 10.

In some embodiments, the delivery device may comprise a single attachment part. In some embodiments, the delivery device may comprise a plurality of attachment part and may include two or more attachment parts. In some embodiments, the delivery device may comprise a first attachment part. In some embodiments, the delivery device may comprise a first attachment part and a second attachment part. In some embodiments, the delivery device may comprise a first attachment part, a second attachment part and a third attachment part etc.

First Attachment Part

In some embodiments, the first attachment part may extend along a first axis. A first angle between the first axis and the longitudinal axis may be less than 75 degrees, such as in the range from 2 degrees to 60 degrees. In one or more exemplary delivery devices, the first angle is in the range from 5 degrees to 45 degrees. The first angle may be less than 20 degrees.

In some embodiments, the first attachment part may extend along a first axis, wherein a first angle between the first axis and the body axis is less than 75 degrees.

In some embodiments, the first attachment part may be needle-shaped, conical, cylindrical, tubular pyramid-shaped, star-shaped, spatula-shaped, bevel-shaped, taper point-shaped or a hook-shaped. In some embodiments, the delivery part may be straight, curved or semi hook-shaped. In some embodiments, the first attachment part may take the form of a spike.

In some embodiments, the first attachment part may define a first cavity for accommodating an active drug substance. In one or more exemplary delivery devices, the first attachment part defines a first cavity for accommodating a payload comprising an active drug substance.

In some embodiments, the delivery part comprising a first attachment part, the first attachment part may have a first distal end configured to position the delivery part in an internal tissue of a subject.

In one embodiment, the first attachment part may have a first distal end configured to position itself in an internal surface of the subject. The internal surface may be a gastrointestinal surface.

In some embodiments, the first attachment part may have a length in the range from 1.0 mm to 20 mm, such as in the range from 2.0 mm to 10 mm. In one or more exemplary delivery devices, the first attachment part has a length in the range from 4.0 mm to 6.0 mm, or example about 5 mm.

In some embodiments, the first distal end may be arranged at a distance from the body surface, wherein the distance optionally is at least 0.5 mm. The distance between the first distal end and the body surface may be at least 0.8 mm, such as in the range from 0.9 mm to 20 mm. In one or more exemplary delivery devices, the distance between the first distal end and the body surface is in the range from 1.0 mm to 5.0 mm, for example about 1.5 mm.

In some embodiments, the first distal end of the first attachment part may be arranged between the first body end and a second body end of the body.

In some embodiments, the first attachment part may have a first distal end configured to position itself in an internal surface of a subject, the first distal end may be arranged at a distance from the body surface, wherein the distance is at least 0.5 mm.

First Bend

In some embodiments, the first attachment part may comprise a first bend near or within 2.0 mm from the first distal end. The first distal end may point in a first direction forming a first primary bend angle with the longitudinal axis. The first primary bend angle may be less than 75 degrees, such as in the range from 0 degrees to 60 degrees. In one or more exemplary delivery devices, the first primary bend angle is in the range from 1 degree to 30 degrees. The first direction may form a first secondary bend angle with the first axis. The first secondary bend angle may be less than 75 degrees, such as in the range from 1 degree to 60 degrees. In one or more exemplary delivery devices, the first primary bend angle is in the range from 5 degrees to 30 degrees.

First Bevel

In some embodiments, the first attachment part may comprise a first bevel surface forming a cutting edge, for example extending from or within a distance in the range from 0.5 mm to 2 mm from the first distal end. The cutting edge formed by the first bevel surface may be at or near, such as within 2.0 mm from, the first distal end. The first bevel surface may be a plane surface. The first bevel surface may be concave. The first bevel surface may have a first bevel normal. The first bevel normal may form a first primary bevel angle with the first axis. The first primary bevel angle may be larger 20 degrees. The first primary bevel angle may be in the range from 30 degrees to 60 degrees. The first bevel normal may form a first secondary angle with the longitudinal axis. The first secondary angle may be larger 45 degrees. In one or more exemplary first attachment parts, the first secondary angle may be less than 45 degrees.

In some embodiments, the first bevel surface may be concave. In some embodiments, the first attachment part may comprise a first bevel surface forming a cutting edge extending from the first distal end. In some embodiments, the first bevel surface may have a first bevel normal, the first bevel normal forming a first primary bevel angle with the first axis larger 20 degrees. In some embodiments, the first bevel normal forming a first secondary angle with the body axis larger 45 degrees.

Second Bevel

In some embodiments, the first attachment part may comprise a second bevel surface forming a cutting edge at or near, such as within 2.0 mm from, the first distal end. In some embodiments, the second bevel surface may be concave.

In some embodiments, the second bevel surface forms a cutting edge, for example extending from or within a distance in the range from 0.5 mm to 2.0 mm from the first distal end. The cutting edge formed by the second bevel surface may be at or near, such as within 2.0 mm from, the first distal end. The second bevel surface may be a plane surface. The second bevel surface may be concave.

"Star" Shape

The first attachment part may have a star-shaped cross-section with three, four or more cutting edges formed by recesses or cut-outs in the first attachment part.

Piercing

In some embodiments, the attachment part was designed with focus on utilizing the efficient piercing, with a sharp attachment and further to improve the subsequent cutting following the initial piercing of the internal tissue, to facilitate efficient and full penetration of the delivery part into the internal tissue.

In some embodiments, the initial piercing was made efficient by reducing the attachment part tip angle making the attachment part point sharper, and the length of the narrow part of the attachment part was extended as much reasonable to secure efficient piercing even when piercing elastic internal tissue.

In some embodiments, the cutting was facilitated by adding one or more sharp edges expanding from the point of piercing closer to or even beyond the width of the attachment part to facilitate cutting an opening for easy penetration of the delivery part when constrictive and propulsive peristaltic forces are applied to the delivery part.

Point Sharpness of the First Distal End

In some embodiments, the point sharpness of the delivery part may be defined as the force a delivery part first distal end may use to penetrate a well-defined film. In the present context, the point sharpness of the delivery part relates to the first distal end of the first attachment part.

The force may be compared with the force used by a hypodermic needle to penetrate the same film. In some embodiments, hypodermic needles such as, a 25 G, 18 G and 18 G blunt needle have been used as reference, as a 18 G blunt needle may be difficult to insert in the internal tissue for example intestinal wall and the normal 25 G and 18 G needle may be relatively easy to insert in the internal tissue for example intestinal wall.

In some embodiments, the point sharpness of the delivery part may be the first local maximum of the time/force curve which relates to the penetration of the first distal end through the film and the point sharpness of delivery part is measured in gram. The values may only be used relative to the reference needles values. In some embodiments, the point sharpness of the delivery part may be better than a 18 G blunt needle. In some embodiments, the point sharpness of the delivery part may at least be in the same range as a 25 G and a 18 G needle or less than a 25 G and a 18 G needle.

Second Attachment Part

In some embodiments, the delivery part may comprise a second attachment part, the second attachment part may have a second distal end configured to position itself in an internal surface of a subject. The second attachment part may extend along a second axis. A second angle between the second axis and the longitudinal axis may be less than 75 degrees, such as in the range from 2 degrees to 60 degrees. In one or more exemplary delivery devices, the second angle is in the range from 5 degrees to 45 degrees.

In some embodiments, the second attachment part, may have a second distal end configured to position itself in an internal surface of the subject. The internal surface may be a gastrointestinal surface.

In some embodiments, the second attachment part may have a length in the range from 1.0 mm to 20 mm, such as in the range from 2.0 mm to 10 mm. In one or more exemplary delivery devices, the second attachment part has a length in the range from 4.0 mm to 6.0 mm, for example about 5 mm.

In some embodiments, the second distal end may be arranged at a distance from the body surface, wherein the distance is at least 0.5 mm. The distance between the second distal end and the body surface may be at least 0.8 mm, such as in the range from 0.9 mm to 20 mm. In one or more exemplary delivery devices, the distance between the second distal end and the body surface is in the range from 1.0 mm to 5.0 mm, for example about 1.5 mm.

Cavities

In some embodiments, the delivery part or a portion of the delivery part may be solid or hollow. In some embodiments, the delivery part or a part of the delivery part may be porous or non-porous. In some embodiments, the delivery part or a part of the delivery part may be degradable or non-degradable.

In some embodiments, the delivery device may comprise or define one or more cavities for accommodating a separation part. The separation part may break upon attachment of the delivery part in the internal surface for separating the body and the delivery part.

In some embodiments, the delivery device may comprise a payload with the active drug substance. The payload may be accommodated in a cavity of the delivery device. The payload may be divided into a plurality of payloads accommodated in a plurality of cavities. In some embodiments, the payload may be included in a first cavity and a second cavity of the delivery device.

In some embodiments, the delivery device may comprise or define one or more cavities for accommodating a payload. The payload may comprise an active drug substance.

In some embodiments, the first attachment part defines a first cavity for accommodating a payload comprising an active drug substance. In some embodiments, the second attachment part defines a second cavity for accommodating a payload comprising an active drug substance.

Separation Part

In some embodiments, the delivery device may comprise a separation part arranged between the body and the delivery part. The separation part may optionally be configured to break upon attachment of the delivery part in the internal surface for separating the body and the delivery part upon attachment of the delivery part.

In some embodiments, the separation part may comprise a water soluble, biodegradable and/or pH-dependent material that dissolves and/or degrades so that the delivery part is released from the body from which it protrudes and may remain lodged in the internal tissue.

In some embodiments, the separation part may contain hydrophilic plasticizers leaching out of a cavity or cavities, resulting in decreased mechanical resistance and allowing detachment or cracking, or resulting in pore formation for faster dissolution of the separation part.

In some embodiments, the separation part may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators.

Payload

In some embodiments, the delivery part may be dimensioned and constructed to comprise or carry one or more payloads, such as medical payloads.

In some embodiments, the outer part of the delivery part may be without a payload. In some embodiments, the outer part of the delivery part may contain a payload. In some embodiments, the inner core of the delivery part may be without a payload. In some embodiments, the inner core of the delivery part may contain a payload.

In some embodiments, the payload may be contained in one or more cavities. The payload may comprise an active drug substance.

In some embodiments, the payload may be in different concentrations with one or more type of materials. In some embodiments, the payload may be in different concentrations with the same or other type of materials to differentiate the release of the active drug substance from each payload. In some embodiments, the outer part of the delivery part may act as a physical barrier to shield the payload in the inner core of the delivery part from the lumen for example the gastrointestinal lumen until the delivery part may be positioned in the internal tissue for example gastrointestinal tissue.

In some embodiments, the delivery part volume may be designed to contain a payload composition with an active drug substance to obtain a biologic or medical response.

In some embodiments, the delivery part may be dimensioned and constructed to comprise or carry one payload and in some embodiments more than one payload. In some embodiments, the delivery part may be hollow or porous constructed to carry a payload in small cavities. In some embodiments, the delivery part may contain a hollow and a channel that enables storage of a payload in one or more cavities in the device body.

In some embodiments, the payload may comprise pharmaceutical composition, medical composition or an active drug substance to be delivered into the internal tissue to release for example the active drug substance in the internal tissue for distribution of the active drug substance to the blood vessels in the tissue. The active drug substance may then be distributed by the blood vessels in the subject. In some embodiments, a payload may include a bioactive agent.

In some embodiments, the payload may comprise excipients with specific properties such as for example osmotic, wicking, hygroscopic, effervescent, swelling and/or disintegration properties.

In some embodiments, the payload may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators.

In some embodiments, the payload may be in a solid, a semisolid or a liquid form or a combination thereof.

In some embodiments, a payload may be in a gas form, a liquid form, a solid form or combinations thereof.

In some embodiments, the volume of a payload may be about or less than about 200 µl, about 175 µl, about 150 µl, about 125 µl, about 100 µl, about 75 µl, about 50 µl, about 25 µl, about 20 µl, about 15 µl, about 10 µl, about 9 µl, about 8 µl, about 7 µl, about 6 µl, about 5 µl, about 4.5 µl, about 4 µl, about 3.5 µl, about 3 µl about 2.5 µl, about 2 µl, about 1.5 µl, about 1 µl, about 0.9 µl, about 0.8 µl, about 0.7 µl, about 0.6 µl, about 0.5 µl, about 0.4 µl, about 0.3 µl, about 0.2 µl, about 0.1 µl, about 0.05 µl or even about 0.01 µl.

In some embodiments, the volume of a payload may be more than about 0.01 µl, about 0.05 µl, about 0.1 µl, about 0.2 µl, about 0.3 µl, about 0.4 µl, about 0.5 µl, about 0.6 µl, about 0.7 µl, about 0.8 µl, about 0.9 µl, about 1 µl, about 1.5 µl, about 2 µl, about 2.5 µl, about 3 µl, about 3.5 µl, about 4 µl, about 4.5 µl, about 5 µl about 6 µl, about 7 µl, about 8 µl, about 9 µl, about 10 µl, about 15 µl, about 20 µl, about 25 µl, about 50 µl, about 75 µl, about 100 µl, about 125 µl, about 150 µl, about 175 µl or even about 200 µl.

In some embodiments, the volume of the payload may be in a range of about 0.01 µl to about 200 µl, 0.01 µl to about 175 µl, 0.01 µl to about 150 µl, 0.01 µl to about 125 µl, 0.01 µl to about 100 µl, 0.01 µl to about 75 µl, 0.01 µl to about 50 µl, 0.01 µl to about 25 µl, 0.01 µl to about 20 µl, 0.01 µl to about 15 µl, 0.01 µl to about 10 µl, 0.01 µl to about 9 µl, 0.01 µl to about 8 µl, 0.01 µl to about 7 µl, 0.01 µl to about 6 µl, 0.01 µl to about 5 µl, 0.05 µl to about 5 µl, 0.1 µl to about 5 µl, 0.2 µl to about 5 µl.

In some embodiments, a payload may be transported from the body though the delivery part and the volume of a payload may then be about or less than about 1000 µl, about 900 µl, about 800 µl, about 700 µl, about 600 µl, about 500 µl, about 400 µl, about 300 µl, about 200 µl, about 100 µl, about 90 µl, about 80 µl, about 70 µl, about 60 µl, about 50 µl, about 40 µl, about 30 µl, about 20 µl, about 10 µl, about 7.5 µl about 5 µl, about 2.5 µl, about 2 µl, about 1.5 µl, about 1 µl or even about 0.5 µl.

In some embodiments, a payload may be transported from the body though the delivery part and the volume of a payload may then be more than about 0.5 µl, about 1 µl, about 1.5 µl, about 2 µl, about 2.5 µl, about 5 µl, about 7.5 µl, about 10 µl, about 20 µl, about 30 µl, about 40 µl, about 50 µl, about 60 µl, about 70 µl, about 80 µl, about 90 µl, about 100 µl, about 200 µl, about 300 µl, about 400 µl, about 500 µl, about 600 µl, about 700 µl, about 800 µl, about 900 µl or even about 1000 µl.

In some embodiments, a payload may be transported from the body though the delivery part and the volume of a payload may then be in a range of about 0.5 µl to about 1000 µl, 0.5 µl to about 900 µl, 0.5 µl to about 800 µl, 0.5 µl to about 700 µl, 0.5 µl to about 600 µl, 0.5 µl to about 500 µl, 1 µl to about 500 µl, 1.5 µl to about 500 µl, 2 µl to about 500 µl.

In some embodiments, the degradation rate/dissolution rate of delivery device for example the delivery part may dictate the mechanism and efficiency of delivery of the payload.

In some embodiments, the delivery part may be constructed to carry a payload, a payload to be delivered in to an internal tissue of a subject. The payload may comprise one active drug substance or a combination of more than one different active drug substances, and optionally mixed with one or more pharmaceutically acceptable excipients.

Pharmaceutical Composition

In some embodiments, the delivery device may be contained in a pharmaceutical composition. In some embodiments, the pharmaceutical composition may comprise a delivery device.

In some embodiments, the pharmaceutical composition comprising an active drug substance.

In some embodiments, the pharmaceutical composition may provide delivery of low permeable active drug substances.

In some embodiments, the delivery device may contain in a pharmaceutical composition. Such composition may comprise one or more delivery devices and each delivery device may comprise a delivery part containing a payload. In some embodiments, the payload may contain an active drug substance.

In some embodiments, the pharmaceutical composition may comprise a delivery device. In some embodiments, the pharmaceutical composition may comprise a delivery device comprised of thermoplastic materials, which is stable and may facilitate efficient absorption and access to the blood stream in the internal tissue. In some embodiments, the pharmaceutical composition may comprise a delivery device comprised of thermoplastic materials, which may be stable and may facilitate efficient absorption and access to the blood stream in the gastrointestinal tissue after oral administration.

In some embodiments, the delivery device may be contained in a pharmaceutical composition for example in a capsule, a tablet or any other swallowable compositions to allow delivery of the delivery device at any site of the gastrointestinal tract to release the payload in the internal tissue and such payload may contain an active drug substance.

In some embodiments, the delivery device may be contained in a pharmaceutical composition for example in a suppository to allow delivery of the delivery device and to release the payload in the internal surface and such payload may contain an active drug substance.

In some embodiments, pharmaceutical composition may refer to capsules or tablets possible to swallow by most patients. Typically, a 000 capsule is the maximum size to swallow and the pharmaceutical composition may be aimed to be less than 10 mm at the smallest dimension and less than 26 mm at the largest dimension. In some embodiments, pharmaceutical composition may be round and the dimension may be aimed to be less than 15 mm in the smallest dimension.

In some embodiments, the delivery device may be contained in for example a capsule composed with a pH dependent or a pH independent composition or optionally with a pH dependent or pH independent coat.

In some embodiments, the delivery device may be contained in for example a tablet composed with a pH dependent or pH independent coat.

In some embodiments, the delivery device may be contained with adhesive materials in the pharmaceutical composition to bring the delivery device close to internal tissue facilitating the interaction of the delivery part and the internal tissue.

In some embodiments, the pharmaceutical composition is prepared for delivery the delivery device in combination with adhesive materials.

In some embodiments, the delivery device may be contained with enhancers in the pharmaceutical composition to improve the delivery of the active drug substance in the internal tissue.

In some embodiments, the pharmaceutical composition is prepared for delivery the delivery device in combination with enhancers.

In some embodiments, the delivery device may be contained with one or more laxantia active drug substances in the pharmaceutical composition to improve peristaltic movements and potentially improve or speed up the correct positioning of the delivery device and the delivery part in the gastrointestinal wall. In some embodiments, laxantia active drug substances may be selected from for example betanechol, metoclopramide, cisapride, methylnaltrexone, naloxagol, loperamide, diphenoxylate with and without atropine, diphenoxine with and without atropine and/or magnesium products etc.

In some embodiments, the pharmaceutical composition for oral administration may be administered in combination with food for example prunes and/or seeds etc. to improve peristaltic movements and potentially improve or speed up the correct positioning of the delivery device and the delivery part in the gastrointestinal wall.

Coating

In some embodiments, the capsule, the tablet or any other swallowable compositions may contain optionally a coat. In some embodiments, the coat may comprise a pH-dependent composition to target delivery of the delivery device at any site of the gastrointestinal tract to release the payload in the internal tissue. In some embodiments, the coat may comprise a controlled pH-independent composition to target delivery of the delivery device at any site of the gastrointestinal tract to release the payload in the internal tissue.

In some embodiments, the delivery device, body and/or delivery part may contain optionally a coat. In some embodiments, the coat may be silicone. In some embodiments, the silicone coat lowers the resistance of the delivery part to penetrate the internal surface.

Silicone oil is any liquid polymerized siloxane with organic side chains. The most important member is polydimethylsiloxane. These polymers are of commercial interest because of their relatively high thermal stability and their lubricating properties.

In some embodiments, the silicone coat may include silicone selected from the group consisting of polydimethylsiloxane, Dimethicone in different viscosities from 20 cst to 30,000 cst, for example Dimethicone 20 cst, Dimethicone 100 cst, Dimethicone 350 cst, Dimethicone 1000 cst and/or Dimethicone 12500 cst.

In some embodiments, the silicone coat may include silicone selected from the group consisting of dimethoxysilyldimethyl aminoethyl aminopropyl silicone, polydimethylsiloxane, dimethyl siloxane, trimethyl siloxane, cyclosiloxanes and/or siloxanes for example hexamethyldisiloxane.

Cosmetic Coat

In some embodiments, the capsule, the tablet or any other swallowable compositions may also contain a cosmetic coat that fully covers the pharmaceutical composition. Said cosmetic coat may be selected from the group consisting of taste-masking coats, coats with aqueous moisture barriers and/or oxidative barriers to improve the stability of the composition, and coat containing coloring agents, sweetening agents and/or flavoring agents in order to provide an elegant and palatable pharmaceutical composition and/or to easy distinguishable dose strengths.

In some embodiments, it may be particularly useful to coat compositions having different dose strengths or active drug substances with cosmetic coats of different colors so that the different actives and dose strengths may be easily distinguished. In some embodiments, the cosmetic coat may contain an active drug substance.

In some embodiments, the cosmetic coat may be easily soluble in aqueous media in order to facilitate contact of the pharmaceutical composition with the surrounding aqueous media rapidly after administration. In some embodiments, the cosmetic coat may be dissolved within 30 minutes after immersed in aqueous media such as, for example, phosphate buffer solution pH 6.8.

Sweetening Agents, Flavouring Agents and Colouring Agents

In some embodiments, the capsule, the tablet or any other swallowable compositions may comprise one or more agents selected from sweetening agents, flavoring agents and coloring agents to provide an elegant and palatable preparation. Examples may include maltol, citric acid, water soluble FD&C dyes and mixtures thereof with corresponding lakes and direct compression sugars such as Di-Pac from Amstar. In addition, colored dye migration inhibitors such as; tragacanth, acacia or attapulgite talc may be added. Specific examples include calcium carbonate, 1,3,5-trihydroxybenzene, chromium-cobalt-aluminum oxide, ferric ferrocyanide, ferric oxide, Iron ammonium citrate, iron (III) oxide hydrated, iron oxides, carmine red, magnesium carbonate and titanium dioxide.

Active Drug Substance

In some embodiments, an active drug substance suitable for use in the delivery devices may be a therapeutically, prophylactically and/or diagnostically active drug substance (herein also abbreviated "active drug substance").

In some embodiments, an active drug substance suitable for use in the delivery devices may be a low permeable active drug substance.

In some embodiments, a delivery device may comprise one active drug substance or more than one different active drug substances. In some embodiments, the amount of the active drug substance may correspond to a daily or part of a daily therapeutic dose.

In some embodiments, a payload may include one or more active drug substances for delivery after administration. A wide range of active drug substances may be used. active drug substances may include, but are not limited to, therapeutic active drug substances. For example, antibiotics, NSAIDs, angiogenesis inhibitors, neuroprotective agents, chemotherapeutic agents, cytotoxic agents, diagnostic agents, prophylactic agents (for example vaccines), and/or nutraceutical agents (for example vitamins, minerals, etc.), or other active drug substances that may be suitable for introduction to biological tissues.

In some embodiments, a payload may include one or more bioactive agents. In some embodiments, immunotherapy for allergies such as for example grass, dust mites, ragweed, peanut, tree pollen (for example birch, ash etc.). in some embodiments, immunotherapy and immune-system stimulating agents to support or boost the immune-system to fight cancer such as for example granulocyte colony-stimulating factor (G-CSF), interferons, imiquimod, cellular membrane fractions from bacteria, IL-2, IL-7, IL-12, various chemokines, synthetic cytosine phosphate-guanosine (CpG) oligodeoxynucleotides and glucans.

In some embodiments, an active drug substance may be or may comprise a biologic. Examples of biologics including, but are not limited to, monoclonal antibodies, single chain antibodies, aptamers, enzymes, peptides, growth factors, hormones, fusion proteins, cytokines, therapeutic enzymes, recombinant vaccines, blood factors, and anticoagulants.

In some embodiments, an active drug substance may be a small molecule and/or organic compound with pharmaceutical activity. In some embodiments, an active drug substance may be or may comprise an anti-cancer agent, antibiotic, anti-viral agent, anesthetic, anticoagulant, inhibitor of an enzyme, steroidal agent, anti-inflammatory agent, antineoplastic agent, antigen, vaccine, antibody, decongestant, antihypertensive, sedative, birth control agent, progestational agent, anti-cholinergic, analgesic, anti-depressant, anti-psychotic, adrenergic blocking agent, diuretic, cardiovascular active agent, vasoactive agent, anti-glaucoma agent, neuroprotectant, angiogenesis inhibitor, etc.

In some embodiments, an active drug substance may be a therapeutic gene as known in the art. In some embodiments, a therapeutic agent may be a non-viral vector. Typical non-viral gene delivery vectors comprise DNA (for example, plasmid DNA produced in bacteria) or RNA. In some embodiments, a non-viral vector may be used in accordance with the present disclosure with the aid of a delivery vehicle. Delivery vehicles may be based around lipids (for example, liposomes) which fuse with cell membranes releasing a nucleic acid into the cytoplasm of the cell.

Alternatively, peptides or polymers may be used to form complexes (for example, in form of particles) with a nucleic acid which may condense as well as protect the therapeutic activity as it attempts to reach a target destination.

In some embodiments, an active drug substance may be selected from among amino acids, vaccines, antiviral agents, nucleic acids (for example, siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic, anesthetics, antihistamines, anti-inflammatory agents, vitamins and/or any combination thereof.

In some embodiments, an active drug substance may be selected from suitable proteins, peptides and fragments thereof, which may be naturally occurring, synthesized or recombinantly produced. In some embodiments, an active drug substance may be or may comprise a cell. Such a delivery device may be useful for the injection of whole cells (for example, stem cells).

In some embodiments, pharmaceutical compositions provide oral delivery of low permeable and/or low water soluble active drug substances such as peptides, and other biologics. In some embodiments, active drug substances suitable for use may include large molecule peptides and proteins which may otherwise require injection due to low absorption in the gastrointestinal tract.

In some embodiments, an active drug substance may be selected from various chemotherapeutic agents (for example interferon), antibiotics, antivirals, insulin and related substances, somatostatin and analogs, glucagon like peptides (for example GLP-1, exenatide, efpeglenatid), growth hormone (for example IFG, C-type natriuretic peptide and other growth factors), parathyroid hormone and analogues, anti-seizure agents, immune suppression agents and anti-parasitic agents such as various anti-malarial agents and/or mixture of protease inhibitors for treatment of for example HIV and AIDS.

In some embodiments, an active drug substance may be selected for the treatment of for example cancer, metabolic disorders, hematological, immunological disorders, genetic disorders, hormonal disorders, infectious disease, disorders bone disorders, cardiac disorders, respiratory disorders, neurological disorders, adjunct therapy, eye disorders, malabsorption disorder, Inflammatory disorders, vascular diseases, dermatological disorders, gastrointestinal disorders, neurological disorders, mental disorders, renal disorders, respiratory disorders and/or sexual health disorders.

In some embodiments, an active drug substance may be such as for example Cetuximab, Denileukin diftitox, Leuprolide, Asparaginase, Thyrotropin Alfa, Oprelvekin, Palifermin, Aldesleukin, Pegaspargase, Interferon beta-1a, Trastuzumab, Rituximab, Ibritumomab, Tositumomab, Alemtuzumab, Capromab, Arcitumomab, Panitumumab, Natural Alpha Interferon or Multiferon, Ipilimumab, Pertuzumab, Buserelin, Brentuximab Vedotin, Aflibercept, Epoetin Zeta, Obinutuzumab, Gemtuzumab ozogamicin, Ancestim, Atezolizumab, Blinatumomab, Daratumumab, Elotuzumab, Filgrastim-sndz, Ramucirumab, Pembrolizumab, Ofatumumab, Nivolumab, Necitumumab, Dinutuximab, Ibritumomab tiuxetan, Sipuleucel-T, Cabozantinib, Olaratumab, Lenalidomide, Imatinib, Pemetrexed, Abiraterone Acetate, Enzalutamide, Hpv Quadrivalent Vaccine, Nilotinib, Dasatinib, Everolimus, Bortezomib, Erlotinib, Leuprorelin, Sunitinib Malate, Pomalidomide, Paclitaxel Protein-Bound, Sorafenib, Deferasirox, Goserelin Acetate, Ibrutinib, Bendamustine, Palbociclib, Fulvestrant, Ibrutinib, Azacitidine, Pazopanib, Gefitinib, Aprepitant, Carfilzomib and/or Capecitabine for the treatment of for example cancer.

In some embodiments, an active drug substance may be such as for example Lepirudin, Dornase alfa, Dornase alfa, Bivalirudin, Alteplase, Reteplase, Antihemophilic Factor, Anistreplase, Tenecteplase, Coagulation factor VIIa, Clotting factors (for example Factor, II, V, VII, X and/or XII), Glucagon recombinant, Insulin Lispro, Insulin Glargine, Rasburicase, Imiglucerase, Abciximab, Alpha-1-proteinase inhibitor, Pegademase bovine, Human Serum Albumin, Eptifibatide, Insulin, porcine, Pancrelipase, Streptokinase, Alglucerase, Laronidase, Serum Albumin, Coagulation Factor Ix, Agalsidase Beta, Idursulfase, Alglucosidase Alfa, Exenatide, Pramlintide, Galsulfase, Insulin Aspart, Insulin Detemir, Insulin Glulisine, Insulin, Isophane or Nph Insulin (Neutral Protamine Hagedorn), Aliskiren, Somatotropin Recombinant, Alirocumab, Dulaglutide, Elosulfase alfa, Evolocumab, Insulin Pork, Insulin Degludec, Insulin Beef, Protein S human, Sitagliptin, Insulin Lispro, Metformin, Sitagliptin, Biphasic Insulin Aspart, Canagliflozin, Metformin HCl, Vildagliptin, Linagliptin, Saxagliptin, Metoprolol Hydrochloride and/or Acarbose for the treatment of for example metabolic disorders.

In some embodiments, an active drug substance may be such as for example Lepirudin, Bivalirudin, Alteplase, Darbepoetin alfa, Reteplase, Epoetin alfa, Antihemophilic Factor, Anistreplase, Tenecteplase, Coagulation factor VIIa, Clotting factors (for example Factor, II, V, VII, X and/or XII), Collagenase, Human Serum Albumin, Eptifibatide, Serum albumin iodinated, Coagulation Factor Ix, Ranibizumab, Pegaptanib, Sulodexide, Fibrinolysin Aka Plasmin, Antithrombin Alfa, Antithrombin III human, Coagulation Factor XIII A-Subunit, (Recombinant), Desirudin, Fibrinogen Concentrate (Human), Idarucizumab, Turoctocog alfa, Simoctocog Alfa, Prothrombin complex concentrate, Methoxy polyethylene glycol-epoetin beta, Anti-inhibitor coagulant complex, Coagulation factor X human, Efmoroctocog alfa, Factor IX Complex (Human), Protamine sulfate, Susoctocog alfa, Thrombomodulin Alfa, Eculizumab, Epoetin Alfa, Enoxaparin Sodium, Clotting factors (for example Factor, II, V, VII, X and/or XII), Recombinant Human Coagulation Factor Viia and/or Dabigatran Etexilate of the treatment of for example hematological disorders.

In some embodiments, an active drug substance may be such as for example Etanercept, Peginterferon alfa-2a, Interferon alfa-n1, Interferon alfa-n3, Pegfilgrastim, Sargramostim, Peginterferon alfa-2b, Anakinra, Intravenous Immunoglobulin, Interferon gamma-1b, Interferon Alfa-2a, Recombinant, Omalizumab, Adalimumab, Interferon beta-1a, Infliximab, Interferon beta-1b, Interferon alfacon-1, Rituximab, Basiliximab, Muromonab, Efalizumab, Antithymocyte Globulin, Filgrastim, Interferon Alfa-2B Recombinant, Daclizumab, Abatacept, Thymalfasin, Defibrotide, Canakinumab, Tocilizumab, Rilonacept, Ustekinumab, Golimumab, Belatacept, Belimumab, Raxibacumab, Natalizumab and other immunosuppressive antibodies either of humanized or non-humanized types, Ragweed, Grass or Peanut Pollen Extracts, Secukinumab, Alefacept, Aprotinin, Human Rho(D) immune globulin, Immune Globulin Human, Vedolizumab, Siltuximab, Anthrax immune globulin human, Anti-thymocyte Globulin (Equine), Anti-thymocyte Globulin (Rabbit), Brodalumab, Canakinumab, Lenograstim, Tacrolimus, Cyclosporine, Mycophenolate Mofetil, Romiplostim, Upadacitinib and/or Tofacitinib Citrate for the treatment of for example immunological disorders.

In some embodiments, an active drug substance may be such as for example Insulin Regular, Glucagon recombinant, Insulin Lispro, Insulin Glargine, Rasburicase, Abciximab, Human Serum Albumin, Pancrelipase, Serum Albumin, Coagulation Factor Ix, Sulodexide, Lucinactant, Natalizumab, Asfotase Alfa, Blinatumomab, C1 Esterase Inhibitor (Human), Conestat alfa, Evolocumab, Fibrinogen Concentrate (Human), Sebelipase alfa, Sacrosidase and/or Idursulfase for the treatment of for example genetic disorders.

In some embodiments, an active drug substance may be such as for example Secretin, Insulin Regular, Menotropins, Glucagon recombinant, Lutropin alfa, Insulin Lispro, Insulin Glargine, Follitropin beta, Vasopressin, Insulin, porcine, Pegvisomant, Urofollitropin, Choriogonadotropin Alfa, Oxytocin, Exenatide, Mecasermin, Pramlintide, Cosyntropin, Corticotropin, Insulin Aspart, Insulin Detemir, Insulin Glulisine, Sulodexide, Liraglutide, Buserelin, Velaglucerase Alfa, Tesamorelin, Taliglucerase Alfa, Asparaginase *Erwinia chrysanthemi*, Glucarpidase, Insulin, Isophane, Nph Insulin (Neutral Protamine Hagedorn), Follitropin Alpha, Somatotropin Recombinant, Abarelix, Sermorelin, Albiglutide, Gastric intrinsic factor, Human calcitonin, Thyroglobulin, Chorionic Gonadotropin (Human), Chorionic Gonadotropin (Recombinant), Somatropin, Cinacalcet, Somatropin, Levothyroxine Sodium and/or Testosterone recombinant for treatment of for example hormonal disorders.

In some embodiments, an active drug substance may be such as for example Interferon alfa-n1, Gramicidin D, Aldesleukin, Interferon beta-1a, Interferon alfacon-1, Daptomycin, Enfuvirtide, Palivizumab, Thymalfasin, Natural Alpha Interferon, Multiferon, Teicoplanin, Raxibacumab, Drotrecogin alfa, OspA lipoprotein, Hepatitis B immune globulin, Human *Clostridium tetani* toxoid immune globulin, Human rabies virus immune globulin, Ustekinumab, Tuberculin Purified Protein Derivative, Obiltoxaximab, Ixekizumab, Hepatitis A Vaccine, Human Varicella-Zoster Immune Globulin, Sofosbuvir, Velpatasvir, Emtricitabine, Rilpivirine, Tenofovir Alafenamide, Emtricitabine, Tenofovir Alafenamide, Elbasvir, Grazoprevir, Ledipasvir, Sofosbuvir, Sofosbuvir, Emtricitabine, Tenofovir Disoproxil Fumarate, Efavirenz, Emtricitabine, Tenofovir Disoproxil Fumarate, Cobicistat, E Ivitegravir, Emtricitabine, Tenofovir Disoproxil Fumarate, Darunavir, Ombitasvir, Paritaprevir, Ritonavir, Daclatasvir, Asunaprevir, Raltegravir, Measles, Mumps, Rubella, Varicella Virus Vaccine Live, Rilpivirine, Emtricitabine, Tenofovir Disoproxil Fumarate, Entecavir, Efavirenz, Atazanavir Sulphate, Tenofovir Disoproxil Fumarate, Abacavir, Dolutegravir, Lamivudine, Abacavir, Lamivudine, Dolutegravir, Lopinavir, Ritonavir, Oseltamivir Phosphate, Simeprevir, Rotavirus Vaccine, Pneumococcal Vaccine Polyvalent, Pneumococcal 7-Valent Conjugate, Linezolid, Ertapenem, Moxifloxacin Hydrochloride, Imipenem, Cilastatin, Tigecycline, Azithromycin, Meropenem Hydrate, Voriconazole, Caspofungin, Posaconazole and/or Micafungin sodium for the treatment of for example infectious disease.

In some embodiments, an active drug substance may be such as for example Salmon Calcitonin, Adalimumab, Preotact, Teriparatide, Denosumab, Autologous cultured chondrocytes and/or Pegloticase for the treatment of bone disorders, Digoxin Immune Fab (Ovine), Becaplermin, Bevacizumab, Nesiritide, Alirocumab, Evolocumab and/or C1 Esterase Inhibitor (Recombinant) for the treatment of for example cardiac disorders, Alpha-1-proteinase inhibitor, Beractant, Poractant alfa and/or Mepolizumab for treatment of for example respiratory disorders, Botulinum Toxin Type B, Botulinum Toxin Type A, Glatiramer Acetate and/or Peginterferon beta-1a for the treatment of for example neurological disorders, Hyaluronidase, Follitropin Alpha, Hyaluronidase (Human Recombinant) and/or Metreleptin for the treatment of for example adjunct therapy, Ranibizumab, Pegaptanib and/or Ocriplasmin for the treatment of for example eye disorders and Teduglutide for the treatment of for example malabsorption disorder.

In some embodiments, an active drug substance may be such as for example Mesalamine, Diclofenac, Colchicine, Celecoxib and/or Hyoscine Butylbromide for the treatment of for example Inflammatory disorders.

In some embodiments, an active drug substance may be such as for example Rosuvastatin Calcium, Ezetimibe, Rivaroxaban, Clopidogrel Bisulfate, Hydrochlorothiazide, Valsartan, Ezetimibe, Simvastatin, Bosentan, Amlodipine, Valsartan, Telmisartan, Amlodipine, Telmisartan, Irbesartan, Irbesartan, Hydrochlorothiazide, Ambrisentan, Nebivolol, Ticagrelor, Ranolazine, Prasugrel, Azilsartan and/or Macitentan for the treatment of for example vascular diseases.

In some embodiments, an active drug substance may be such as for example Ecallantide for the treatment of dermatological disorders.

In some embodiments, an active drug substance may be such as for example Omeprazole, Esomeprazole Magnesium, Pantoprazole, Lansoprazole, Dexlansoprazole and/or Mesalazine for the treatment of for example gastrointestinal disorders.

In some embodiments, an active drug substance may be such as for example Cariprazine, Pregabalin, Dimethyl Fumarate, Aripiprazole, Fingolimod, Paliperidone Palmitate, Lisdexamfetamine Dimesylate, Duloxetine, Quetiapine Fumarate, Lurasidone, Risperidone, Olanzapine, Teriflunomide, Methylphenidate, Atomoxetine, Aripiprazole, Rivastigmine, Desvenlafaxine, Varenicline, Lamotrigine, Paliperidone and/or Memantine Hydrochloride for the treatment of for example neurological and mental disorders.

In some embodiments, an active drug substance may be such as for example Mirabegron for the treatment of for example renal disorders.

In some embodiments, an active drug substance may be such as for example Salmeterol, Tiotropium Bromide, Budesonide, Montelukast Sodium, Mometasone Furoate, Fluticasone Propionate, Albuterol and/or Ivacaftor for the treatment of for example respiratory disorders.

In some embodiments, an active drug substance may be such as for example Tadalafil for the treatment of for example sexual health disorders.

In some embodiments, the active drug substance may be for example peptides such as for example human growth hormone, C-type natriuretic peptide, parathyroid hormone, insulin and analogues, GLP-1 analogues for example efpeglenatid, glucagon, heparin, octreotide, calcitonin, Interferon beta-1a, somatostatin, interferons and analogues and/or antibodies such as for example adalimumab, infliximab and/or vaccines such as for example HPV and hepatitis A.

In some embodiments, the payload may contain for example peptide hormones such as for example human growth hormone, parathyroid hormone, insulin, glucagon, octreotide, calcitonin, somatostatin, interferons and analogs, peptide YY and/or gastric inhibitory peptides (GIP).

In some embodiments, the payload may contain for example polypeptides for example for digestion such as for example pancreatic polypeptide and/or glycopeptide metformin.

In some embodiments, the payload may contain for example DPP4 inhibitors such as for example sitagliptin, vildagliptin, saxagliptin, linagliptin, gemigliptin, anagliptin, teneligliptin, alogliptin, trelagliptin, omarigliptin, evogliptin, dutogliptin and/or berberine lopeol.

In some embodiments, the payload may contain for example sodium/glucose co-transporter 2 (SGLT2) inhibitors such as for example dapagliflozin, empaglifozin, canaglifocin, tofoglifocin, serglifocin, remoglifocin, ertuglifocin and/or sotaglifocin.

In some embodiments, the payload may contain for example GLP-1 analogues such as for example incretins, efpeglenatid, exenatide, liraglutide, pramlintide, GnRH and analogs such as for example abarelix, cetrorelix, degarelix, ganirelix, elagolix relugolix, KLH-2109 and/or ASP-1707.

In some embodiments, the payload may contain for example vasopressin and analogues such as for example desmopressin, felypressin, ornipressin, selepressin and/or terlipressin.

In some embodiments, the active drug substance may typically present in the payload in an amount of from 1-99% w/w, such as for example, from about 5-90% w/w, from about 5 to about 80% w/w, from about 5 to about 70% w/w, from about 5 to about 60% w/w, from about 5 to about 50% w/w, from about 5 to about 40% w/w, from about 5 to about 30% w/w, from about 5 to about 20% w/w, from about 5 to about 10% w/w.

In some embodiments, the active drug substance may typically present in the payload in an amount of from 0.5-99% w/w, such as for example 1-90% w/w such as, from about 1 to about 80% w/w, from about 1 to about 70% w/w, from about 1 to about 60% w/w, from about 1 to about 50% w/w, from about 1 to about 40% w/w, from about 1 to about 30% w/w, from about 1 to about 20% w/w, from about 1 to about 10% w/w.

Active Drug Substance Form

In some embodiments, the active drug substance may be present in any of its crystalline, polymorphous, semi-crystalline, amorphous and/or polyamorphous forms.

In some embodiments, the active drug substance may be present in a solid, a liquid, solid dispersed and/or an amorphous solid solution.

In some embodiments, the delivery devices may be suitable for use for both water soluble as well as slightly soluble or insoluble active drug substances.

In some embodiments, the delivery devices may be suitable for use for both permeable as well as slightly permeable or low permeable active drug substances.

Pharmaceutically Acceptable Salts

In some embodiments, all the above mentioned active drug substances may also be in the form of pharmaceutically acceptable salts, uncharged or charged molecules, molecular complexes, solvates or anhydrates thereof, and, if relevant, isomers, enantiomers, racemic mixtures, and mixtures thereof.

In some embodiments, the delivery devices may comprise pharmaceutically acceptable salts of any of the above mentioned active drug substances.

In some embodiments, pharmaceutically acceptable salts may refer to an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc.

In some embodiments, solvates may refer to and include hydrates or solvates wherein other solvates than water may be involved such as, for example organic solvents like chloroform and the like.

In some embodiments, the concentration of the active drug substance in the delivery device may depend on the specific active drug substance, the disease to be treated, the condition of the patient, the age and gender of the patient etc. in some embodiments, the above-mentioned active drug substances may be known active drug substances and a person skilled in the art will be able to find information as to the dosage of each active drug substance and, accordingly, will know how to determine the amount of each active drug substance in the composition of a delivery device.

In some embodiments, the active drug substance may be a new chemical entity for which the amount of information is limited. In such cases, the dosage may be evaluated based on available preclinical and/or clinical data.

General Production Materials

Polymer

In some embodiments, materials such as for example polymer may be used for the delivery device, body delivery part and/or the payload or part of it may be selected and adapted for a particular use or design.

In some embodiments, the delivery device may comprise specific design elements comprising thermoplastic materials, which may facilitate efficient absorption and access to the blood stream. In some embodiments, the delivery device may comprise specific design elements comprising thermoplastic materials, which may facilitate efficient absorption and access to the blood stream in the gastrointestinal tract.

Additionally or alternatively, the delivery device, body, delivery part and/or payload may comprise a water soluble, water insoluble, degradable and/or pH-dependent polymer.

In some embodiments, the delivery part or a part of it may comprise a degradable polymer and/or pH-dependent polymer. In some embodiments, the delivery part may include a payload so that the payload is released after the degradation and/or dissolution of the delivery part.

In some embodiments, suitable polymers as discussed herein may be selected and adapted to have a desired degradation rate and/or dissolution rate. Alternatively, or additionally, a degradation rate and/or dissolution rate may be fine-tuned by associating or mixing other materials as described herein.

In some embodiments, the thermoplastic material may for example be polymers that may be formed by heat and may be used to create desired shapes of the material. In one embodiment, thermoplastic materials may be manufactured to the desired shape by injection molding, 3D-printing or hot melt extrusion, which is also described further below.

In some embodiments, the delivery device in general may comprise or even consist of one or more polymers. In some embodiments, at least one polymer may be a thermoplastic polymer. In some embodiments, all polymers in the delivery device may be thermoplastic polymers.

As used herein, "thermoplastic polymers" refers to polymers that may be an elastic and flexible liquid when heated and freezes to a solid state when cooled (for example, cooled to 20° C. or to ambient temperature).

In some embodiments, the delivery device may be made of a material comprising one or more of the polymers. For example, the delivery device may be made of a material comprising one or more starch based polymers, one or more cellulose based polymers, one or more synthetic polymers, one or more biodegradable polymers or a combination thereof, such as mixtures of starch and synthetic polymers or mixtures of starch and biodegradable polymers.

In some embodiments, a thermoplastic polymer may be made up of long, unlinked polymer molecules, generally with a high molecular weight. Because the molecular chains may be unlinked, they rely on other interactions, such as dipole-dipole interactions, aromatic ring stacking, or Van der Waals forces. Thermoplastics generally form a crystalline structure when cooled below a certain temperature, resulting in a smooth surface finish and significant structural strength. Above this temperature, thermoplastics may be elastic. As the temperature increases, thermoplastics gradually soften, eventually melting.

Starch Based Polymers

In some embodiments, the delivery device, body delivery part and/or the payload may comprise one or more starch based polymers. In some embodiments, the starch based polymer may be starch as such or a polymer having a high starch content selected from more than 70% starch, more than 80% starch, or more than 90% starch. Starch is a linear polysaccharide made up of repeating glucose groups with glyosidic linkages. There are two major polymer molecules in starch—amylose and amylopectin.

In some embodiments, starch based polymers may be used in forming a delivery device, body delivery part and/or the payload may be thermoplastic starch biodegradable plastics (TPS). TPS have a starch (amylose) content greater than 70% and are, in general, based on gelatinized vegetable starch. Said vegetable starch may for example be selected from the group consisting of potato starch, rice starch, maize starch, tapioca starch, wheat starch, dextrin, carrageenan and chitosan. Said vegetable starch may provide suitable polymers used in the delivery device, body delivery part and/or the payload. Starch based polymers, in general, do not have a specified melting point, but typically change phase within a temperature range of 90° C. to 260° C., depending upon the chain length of the starch based polymer, water content, and their branching and added side-groups as does the degree of crystallinity of the starch. Long chained-starches are usually completely amorphous, while shorter length starches may be semi-crystalline (20-80% crystalline). In some embodiments, relatively long polymer chains may contribute to the hardness of the delivery device, body delivery part and/or the payload, while not being too brittle.

In some embodiments, starch-based polymers may be in general fully biodegradable as they are product of plant materials. The degradation rate varies and may be further induced by addition of other biodegradable polymers as listed herein.

In some embodiments, the starch based polymer may be maize starch. Maize starch is a linear polysaccharide made up of repeating glucose groups with glyosidic linkages. There are two major polymer molecules in starch—amylose and amylopectin. An example of a suitable maize starch is Corn pack.

In some embodiments, starch is widely used in the food and pharmaceutical industries as a binder and diluent. It is edible and essentially nontoxic. Starch is in general cheap and obtains a good hardness when molded. Starch may, in general, also be reheated several times without losing its thermodynamic properties. In some embodiments, delivery device, body delivery part and/or the payload may comprise at least one starch based polymer. In some embodiments, delivery device, body delivery part and/or the payload may comprise a starch. In some embodiments, utilization of a starch in forming the delivery device, body delivery part and/or the payload may be a great advantage when applying injection molding or 3D printing or co-extrusion as a production process.

In some embodiments, starch based polymers may be in general decomposable, and usually have a fast disintegration rate, especially in mixture with biodegradable polymers. Starch based polymers are in generally recognized as stable and inert in solid dosage forms.

Cellulose Based Polymers

In some embodiments, delivery device, body delivery part and/or the payload may comprise one or more cellulose based polymers. In some embodiments, delivery device, body delivery part and/or the payload may even consist of one or more cellulose based polymers (such as for example ethyl cellulose) combined with one or more and plasticizers (such as any of the plasticizers described herein) and UV stabilizers (such as any of the UV stabilizers described herein).

In some embodiments, cellulose based polymers may be useful in forming a delivery device, body delivery part and/or the payload because cellulose based polymers, for example, ethyl cellulose (particularly grade 100-300), frequently have increased hardness and high ductility.

In some embodiments, delivery device, body delivery part and/or the payload may comprise a cellulose based polymer. The cellulose based polymer may be cellulose, wherein one or more of the free —OH groups have been substituted with an R-group to form a —O—R group. R may in this context, for example, be linear or branched lower alkyl, linear or branched lower alkyl-OH, linear or branched lower alkyl-COOH, —CO-(linear or branched lower alkyl), nitrate, aromatic rings or combinations of the aforementioned. Lower alkyl is preferably a $C_{1-10}$ alkyl, more preferably $C_{1-6}$ alkyl.

In some embodiments, the cellulose based polymer may, for example, be one or more selected from ethyl cellulose, cellulose acetate, cellulose propionate, cellulose nitrate, methylcellulose, carboxymethylcellulose and salts thereof, cellulose acetate phthalate, include hydroxypropyl methylcellulose phthalate (HPMC-P), ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose and cellulose acetate.

In some embodiments, delivery device, body delivery part and/or the payload may comprise one or more cellulose based polymers selected from cellulose acetate, cellulose propionate, silicified microcrystalline cellulose, cellulose nitrate, methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose phthalate, hydroxymethylcellulose and hydroxymethylpropylcellulose, cellulose acetate, ceratonia (high molecular-weight 310 000 Daltons).

In some embodiments, cellulose based polymers may be, in general fully, biodegradable as they preferably are products of plant materials. The degradation rate of cellulose based polymers is, in general, slower than that of starch based polymers. This degradation rate may be induced or increased by addition of other biodegradable polymers as listed herein. These other polymers may be polymers which may be attacked by microorganism which degrades delivery device, body delivery part and/or the payload into smaller pieces giving rise to a bigger surface and thereby faster degradation.

In some embodiments, delivery device, body delivery part and/or the payload may comprise ethyl cellulose $C_{12}H_{23}O_6$ $(C_{12}H_{22}O_5)_n C_{12}H_{23}O_5$, where n can vary to provide a wide variety of molecular weights. Ethyl cellulose, an ethyl ether of cellulose, is a long-chain polymer of β-anhydroglucose units joined together by acetal linkages. Ethyl cellulose comes in different grades, which vary in molecular weight and number of ethoxy groups. In some embodiments, the ethyl cellulose may be selected from one or more of grades from 20-300, which are commercially available. Grades with high molecular weights may also be used because they may be optimal to give a delivery device, body delivery part and/or the payload. In some embodiments, delivery device, body delivery part and/or the payload may comprise one or more ethyl celluloses with different grades. For example, delivery device, body delivery part and/or the payload may include a first ethyl cellulose with a grade selected from a grade ranging from 20 to 300, a grade ranging from 20 to 100, a grade ranging from 20 to 40, and a grade of 20 and/or a second ethyl cellulose with a grade selected from a grade ranging from 20 to 300, a grade ranging from 50 to 200, a grade ranging from 80 to 120, and a grade of 100. Ethyl cellulose generally has a glass transition temperature within 129-133° C. These polymers are widely used in food and pharmaceutical industry as coater, stabilizer, matrix former and taste masking and are regarded as nontoxic substances.

In some embodiments, cellulose based polymers may be, in general, derived from plant material and may subsequently be modified. Many cellulose-based polymers may be cheap and give a good hardness when molded. As derivatives of plants, cellulose based polymers may be in general easily decomposable when disposed. These polymers may be generally stable and inert when incorporated in solid dosage forms.

Synthetic Polymers

In some embodiments, delivery device, body delivery part and/or the payload may comprise one or more synthetic polymers. Suitable synthetic polymers for use in delivery device, body delivery part and/or the payload may, for example, be one or more selected from polyamide, polyethylene, polyethylene terephthalate, polypropylene, polyurethane, polyvinyl acetate, polyvinyl alcohol, polyvinyl butural, polyvinyl chloride), Eudragit L methyl ester, Eudragit RL, Eudragit RS, Eudragit S and Eudragit E, silicone rubber, latex, resin, shellac, Polytetrafluoroethylene (teflon), copolymers such as ethylene vinyl acetate (EVA), styrene-butadienestyrene (SBS) and styrene-isoprene-styrene (SIS), Polyethylene glycols, polyvinylpyrrolidone, polyethylene oxide (ranging in molecular weights 100,000 to 8,000,000 daltons), carboxymethylene (Carbomer) and sugars thereof (for example, allylsucrose) and co-polymers of ethylene and propylene oxide (Poloxamers), polyvinylchloride (PVC), polytetrafluoroethylene (PTFE), Polyethersulfone (PES), polyethylene (PE), polyetheretherketone (PEEK), polysulfone (PS), polypropylene (PP), hydroxypropyl methylcellulose acetate succinate (HPMCAS), polydioxanone (PDS), Poly(methyl acrylate), Poly(methyl methacrylate), Polyhydroxyethylmethacrylate, poly(monosteroyl glyceryl-co-succinate), copolymers of vinylpyrrolidone, polydimethylene-siloxane, poly(N-isopropyl acrylamide), Poly(amidoamine) dendrimers, polyacrylic acid, polyacrylamide, poly(2-(dimethylamino)ethyl acrylate (PDEAEMA), poly(2-(dimethylamino)ethyl methacrylate (PDMAEMA), Poly(methyl methacrylate), Polyhydroxyethylmethacrylate, polyorthoesters, polyacrylic acid, polyalkyl cyanoacrylates, poly(n-butylcyanoacrylate) (PBCA), Polyhydroxycarboxylic Acid (PHCA).

Biodegradable Polymers

In some embodiments, biodegradation may be the process by which microorganisms (microbes such as bacteria, fungi or algae) convert materials into biomass, carbon dioxide and water. Biomass may be a general term used to refer to the cells of the microorganisms that are using the material as a carbon source.

In some embodiments, delivery device, body delivery part and/or the payload may comprise one or more biodegradable polymers. Said biodegradable polymer(s) may be one or more selected from starch based polymers and cellulose based polymers. The biodegradable polymer may also be one or more selected from polyhydroxybutyrate (PHB), polyhydroxyvalerate (PHV), polyhydroxyvalerate-co-hydroxyvalerate (PHV/VH), Polyhydroxyalkanoates (PHA), poly-3-hydroxy-5-phenylvalerate (PHPV), aliphatic polyesters, polycaprolactone (PCL), polylactic acid (PLA), polyglycolic acid (PGA), copolymers or block copolymers of polycaprolactone (PCL), polylactic acid (PLA) and/or polyglycolic acid (PGA), polypropylene carbonate (PPC), polyester amide (PEA), polybutylene succinate adipate (PBSA), polybutylene adipate co-terephtalate (PBAT) and polybutylene succinate-adipate (PESA), terephthalic acid (PTA), Polyhydroxybutyrate (PHB), polysebatic acid, polyphosphazenes, polyphosphonate, polycyanoacrylates, polyurethenes, polyorthoesters, Polydioxanone (PDS).

In some embodiments, delivery device, body delivery part and/or the payload may comprise one or more copolymers or block copolymers of polycaprolactone (PCL), polylactic acid (PLA) and/or polyglycolic acid (PGA) may, for example, be selected from poly(lactic-co-glycolic acid) (PLGA), polylactic acid and epsilon-caprolactone copolymer (PLA/CL) and polylactic acid/glycolic acid polymers) (PLA/GA), which may all be commercially available.

In some embodiments, delivery device, body delivery part and/or the payload may comprise one or more biodegradable polymers selected from polylactic acid (PLA), polycaprolactone (PCL) and polyhydroxybutyrate (PHB), preferably the delivery device, body delivery part and/or the payload may comprise both polylactic acid (PLA), polycaprolactone (PCL) and polyhydroxybutyrate (PHB).

In some embodiments, delivery device, body delivery part and/or the payload may comprise polycaprolactone and other polymers in this group and the use of polycaprolactone and other polymers in this group has been increased over the last decade, while the demand for environmental friendly plastics has grown. These polymers may be regarded as nontoxic and are already used in parenteral pharmaceutical formulations. Such polymers may facilitate formulation of a more flexible delivery device, body delivery part and/or the payload when molded in mixture with starch derived polymers. The somewhat rigid structure of pure thermoplastic starch may be adjusted as desired by inclusion polycaprolactone or other biodegradable polymers disclosed herein. Furthermore, the biodegradable polymers may be decomposable and disintegrate by microorganisms.

Mixtures of Polymers

In some embodiments, the delivery device, body and/or delivery part and/or payload may comprise one or more different polymers and/or co-polymers. In some embodiments, the delivery device, body and/or delivery part and/or payload may comprise one or more different polymers selected from starch based polymers, cellulose based polymers, synthetic polymers and biodegradable polymers.

In some embodiments, the delivery device, body and/or delivery part and/or payload may comprise more than one different kind of polymer, such as 2, for example 3, such as 4, for example 5, such as more than 5 different polymers. In some embodiments, the delivery device, body and/or delivery part and/or payload may comprise 1 to 4 different polymers. In one such embodiment, the composition may comprise 1 to 3 different polymers. In another such embodiment, the composition may comprise 2 different polymers.

Starch Based Polymers and Biodegradable Polymers

In some embodiments, the delivery device, body and/or delivery part and/or payload may comprise polymers selected from starch based polymers and biodegradable polymers. In some embodiments, the polymers may be selected from any of the starch based polymers and biodegradable polymers. In some embodiments, biodegradable polymers such as polycaprolactone, polyhydroxybuturate, polyhydroxyvalerate, polylactic acid, polyhydroxyalkanoates and/or polypropylenecarbonate may be blended with various starches (such as any of the starches) in different ratios. Suitable mixtures for use in the delivery device, body and/or delivery part and/or payload may be, for example, polycaprolactone and sago and/or cassava starch, polycaprolactone or polyhydroxybuturate and pre-dried, thermoplastic starch, polycaprolactone and gelatinized starch or thermoplastic starch. Other suitable mixtures may include starch-based blends with biodegradable thermoplastic components like polyester amide, polyhydroxybuturate-co-valerate or polybutylene succinate-adipate. Polymers starches may be cross-linked with Maleic anhydride (MA) and dicumyl peroxide (DCP) giving harder items when molded.

Starch Based Polymer and Synthetic Polymers

In some embodiments, the delivery device, body and/or delivery part and/or payload may comprise polymers selected from starch based polymer and synthetic polymers. In some embodiments, the delivery device, body and/or delivery part and/or payload may comprise polymers selected from any of the starch based polymers and synthetic polymers. Suitable mixtures for use in the delivery device, body and/or delivery part and/or payload may include, for example, native granular starch, modified starch, plasticized starch blended or grafted with many synthetic polymers such as polyethylene, polystyrene, Purified Terephthalic acid (PTA), optionally in mixture with aliphatic polyesters or polyvinyl alcohols in different ratios. Polybutylene succinate (PBS), polybutylene succinate adipate in blend with various starches in different ratios may also be suitable such as, for example, Polybutylene succinate in mixture with thermoplastic starch, and alkylene oxide modified starches in combination with hydrolyzed polyvinyl alcohol.

Cellulose Based Polymers and Biodegradable Polymers

In some embodiments, the delivery device, body and/or delivery part and/or payload may comprise polymers selected from cellulose based polymers and biodegradable polymers, such as, for example, any of the cellulose based polymers and biodegradable polymers. Thus, the delivery device, body and/or delivery part and/or payload may for example comprise a mixture of PLA and ethylcellulose.

In some embodiments, the delivery device, body and/or delivery part and/or payload may consist of PLA, ethyl cellulose, one or more plasticizers (such as any of the plasticizers described herein) and one or more UV stabilisers (such as any of the UV stabilisers described herein).

Polyglycols

In some embodiments, the delivery device, device body and/or delivery part may comprise polyglycols in a form, which erodes at a substantially slower rate than the payload. In some embodiments, the delivery device, body and/or delivery part may thus be one which is eroded in an aqueous medium at a substantially slower rate than the payload comprising the active drug substance, whereby a substantially controlled area of the payload comprising the active drug substance may be exposed during erosion and/or release of the payload, and whereby the delivery device, body and/or delivery part may be substantially eroded upon erosion and/or release of the payload comprising the active drug substance. In some embodiments, such a delivery device, body and/or delivery part may be designed so that its longitudinal erosion rate may be substantially the same as the longitudinal erosion and/or release rate of the payload, whereby the payload and the delivery device, body and/or delivery part may erode longitudinally towards the end of the payload at substantially the same rate. Thus, in some embodiments, when the payload may have been completely eroded and/or released by the aqueous medium, the delivery device, body and/or delivery part may also be substantially completely eroded. A payload may have such a delivery device, body and/or delivery part may have the advantage of being completely biodegraded upon release of the active drug substance.

In some embodiments, the polyglycol suitable for inclusion in a delivery device, body and/or delivery part may be high molecular weight PEO, such as a PEO with an average molecular weight which may be significantly higher than the average molecular weight of any of the polyglycols contained in the payload. In some embodiments, it may be preferred that any PEO contained in the delivery device, body and/or delivery part may have a significantly higher average molecular weight than any polyglycol contained in the payload.

In some embodiments, the polyglycol for use in the payload may be in the form of substantially water-soluble, thermoplastic, crystalline, semi-crystalline or amorphous or a mixture of substantially water-soluble, crystalline, semi-crystalline or amorphous polymers. Suitable polymers for use in a payload are polyethylene glycols, may include derivatives such as mono- and dimethoxypolyethylene glycols (mPEGs) and polyethylene oxides. In some embodiments, the payload may be prepared as matrix compositions using the polyglycol polymers.

Polyethylene Glycols (PEGs)

In some embodiments, polyethylene glycols (PEGs) may be linear polydisperse polymers composed of repeating units of ethylene glycol. Their chemical formula is HOCH$_2$[CH$_2$OCH$_2$]$_m$CH$_2$OH where m represents the average number of repeating units. Alternatively, the general formula H[OCH$_2$CH$_2$]$_n$OH may be used to represent polyethylene glycol, where n is a number m in the previous formula+1. See the structural presentations of polyethylene glycol below. n is the average number of oxyethylene groups. n equals m+1.

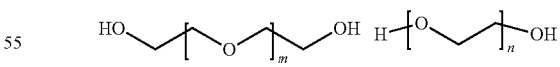

In some embodiments, polyethylene glycols may be mixtures of addition of ethylene glycol. In general PEG refers to polymers chains with molecular weights below 20,000 Daltons, while PEO refers to higher molecular weights polymers. However, because of the similarities between PEO and PEG, the terms may be used interchangeably for the same compound.

In some embodiments, polyethylene glycols and/or polyethylene oxides may be suitable for use in the payload and may have average molecular weights of from 200 Daltons, to 20,000 Daltons such as for example the following average molecular weights: 200, 300, 400, 500, 600, 700, 800, 900, 1000, 1100, 1200, 1300, 1400, 1450, 1500, 1540, 1600, 1700, 1800, 1900, 2000, 2100, 2200, 2300, 2400, 2500, 2600, 2700, 2800, 2900, 3000, 3250, 3350, 3500, 3750, 4000, 4250, 4400, 4500, 4600, 4750, 5000, 5500, 5800, 6000, 6500, 7000, 7500, 8000, 8400, 10,000, 12,000, 14,600, 17,000 or 20,000 Daltons.

In some embodiments, a payload may comprise a polyglycol having a molecular weight of 200, 300, 400, 500, 600, 700, 800, 900, 1000, 1100, 1200, 1300, 1400, 1450, 1500, 1540, 1600, 1700, 1800, 1900, 2000, 2100, 2200, 2300, 2400, 2500, 2600, 2700, 2800, 2900, 3000, 3250, 3350, 3500, 3750, 4000, 4250, 4400, 4500, 4600, 4750, 5000, 5500, 5800, 6000, 6500, 7000, 7500, 8000, 8400, 10,000, 12,000, 14,600, 17,000 or 20,000 Daltons. In some embodiments, the payload may comprise a polyglycol selected from PEG 400, PEG 3350 S, PEG 6000, PEG 10 000, PEG 14 000 and/or PEG 17 000. Thus, in some embodiments, the polyglycol employed in the payload may have a melting point of in the range of 30° C. to 120° C., such as in the range of 35° C. to 100° C., for example in the range of 40° C. to 80° C.

Polyethylene Oxides

In some embodiments, the delivery device, body, delivery part and/or payload may comprise a polyethylene oxide. Polyethylene oxides (PEOs) are linear polydisperse non-ionic polymers composed of repeating units of ethylene oxide. Their chemical formula is HO[CH2CH2O]nH, where n represents the average number of oxyethylene groups. See the structural presentation of polyethylene oxide below, wherein n is the average number of oxyethylene groups. Depending on preparation method, high molecular weight PEO may have one terminal methyl group.

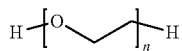

In some embodiments, polyethylene oxides suitable for use in the delivery device, body, delivery part and/or payload may have an average molecular weight of at least about 20,000 Daltons, such as an average molecular weight of at least about 35,000 Daltons such as an average molecular weight of at least about 100,000 Daltons, such as an average molecular weight of at least about 200,000 Daltons, such as an average molecular weight in the range of about 200,000 to about 10,000,000 Daltons, for example in the range of about 250,000 to about 10,000,000 Daltons, such as in the range of about 300,000 to about 10,000,000 Daltons, for example in the range of about 350,000 to about 10,000,000 Daltons, such as in the range of about 400,000 to about 10,000,000 Daltons.

In some embodiments, the polyethylene oxides suitable for use in the delivery device, body, delivery part and/or payload may have an average molecular weight of at the most 1,000,000 Daltons, such as an average molecular weight of in the range of about 200,000 to about 1,000,000 Daltons, for example in the range of about 300,000 to about 1,000,000 Daltons, such as in the range of about 400,000 to about 1,000,000 Daltons, for example in the range of about 200,000 to about 900,000 Daltons, such as in the range of about 200,000 to about 800,000 Daltons, such as in the range of about 200,000 to about 700,000 Daltons, such as in the range of about 200,000 to about 600,000 Daltons.

In some embodiments, the polyethylene oxides suitable for use in the delivery device, body, delivery part and/or payload disclosed herein may be those having an average molecular weight of at the most 600,000 Daltons, such as an average molecular weight of in the range of about 100,000 to about 600,000 Daltons, for example in the range of about 200,000 to about 600,000 Daltons, such as for example in the range of about 250,000 to about 600,000 Daltons, such as in the range of about 300,000 to about 600,000 Daltons, for example in the range of about 350,000 to about 600,000 Daltons, such as in the range of about 400,000 to about 600,000 Daltons, such as in the range of about 450,000 to about 600,000 Daltons, such as in the range of about 500,000 to about 600,000 Daltons.

In some embodiments, the polyethylene oxides suitable for use in the delivery device, body, delivery part and/or payload may be those having an average molecular weight selected from 20,000 Daltons, 35,000 Daltons, 100,000 Daltons, 200,000 Daltons, 250,000 Daltons, 300,000 Daltons, 350,000 Daltons, 400,000 Daltons, 450,000 Daltons, 500,000 Daltons, 550,000 Daltons, 600,000 Daltons, 650,000 Daltons, 700,000 Daltons, 750,000 Daltons, 800,000 Daltons, 850,000 Daltons, 900,000 Daltons, 950,000 Daltons, 1,000,000 Daltons, 2,000,000 Daltons, 3,000,000 Daltons, 4,000,000 Daltons, 5,000,000 Daltons, 7,000,000 Daltons, 10,000,000 Daltons.

In some embodiments, the delivery device, body, delivery part and/or payload may comprise mixtures of polyethylene oxides with different average molecular weights, for example, in order to obtain polyethylene oxides with a desirable average molecular weight. Thus, in some embodiments, the delivery device, body, delivery part and/or payload comprises different polyethylene oxide materials with different average molecular weights.

In some embodiments, in order to obtain polyethylene oxide with a desirable average molecular weight, it is important to note that, in such cases, it is necessary to use polyethylene oxides, which have an average molecular weight closest to the desired molecular weight to ensure a narrow chain length distribution.

Total Concentration of Polymer

In some embodiments, the total concentration of polymer for use in the delivery device, body and/or delivery part may be in the range of 5 to 100% w/w, such as from 10 to 100% w/w, such as from 15 to 100% w/w, such as from 20 to 100% w/w, such as from 25 to 100% w/w, such as from 30 to 100% w/w, such as from 35 to 100% w/w, such as from 40 to 100% w/w, such as from 45 to 100% w/w, such as from 50 to 100% w/w, such as from 55 to 100% w/w, such as from 60 to 100% w/w, such as from 65 to 100% w/w, such as from 70 to 100% w/w.

In some embodiments, the total concentration of polymer for use in the payload may be in the range of from 0 to 99% w/w, for example in the range of 0 to 95% w/w, such as in the range of 0 to 90% w/w, for example in the range of 0 to 85% w/w, such as in the range of 0 to 80% w/w, for example in the range of 0 to 75% w/w, such as in the range of 0 to 70% w/w, for example in the range of 0 to 65% w/w, such as in the range of 0 to 60% w/w, for example in the range of 0 to 55% w/w, such as in the range of 0 to 50% w/w, for example in the range of 0 to 45% w/w, such as in the range of 0 to 40% w/w, for example in the range of 0 to 35% w/w, such as in the range of 0 to 30% w/w, for example in the range of 0 to 25% w/w, such as in the range of 0 to 20% w/w, for example in the range of 0 to 15% w/w, such as in the range of 0 to 10% w/w, for example in the range of 0 to 5% w/w.

In some embodiments, the total concentration of polymer for use in the payload may be at least 1% w/w, for example at least 5% w/w, such as for example at least 10% w/w, such as for example at least 15% w/w, such as for example at least 20% w/w.

In some embodiments, the total concentration of polymer for use in the payload may be at the most 99% w/w, such as in the range of 1 to 99% w/w, for example 5 to 99% w/w, such as in the range of 15 to 99% w/w, for example 20 to 99% w/w, such as in the range of 25 to 99% w/w, for example 30 to 99% w/w.

In some embodiments, the total concentration of polymer for use in the payload may be at least 5% w/w, such as in the range of 5 to 30% w/w, for example 5 to 25% w/w, such as in the range of 5 to 20% w/w, for example 5 to 15% w/w, such as in the range of 5 to 10% w/w.

Polymer Melting Point

In some embodiments, the polymer used in the delivery device, body, delivery part and/or payload may have a melting point higher than the body temperature of the subject for example in which the delivery device is to be used. Thus, in some embodiments, the polymer used in the delivery device, body, delivery part and/or payload may have a melting point of in the range of 38° C. to 250° C., such as in the range of 38° C. to 200° C., such as in the range of 38° C. to 150° C., for example in the range of 38° C. to 120° C., such as in the range of 38° C. to 100° C., for example in the range of 65° C. to 100° C., such as in the range of 65° C. to 120° C., such as in the range of 65° C. to 150° C., such as in the range of 65° C. to 200° C., such as in the range of 65° C. to 250° C.

UV Stabilizer

In some embodiments, Radiation from sunlight may accelerate the degradation of the delivery device, body, delivery part and/or payload. In some embodiments, the packaging material to protect the pharmaceutical compositions (for example capsules or tablets) from direct sunlight may not be enough protection. Especially for a delivery device, body, delivery part and/or payload with high concentration of biodegradable polymers may it be relevant to add UV-stabilizers to the compositions, due to many unsaturated functional groups (for example carbonyl groups). UV-stabilizers may for example be titanium dioxide, metal complexes with sulfur containing groups, hindered amine light stabilizers (HALS), benzophenones, benzotriazoles. Titanium dioxide is already widely used in pharmaceutical preparations as pigment and is considered nontoxic.

Plasticizer

In some embodiments, the delivery device, body, delivery part and/or payload may also comprise at least one plasticizer. In some embodiments, the delivery device, body, delivery part and/or payload may comprise one or more plasticizers.

In some embodiments, other plasticizers may be incorporated in the delivery device, body, delivery part and/or payload and suitable plasticizer may be selected from poloxamer, mono- and di-acetylated monoglycerides, diacetylated monoglycerides, acetylated hydrogenated cottonseed glyceride, glyceryl cocoate, polyethylene glycols (for example with a molecular weight below 35,000 Daltons), polyethylene oxides (for example with a molecular weight of about 35,000 to 600,000 Daltons), dipropylene glycol salicylate glycerin, fatty acids and esters, phthalate esters, phosphate esters, amides, diocyl phthalate, diethyl phthalate, phthalyl glycolate, mineral oils, hydrogenated vegetable oils, vegetable oils, acetylated hydrogenated soybean oil glycerides, castor oil, acetyl tributyl citrate, acetyl triethyl citrate, methyl abietate, nitrobenzene, carbon disulfide, betanaphtyl salicylate, citric acid, tromethamine, xylitol, maltitol, chitosan, sorbitol, sorbitol sorbitan solution, sorbitol glyceryl tricitrate, fatty alcohols, cetostearyl alcohol, cetyl alcohol, stearyl alcohol, oleyl alcohol, myristyl alcohol, sucrose octaacetate, alfatocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2,000, polyoxyethylene 50 stearate, macrogol ethers, cetomacrogol 1000, lauromacrogols, nonoxinols, octocinols, tyloxapol, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, methylene glycol dipelargonate, solid aliphatic alcohols, and mixtures thereof.

In some embodiments, the delivery device, body, delivery part and/or payload may comprise cetostearyl alcohol, castor oil, dibutyl sebacate, polyethylene oxides and/or poloxamer as plasticizer. In some embodiments, the delivery device, body, delivery part and/or payload may comprise polyethylene glycols, polyethylene glycol monomethyl ether, cetostearyl alcohol, cetyl alcohol, stearyl alcohol, alfa-tocopheryl polyethylene glycol succinate (TPGS), triacetin, tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, polysorbate 40, polysorbate 60, polysorbate 65, polysorbate 80, polysorbate 85, acetyl tributyl citrate and/or acetyl triethyl citrate as plasticizer. However, in some embodiments, other plasticizers may also be used to provide desired material properties.

Amount of Plasticizer

In some embodiments, the amount of plasticizer in the delivery device, body, delivery part and/or payload may be in the range of from 0 to 60% w/w, for example in the range of 0 to 50% w/w, such as in the range of 0 to 40% w/w, for example in the range of 0 to 30% w/w, such as in the range of 0 to 20% w/w. In some embodiments, the amount of plasticizer in the delivery device, body, delivery part and/or payload may be at least 1% w/w, for example at least 2% w/w, such as for example at least 3% w/w, such as for example at least 4% w/w, such as for example at least 5% w/w, such as for example at least 6% w/w, such as for example at least 7% w/w, such as for example at least 8% w/w, such as for example at least 9% w/w, such as for example at least 10% w/w. In some embodiments, the amount of plasticizer in the delivery device, body, delivery part and/or payload may be at the most 30% w/w, such as in the range of 0 to 30% w/w, for example 5 to 30% w/w, such as in the range of 10 to 30% w/w, for example 15 to 30% w/w, such as in the range of 20 to 30% w/w, for example 25 to 30% w/w. In some embodiments, the amount of plasticizer in the delivery device, body, delivery part and/or payload may be at least 5% w/w, such as in the range of 5 to 30% w/w, for example 5 to 25% w/w, such as in the range of 5 to 20% w/w, for example 5 to 15% w/w, such as in the range of 5 to 10% w/w.

In some embodiments, the delivery device, body, delivery part and/or payload may comprise one or more plasticizer(s) and one or more polymer(s).

Pharmaceutically Acceptable Excipients

In some embodiments, the delivery device, body, delivery part, payload and/or the pharmaceutical composition may also contain other excipients to achieve one or more desired properties, such as for example a better stability of the active drug substance, delivery device or pharmaceutical composition, loading of the active drug substance or delivery characteristics, such as to adjust the release rate or release profile of an active drug substance. In some embodiments, the delivery device, body, delivery part, payload and/or the pharmaceutical composition may include excipients that facilitate manufacture and production such as for example tablets, capsules or suppository suitable for administration to individuals in need thereof.

In some embodiments, the delivery device, body, delivery part, payload and/or the pharmaceutical composition may include a pharmaceutically acceptable excipient selected from a mono-, di-, oligo, polycarboxylic acid or amino acids such as, for example, acetic acid, succinic acid, citric acid, tartaric acid, acrylic acid, benzoic acid, malic acid, maleic acid, sorbic acid etc., aspartic acid or glutamic acid etc.

In some embodiments, the delivery device, body, delivery part, payload and/or the pharmaceutical composition may include a pharmaceutically acceptable excipient selected from fillers, diluents, effervescent, disintegrants, wicking agent glidants, pH-adjusting agents, viscosity adjusting agents, solubility increasing or decreasing agents, surfactants, hygroscopic agents, osmotically active agents and solvents.

In some embodiments, the delivery device, body, delivery part, payload and/or the pharmaceutical composition may include a pharmaceutically acceptable excipient selected from conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), carboxymethylcellulose, methylcellulose, veegum, larch arabolactan, polyethylene glycols, ethylcellulose, water, alcohols, waxes, polyvinylpyrrolidone such as PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium lauryl sulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including crosscarmellose, gums, aligns, various combinations of hydrogencarbonates with weak acids (for example, sodium hydrogencarbonate/tartaric acid or citric acid) crosprovidone, sodium starch glycolate, agar, cation exchange resins, citrus pulp, glycollate, natural sponge, bentonite, sucralfate, calcium hydroxyl-apatite or mixtures thereof.

In some embodiments, the delivery device, body, delivery part, payload and/or the pharmaceutical composition may include a pharmaceutically acceptable excipient selected from polymer such as polyglycols selected from substantially water soluble, thermoplastic, crystalline, semi-crystalline or amorphous or a mixture of substantially water soluble, crystalline, semi-crystalline or amorphous polymers. In some embodiments, the delivery device, body, delivery part, payload and/or the pharmaceutical composition may include a pharmaceutically acceptable excipient selected from suitable polyglycols for example derivatives of polyethylene glycol, such as mono or dimethoxypolyethylene glycols (mPEGs), polyethylene oxides and/or block copolymers of ethylene oxide and propylene oxide.

In some embodiments, the delivery device, body, delivery part, payload and/or the pharmaceutical composition may include a pharmaceutically acceptable excipient selected from polymer, such as, for example, modified or unmodified water soluble natural polymers such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as Carbopol, carbomer, carbomer homopolymer, carboxyvinyl polymer, polyvinylpyrrolidone (PVP), PVA, PVB, Eudragit L methyl ester, Eudragit L, Eudragit RL, Eudragit RS, Eudragit E, Eudragit S, PHPV, PHA, PCL, PLGA and PLA; and hydrogels made from the polymers or combined polymers mentioned above and or from polymers originated from HEMA, HEEMA, MEMA, MEEMA, EDGMA, NVP, VAc, AA, acrylamide, MAA, HPMA, PEGA, PEGMA, PEGDMA, PEGDA, and PEGDMA.

Gelling Agent

In some embodiments, the delivery device, body, delivery part, payload and/or the pharmaceutical composition may include a pharmaceutically acceptable excipient selected from one or more gelling agents. Examples may be polymers selected from the group consisting of modified or unmodified water soluble natural polymers such as glucomannan, galactan, glucan, polygalacturonic acid, polyxylane, polygalactomannans, polyxyloglycan, arabinogalactan, starch, cellulose, chitosan, alginate, fibrin, collagen, gelatin, amylopectin, pectin including low methylated or methoxylated pectins, dextran; synthetic polymers such as PVA and PVB; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and/or PEGDMA, hydroxypropyl methylcellulose, hydroxypropyl cellulose, methylcellulose, hydroxyethyl cellulose, ethylcellulose, hydroxypropyl methylcellulose phthalate, hydroxypropyl methylcellulose acetate succinate or other cellulose derivates, carboxymethylcellulose sodium, carboxymethylcellulose calcium, carrageenans, guar gum, gellan gum, xanthan gum, tragacanth and arabic gum.

Effervescent Agent

In some embodiments, the delivery device, body, delivery part, payload and/or the pharmaceutical composition may include a pharmaceutically acceptable excipient selected from one or more effervescent agents preferably may be at least one component of an effervescent couple that includes an acid and a base. The effervescent couple may be activated when contacted with water. The water liberates the acid and base and enables the acid and base to react with each other to produce carbon dioxide gas. Examples of useful acids may include water soluble organic acids. Further specific examples may include citric acid, ascorbic acid, glutaric acid, malic acid, malonic acid, adipic acid, clavulanic acid, oxalic acid, tartaric acid, fumaric acid, succinic acid, sodium acid pyrophosphate, sorbic acid, sodium citrate dehydrate, lactic acid, hexamic acid, benzoic acid, etianic acids, disphosphonoic acids and acidic salts and acid anhydrides thereof, and mixtures thereof. Examples of useful acid anhydrides may include citraconic anhydride, glucono-D-lactone, sulphuric acid, hyaluronic acid and succinic anhydride. Examples of useful acid salts may include potassium bitartrate, acid citrate salts, sodium dihydrogen phosphate, disodium dihydrogen phosphate, and combinations thereof. The base preferably is capable of generating carbon dioxide. Examples of useful bases may include water soluble carbonates and bicarbonates. Further specific examples of suitable bases may include sodium bicarbonate such as "EfferSoda", sodium carbonate, sodium sesqui-carbonate, potassium carbonate, potassium bicarbonate, ammonium bicarbonate, calcium carbonate, magnesium carbonate, sodium glycine carbonate, L-lysine carbonate, arginine carbonate, zinc carbonate, and mixtures thereof. In some embodiments the effervescent couple may be selected from citric acid+$NaHCO_3$, Tartaric acid+$NaHCO_3$, Succinic acid+$NaHCO_3$, Malonic acid+$NaHCO_3$, Benzoic acid+$NaHCO_3$, Oxalic acid+$NaHCO_3$, Malic acid+$NaHCO_3$ and Glutaric acid+$NaHCO_3$ Disintegrants In some embodiments the delivery device, body, delivery part, payload and/or the pharmaceutical composition may include a pharmaceutically acceptable excipient selected from one or more disintegrants such as Sodium starch glycolate, Povidone, Sodium alginate, Alginic acid, Calcium alginate, Carboxymethylcellulose calcium, Carboxymethylcellulose sodium, Powdered cellulose, Chitosan, Croscarmellose sodium (Croscarmellose Na), Crospovidone, Cross-linked polyvinylpyrrolidone, Hydroxypropyl starch, Hydroxypropyl cellulose low-substituted, Magnesium aluminium silicate, Methylcellulose, Microcrystalline cellulose, pregelatinized starch, Docusae sodium, Guar gum, Polacrilin potassium.

Stabilizers

In some embodiments, the delivery device, body, delivery part, payload and/or the pharmaceutical composition may include a pharmaceutically acceptable excipient selected from one or more stabilizers such as for example chemical stabilizers may include TPG, for example, in the form of TPGS (Vitamin E Polyehtylene glycol succinate) and BHT, BHA, t-butyl hydroquinone, butylhydroxy toluene, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilizers may include trivalent phosphorous, such as, for example, phosphite, phenolic antioxidants, hydroxylamines, lactones such as substituted benzofuranones, hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-[alpha]-tocopherol, DL-[alpha]-tocopherol, tocopheryl acetate, d-[alpha]-tocopheryl acetate, dl-[alpha]-tocopheryl acetate. However, other anti-oxidative agents known in the art may also be used. Other suitable stabilizers may be selected from, for example, sorbitol glyceryl tricitrate, sucrose octaacetate.

In some embodiments, the delivery device, body, delivery part, payload and/or the pharmaceutical composition may include butylhydoxytoluene and/or TPGS as a stabilizer. In some embodiments, the delivery device, body, delivery part, payload and/or the pharmaceutical composition may include gallic acid and/or ascorbic acid as a stabilizer.

Adhesive Materials

In some embodiments the delivery device, body, delivery part, payload and/or the pharmaceutical composition may include a pharmaceutically acceptable excipient selected from one or more adhesive materials to bring a delivery device close to internal tissue for example the intestinal wall facilitating the interaction of the delivery part. Adhesive materials, for example, such as bioadhesive polymer selected from poly-hydroxyl butyrate, poly(e-caprolactone), polyorthoesters, polyphosphazenes, polycyanoacrylates, polyvinyl acetate, polyethyleneoxide-b-propylene oxide. In some embodiments, the adhesive materials may be selected from bioadhesive materials such as for example, chitosan and carpopol. Enzyme-inhibitors, such as for example, selected from polyacrylic acid, thiomers, polymer-enzyme-inhibitor, polymer-enzyme-inhibitor conjugates, sodium alginate, Chitosan-aurintricarboxylic acid, chitosan-EDTA.

Enhancers

In some embodiments, the delivery device, body, delivery part, payload and/or the pharmaceutical composition may include a pharmaceutically acceptable excipient selected from one or more enhancer such as, for example inhibitors for inhibition of for example metabolic enzymes, efflux pumps or active transport across the gastrointestinal wall with no localized site of enhancement in the gastrointestinal tract, permeation enhancers such as, for example Azone®, cyclodextrins, benzalkonium chloride, phenothiazines, nitric acid donors, menthol, zonula occluden toxin, poly-l-arginines, soybean derivative glucosides, citicholine, a-acid derivatives. Bile salts such as sodium glycocholate, sodium deoxycholate, sodium taurocholate, sodium fusidate, sodium glycodeoxycholate, sodium taurodihydrofusidate. Surfactants such as sodium lauryl sulfate, Brij®-35, lysophospha-tidylcholine, dioctyl sodium sulfosuccinate, laurenth-9, polysorbate-80, polyethylenegly-col-8-laurate, glyceryl monolaurate. Fatty acids and derivatives such as sorbitan laurate, sodium caprate, sucrose palmitate, lauroyl choline, sodium myristate, palmitoyl carnitine. Glycerides such as phospholipids monohexanoin, medium chain glycerides. Chelators such as ethylene diamine tetraacetate (EDTA), disodium EDTA. Salicylates such as salicylic acid, sodium methoxysalicylate, aspirin. Polymers such as chitosan, polycarbophil, sodium carboxymethylcellulose and their derivatives. Capric acid, Choline ester, Palmitoyl carnitine, Sodium lauryl sulfate, Monohexanoin, Ethylene glycol-bis-bis(b-aminoethylether)-N,N,N0,N0-tetraacetic acid, D-a-tocopheryl PEG, succinate, Thiolated polycarbophil, Acylated non-a-amino acids. Cyclopentadecalactone, Sodium N-[8-(2-hydroxylbenzoyl)amino], caprylate (SNAC), 8-(N-2-hydroxy-5-chloro-benzoyl)-aminocaprylic acid (5-CNAC), Medium chain fatty acids, salts, and derivatives, Sodium caprate, modified release formulation, Sodium caprylate suspension in hydrophobic medium with matrix forming polymer, Protease inhibitor and omega 3 fatty acid, Alkylglycosides, Dodecyl-2-N,N-dimethylamino propionate (DDAIP).

Surfactants

In some embodiments, the delivery device, body, delivery part, payload and/or the pharmaceutical composition may include a pharmaceutically acceptable excipient selected from one or more surfactant, for example to enhance and/or to increase tissue permeability for delivery, surfactant may be selected from, for example, Gelucire such as, for example Gelucire 50/13, Gelucire 44/14, Gelucire 50/10, Gelucire 62/05, Sucro-ester 7, Sucro-ester 11, Sucro-ester 15, Polyethoxylated fatty acids such as, for example fatty acid mono- or diesters of polyethylene glycol or mixtures thereof such as, for example mono- or diesters of polyethylene glycol with lauric acid, oleic acid, stearic acid, myristic add, ricinoleic acid, polyethylene glycol such as for example PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, polyethylene glycol glycerol fatty acid esters, i.e. esters like the above-mentioned but in the form of glyceryl esters of the individual fatty acids; glycerol, propylene glycol, ethylene glycol, PEG or sorbitol esters with for example vegetable oils like for example hydrogenated castor oil, almond oil, palm kernel oil, castor oil, apricot kernel oil, olive oil, peanut oil, hydrogenated palm kernel oil and the like, polyglycerized fatty acids like for example polyglycerol stearate, polyglycerol oleate, polyglycerol ricinoleate, polyglycerol linoleate, propylene glycol fatty acid esters such as, for example propylene glycol monolaurate, propylene glycol ricinoleate and the like, mono- and diglycerides like for example glyceryl monooleate, glyceryl dioleae, glyceryl mono- and/or dioleate, glyceryl caprylate, glyceryl caprate etc. sterol and sterol derivatives, polyethylene glycol sorbitan fatty acid esters (PEG-sorbitan fatty acid esters) such as esters of PEG with the various molecular weights indicated above, and the various Tween® series; polyethylene glycol alkyl ethers such as, for example PEG oleyl ether and PEG lauryl ether, sugar esters like for example sucrose monopalmitate and sucrose monolaurate; polyethylene glycol alkyl phenols like for example the Triton® X or N series: polyoxyethylene-polyoxypropylene block copolymers such as, for example, the Pluronic® series, the Synperonic® series, Emkalyx®, Lutrol®, Supronic® etc. The generic term for these polymers is "poloxamers" and relevant examples are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407; sorbitan fatty acid esters like the Span® series or Ariacel® series such as, for example sorbinan monolaurate, sorbitan monopalmitate, sorbitan monooleate, sorbitan monostearate etc.; lower alcohol fatty acid esters like for example oleate, isopropyl myristate, isopropyl palmitate etc.; ionic surfactants including cationic, anionic and zwitterionic surfactants such as, for example fatty acid salts, bile salts, phospholipids, phosphoric acid esters, carboxylates, sulfates and sulfonates etc. and mixtures thereof.

Organic Acids

In some embodiments, the delivery device, body, delivery part, payload and/or the pharmaceutical composition may include a pharmaceutically acceptable excipient selected from one or more suitable organic acids as such, for example, acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, citric acid, tartaric acid or pyruvic acid.

Inorganic Acids

In some embodiments, the delivery device, body, delivery part, payload and/or the pharmaceutical composition may include a pharmaceutically acceptable excipient selected from one or more suitable inorganic acids as such, for example, pyrophosphoric, glycerophosphoric, phosphoric such as ortho and meta phosphoric, boric acid, hydrochloric acid, or sulfuric acid. Examples of suitable inorganic compounds include, for example, aluminum, calcium or kalium.

Organic Bases

In some embodiments, the delivery device, body, delivery part, payload and/or the pharmaceutical composition may include a pharmaceutically acceptable excipient selected from one or more organic bases for example, p-nitrophenol, tromethamine, succinimide, benzenesulfonamide, 2-hydroxy-2cyclohexenone, imidazole, pyrrole, diethanolamine, ethyleneamine tris (hydroxymethyl) aminomethane, hydroxylamine and derivates of amines, sodium citrate, aniline or hydrazine.

Inorganic Bases

In some embodiments the delivery device, body, delivery part, payload and/or the pharmaceutical composition may include a pharmaceutically acceptable excipient selected from one or more inorganic bases, for example, aluminium oxide such as, for example, aluminium oxide trihydrate, alumina, sodium hydroxide, potassium hydroxide, calcium carbonate, ammonium carbonate, ammonium hydroxide or KOH.

Pharmaceutically Acceptable Salts of an Organic Acid

In some embodiments, the delivery device, body, delivery part, payload and/or the pharmaceutical composition may include a pharmaceutically acceptable excipient selected from one or more pharmaceutically acceptable salts of an organic acid, for example, an alkali metal salt or an alkaline earth metal salt such as, for example, sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate or calcium tartrate.

Inorganic Salts

In some embodiments, the delivery device, body, delivery part, payload and/or the pharmaceutical composition may include a pharmaceutically acceptable excipient selected from one or more inorganic salts, for example, sodium chloride, potassium chloride, calcium chloride or magnesium chloride.

A Release Modifier

In some embodiments, the delivery device, body, delivery part, payload and/or the pharmaceutical composition may include a pharmaceutically acceptable excipient selected from one or more release modifiers such as, for example, fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., polyvinyl alcohols, glycerinated gelatine and cocoa butter. Other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Saccharide

In some embodiments, the delivery device, body, delivery part, payload and/or the pharmaceutical composition may include a pharmaceutically acceptable excipient selected from one or more saccharides for example, glucose, ribose, arabinose, xylose, lyxose, xylol, allose, altrose, inosito, glucose, sorbitol, mannose, gulose, glycerol, idose, galactose, talose, mannitol, erythritol, ribitol, xylitol, maltitol, isomalt, lactitol, sucrose, fructose, lactose, dextrin, dextran, amylase or xylan.

Cellulose

In some embodiments, the delivery device, body, delivery part, payload and/or the pharmaceutical composition may include a pharmaceutically acceptable excipient selected from one or more cellulose and/or cellulose derivatives selected from the group consisting of methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxymethylcellulose and hydroxymethylpropylcellulose Production In some embodiments, the delivery device and the pharmaceutical composition may be produced by various methods which are either known per se in the industry or depending upon the desired embodiment and the materials employed in the delivery device or the pharmaceutical composition in question.

In some embodiment, the manufacturing of the delivery device may require shaping of materials for example thermoplastic materials in high precision, detailed in a small size, and may have the ability to contain materials optionally mixed together in specific locations in the delivery device.

In some embodiments, the material for example thermoplastic materials may be able to generate sharp edges, hardness and control that the design may be specifically produced to provide the desired features such as to provide a delivery device with a body to help the flow and the anchoring of the delivery part in the wanted position in the internal tissue as well as a delivery part able to position itself in the internal tissue in a reproducible manner.

In some embodiments, the manufacturing of the delivery device may be scalable to meet demands in a commercial setting.

In some embodiments, the delivery device may contain one material or multiple materials. If the delivery device may contain multiple materials, the materials may optionally be mixed together. More materials in the delivery device may optionally be in one specific location or in multiple specific locations in the delivery device for example in the delivery part, in the connection part and/or the body.

In some embodiments, the delivery part may for example contain an outer layer of one material or multiple materials and an inner core of the same material or another material or multiple materials.

In some embodiments, suitable preparation methods for the delivery device may include laser drilling, milling, cut-out, liquid filling, 3D printing, hot melt-processing and other methods of preparing pharmaceutical compositions. Also, a combination of one or more of the methods may be employed.

In some embodiments, 3D printing and injection molding may be suitable technologies to address these demands described herein. Both 3D printing and injection molding technology may allow manufacturing such delivery devices in small size of high precision and detail, and may have the ability to contain materials and mixtures of materials in specific locations of the delivery device.

3D Printing

In some embodiments, the delivery device may be prepared by 3D printing.

In some embodiments, 3D printing, which is an additive manufacturing technology where small additions may be printed in layers building a desired shape and small well-defined geometries may be printed for various purposes.

Hot Melt Extrusion

In some embodiments, the delivery device may be prepared by hot melt-processing.

In some embodiments, the manufacturing of the delivery device may also happen through a hot melt extrusion procedure, where the heating of material happens at a first step and a certain defined amount may then be separated from the mass and transferred to an equipment responsible for shaping the material in a desired geometry.

In some embodiments, the delivery device may be prepared by, for example; 1, 2 or multiple component extrusion.

Injection Molding

In some embodiments, the delivery device is prepared by injection molding.

In some embodiments, a number of low permeable active drug substances for example peptides have been injection molded into tablets intended for oral delivery and the technology has shown that despite the use of heat in the process the peptide remains stable and active both in primary, secondary and tertiary structures indicating that the materials for example polymers used in injection molding may have a stabilizing effect on the otherwise labile active drug substances. In some embodiments, good stability may be achievable also because the active drug substance as long as it may not be released from the delivery device may be imbedded in a protective polymer environment ensuring stability thought the passage of for example the gastrointestinal tract until the moment of release and permeation of the active drug substance for example in the gastrointestinal tissue.

In some embodiments, the delivery device may be prepared by 1, 2 or multiple component injection molding.

In some embodiments, where a preparation may be needed in order to make either of the following parts, the pharmaceutical composition, the delivery device, the body, the connection part, the delivery part and/or the payload either before, during or after the above-mentioned preparation steps, the preparation may also comprise separate steps such as for example wet granulation, dry granulation, melt granulation, pelletizing, curing, spray coating, electrostatic coating, dip coating, assembly, separate filling, injection molding, hot melt extrusion, 3D printing, milling, laser drilling or other forms of preparation methods.

In some embodiments, the payload may be prepared by load an accurate amount of the polymer into a mixer followed by an accurate amount of the active drug substance and/or plasticizer and/or other pharmaceutically acceptable excipients(s), liquid(s) if any. The mixing may then be performed to secure a homogeneous blend. In some embodiments, to improve the flowability the solid payload may then be granulated by for example dry granulation (such as roller compaction), melt granulation or wet granulation optionally with a suitable binder. In some embodiments, the payload may be dried and then fed into an injection molding machine for example Krauss Maffei and molded into the cavity in the delivery part. In some embodiments, the payload may be transferred to a filling station and applied into the cavity in the delivery part in a fixed position. Heating may optionally be applied when filling. The same operation may be applied for a semi-solid payload or a liquid payload.

In some embodiments, the delivery device, body, connection part and the delivery part may be prepared by load an accurate amount of the polymer into a mixer followed by an accurate amount of the active drug substance and/or plasticizer and/or other pharmaceutically acceptable excipients(s), liquid(s) if any. The mixing may then be performed to secure a homogeneous blend. In some embodiments, to improve the flowability, the blend may be granulated by for example dry granulation (such as roller compaction), melt granulation or wet granulation optionally with a suitable binder. In some embodiments, the blend may be dried and then fed into an injection molding machine for example Krauss Maffei and molded into the delivery device, body, connection part and the delivery part in one process.

In some embodiments, the final delivery device may be prepared according to different methods. In some embodiments, the body, connection part and the delivery part may be molded individually followed by a manually incorporation of the molded delivery part and/or connection part into the body. The payload may either be added before or after this step. In some embodiments, the body, connection part and delivery part may be manufactured/molded in one process step and the payload may be added directly into the delivery part in a second processing step, optionally followed by a third processing step where the payload may be sealed.

In some embodiment, the body, connection part and delivery part may be of the same composition and manufactured/molded in the same process. In some embodiments, the body, connection part and delivery part may be of different compositions where the body may be molded in a first step, the connection part may be molded in a second step and the delivery part may be molded in a third step and optionally by a manually incorporation of the molded delivery part and connection part into the body. In some embodiments, the connection part may be hollow or of a different composition than the composition of the body and/or delivery part.

In some embodiments, the pharmaceutical composition may be produced by methods that may be relatively simple and inexpensive.

In some embodiments, the pharmaceutical composition may be prepared by conventional tablet compression.

In some embodiments, the pharmaceutical composition may be prepared by conventional capsule filling.

In some embodiments, the pharmaceutical composition may be prepared by conventional suppository molding.

Method of Action

In some embodiments, bowel movements may comprise the physical force to move the delivery device in the gastrointestinal tract and the physical force needed to position the delivery part into the intestinal wall to release the payload in the intestinal tissue.

In some embodiments, the transport across the gastrointestinal wall may be localized at the site of attachment in the gastrointestinal tract and consequently this will be the site of release of the active drug substance.

In some embodiments, the delivery device may be delivered in the stomach for delivery in the gastric wall to release the payload in the gastric tissue. In some embodiments, the delivery device may be delivered in the intestine for delivery in the intestinal wall to release the payload in the intestinal tissue.

In the present context, bowel movements may be the peristaltic and fluid mucous flow in the gastrointestinal tracts and responsible for a directional flow of material in the lumen of the gastrointestinal tract. The peristaltic contractions may be initiated in the upper gastrointestinal tract and may move downward aiding the material to move downwards in the gastrointestinal tract. The contractions surround the material consisting of what has been swallowed. Materials may for example be in the form of food, tablet, capsules and/or drinks.

In some embodiments, bowel movements may provide a dynamic environment with a motion, which may ensure that a swallowed delivery device may not be able to pass through the gastrointestinal tract without being near the gastrointestinal wall.

In some embodiments, bowel movements may comprise the physical force to move the delivery device in the gastrointestinal tract and the physical force needed for the delivery part to position itself in the gastrointestinal wall to release the payload in the gastrointestinal tissue.

Method of Delivery

In some embodiments, the pharmaceutical composition may be prepared for delivery of the delivery device in the mouth (for example buccal, sublingual), orally, rectally or vaginally.

In some embodiments, the pharmaceutical composition may be targeted to deliver the delivery device at any site in the gastrointestinal tract to release the payload in the gastrointestinal tissue. The delivery device may be delivered in the mouth for delivery sublingual or buccal, in stomach for delivery into the gastric wall to release the payload in the gastric tissue, the delivery device may be delivered in the intestine for delivery into the intestinal wall to release the payload in the intestinal tissue or the delivery device may be delivered rectal for delivery into the rectal wall to release the payload in the rectal tissue.

In some embodiments, the pharmaceutical composition may be prepared for oral intake, such as for example in the mouth (for example buccal, sublingual) or orally. In some embodiments, the pharmaceutical composition may be prepared for oral intake by swallowing. Accordingly, the size of the pharmaceutical composition may be in a range that allows for oral intake by swallowing.

In some embodiments, the pharmaceutical composition may be prepared for rectal or vaginal administration. In some embodiments, the delivery device may be contained in for example a suppository to allow delivery of the delivery device.

In some embodiment, the pharmaceutical composition may be targeted to deliver the delivery device in vagina for delivery into the vaginal wall to release the payload in the vaginal tissue.

Administration

In some embodiments, the delivery device may be prepared for administration to an individual in need thereof. Said individual may be a subject. Said the individual may be a mammal, and in some embodiments the individual is a human being.

In some embodiments, a delivery device may be dimensioned and constructed to carry a payload and the payload may be delivered in an internal tissue of a subject after interaction with a delivery part protruding from the delivery device surface. In some embodiments, delivery devices and methods provided herein may be useful, in particular, in delivery of a variety of macromolecular, potent therapeutic agents, which may suffer from poor permeability across biological membranes/tissues. In some embodiments, delivery devices and methods provided herein may be useful, in particular, in delivery of a variety of biologics such as, for example, monoclonal antibodies, single chain antibodies, aptamer, enzymes, peptides, growth factors, hormones, antigens, fusion proteins, cytokines, therapeutic enzymes, recombinant vaccines, blood factors, and/or anticoagulants.

In some embodiments, internal tissues of a subject, such as a mammal (for example, human), may include any internal tissues in vagina and in the gastrointestinal (GI) tract, rectum, large or small intestine Jejunum, duodenum), stomach, esophagus, buccal or mouth tissue. As an example, a mucous membrane, including buccal mucosa, esophageal mucosa, gastric mucosa, intestinal mucosa, oral mucosa, rectal mucosa, vaginal mucosa etc., may be an internal tissue.

In some embodiments, the delivery device may be used for oral administration.

In some embodiments, the pharmaceutical composition may be designed for oral administration. For example, the pharmaceutical compositions may be produced as capsules, for oral intake by swallowing one or more intact capsules of the pharmaceutical composition.

In some embodiments, the pharmaceutical composition may be designed for oral administration. For example, the pharmaceutical compositions may be produced as tablets, for oral intake by swallowing one or more intact tablets of the pharmaceutical composition.

In some embodiments, the pharmaceutical composition may be designed for rectal or vaginal administration. For example, the pharmaceutical compositions may be produced as suppository.

In some embodiments, the pharmaceutical composition may comprise one active drug substance or more than one different active drug substances.

In some embodiments, the pharmaceutical composition may contain one delivery device or more than one delivery devices.

In some embodiments, the delivery device may comprise one active drug substance or more than one different active drug substance.

In some embodiments, the delivery device may contain an active drug substance. Due to the possibility of controlling the release rate of the active drug substance, the delivery device may be administered 1-6 times a day, such as 1-5 times daily, including 1-4 times, 1-3 times, 1-2 times or twice or once daily.

In some embodiments, the delivery device may contain an active drug substance. Due to the type of the active drug substance, the delivery device may be administered 1-6 times a day, such as 1-5 times daily, including 1-4 times, 1-3 times, 1-2 times or twice or once daily.

In some embodiments, the delivery device may contain an active drug substance. Due to the type of the active drug substance, the delivery device may be administered 1-8 times monthly, such as 1-6 times monthly, including 1-4 times, 1-2 times or twice or once monthly.

In some embodiments, the delivery device may contain an active drug substance. Due to the type of the active drug substance, the delivery device may be administered every 6 months or every year.

In some embodiments, the delivery device may be prepared for delivery of the desired dosage of active drug substance. The dosage may be dependent on the individual to whom the delivery device may be administered and the active drug substance.

In some embodiments, the dosage for each administration, wherein dosages may be in the range of 1 µg to 1000 mg, such as in the range of 1 µg to 750 mg, for example in the range of 1 µg to 500 mg, such as in the range of 1 µg to 250 mg, for example in the range of 1 µg to 100 mg, such as in the range of 1 µg to 90 mg, for example in the range of 1 µg to 80 mg, such as in the range of 1 µg to 70 mg, for example in the range of 1 µg to 60 mg, such as in the range of 1 µg to 50 mg, for example in the range of 1 µg to 40 mg, such as in the range of 1 µg to 30 mg, for example in the range of 1 µg to 20 mg, such as in the range of 1 µg to 10 mg, for example in the range of 1 µg to 9 mg, such as in the range of 1 µg to 8 mg, for example in the range of 1 µg to 7 mg, such as in the range of 1 µg to 6 mg, for example in the range of 1 µg to 5 mg, such as in the range of 1 µg to 4 mg, for example in the range of 1 µg to 3 mg such as in the range of 1 µg to 2 mg, for example in the range of 1 µg to 1 mg.

In some embodiments, the above-mentioned dosages may be in particular relevant when the individual in need of treatment is a human being, such as an adult, child, adolescent human being.

General

All patent and non-patent references cited in the application are hereby incorporated by reference in their entirety.

It should be understood that any feature and/or aspect discussed above in connections with the compounds according to the disclosure apply by analogy to the methods described herein.

It should be understood that any feature and/or aspect discussed above in connections with the term "internal surface" apply by analogy to the term "internal tissue".

In order for the present disclosure to be more readily understood, certain terms are defined below. Additional definitions for the following terms and other term are set forth throughout the application.

In the present disclosure, when referring to an angle between two axes and/or an angle between an axis and a direction, the angle may be the smallest angle between the axes or the axis and the direction.

In the present disclosure, longitudinal axis may be defined as direction of a straight line between two points on the surface of the delivery device having the largest distance there between.

In this application, the use of singular form "a", "an" and "the" include plural references unless the context clearly dictates otherwise.

As used in this application, the use of "or" means "and/or" unless stated otherwise.

As used herein, the term "comprise" and variations of the term such as "comprising" or "comprises" is intended to mean that the compositions and methods include the recited elements, but not excluding others.

As used in this application, the terms "about" and "approximately" are used as equivalent.

The following figures and examples are provided below to illustrate the present disclosure. They are intended to be illustrative and are not to be construed as limiting in any way.

DETAILED DESCRIPTION OF THE FIGURES

FIG. 1

FIG. 1 shows an exemplary delivery device. The delivery device 2 has a first end 4 and a second end 6 with a longitudinal axis X_L there between, and comprising a body 8 and a delivery part 10. The body 8 extends along a body axis X_B from a first body end 12 to a second body end 14 and having a body surface 16. The delivery part comprises a first attachment part 18 having a first distal end 20 configured to position itself in an internal surface of a subject. The first attachment part 18 extends along a first axis X1, wherein a first angle V1 between the first axis X1 and the longitudinal axis X_L is less than 75 degrees. The first distal end 20 is arranged at a distance D1 from the body surface 16, wherein the distance D1 is about 1.5 mm. The first attachment part has a length L1 of about 5 mm. The first attachment part 18 comprises a first bevel surface 22 forming a cutting edge 24 extending from the first distal end 20. The first bevel surface faces away from the body surface 16 and has a first bevel normal 26 forming a first primary bevel angle VB1_1 with the first axis larger than 20 degrees. The first bevel normal 26 forms a first secondary angle VB1_2 with the longitudinal axis X_L larger than 60 degrees, for example about 85 degrees as illustrated.

The first distal end 20 of the first attachment part 18 is arranged between the first body end 12 and the second body end 14 of the body 8. The body 8 is made of a material comprising one or more thermoplastic polymers, the delivery part 10 is made of a material comprising one or more thermoplastic polymers.

The delivery device 2 comprises a connection part 30 arranged between the body 8 and the delivery part 10. The connection part 30 extends along a connection axis X_C. The connection axis X_C forms a first connection angle VC1 with the longitudinal axis X_L. The connection axis X_C forms a second connection angle VC2 with the first axis.

FIG. 2

Figure 2:
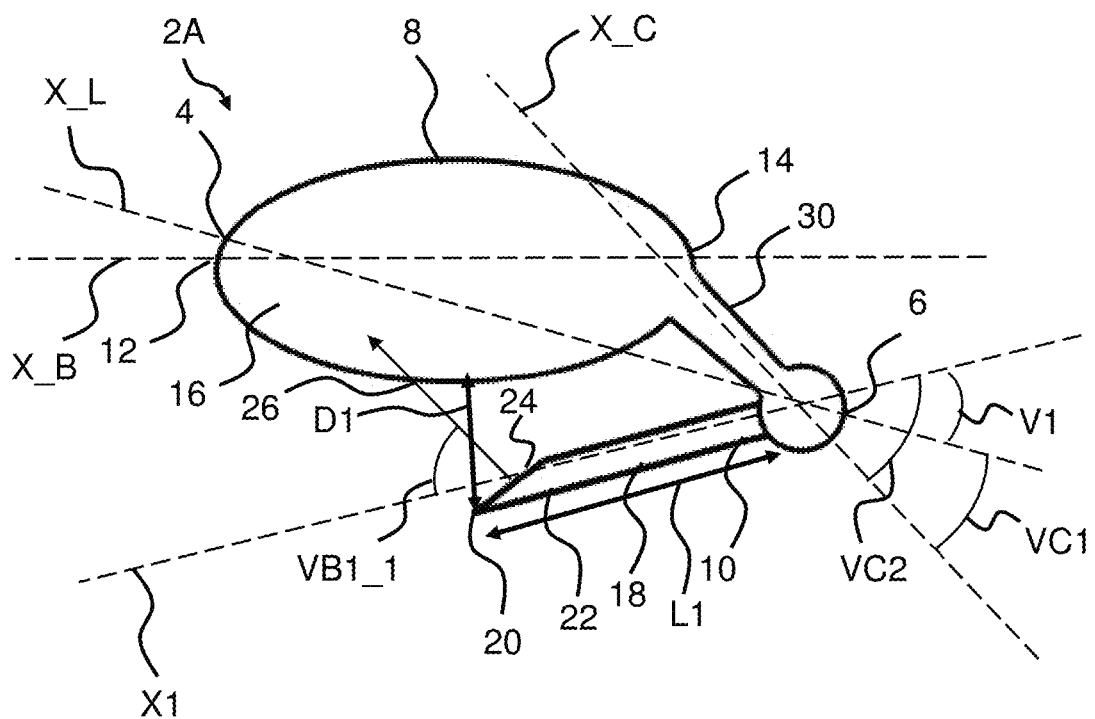
FIG. 2—schematically illustrates an exemplary delivery device

FIG. 2 shows an exemplary delivery device. The delivery device 2A has a first bevel surface 22 facing the body surface 16 with a first secondary bevel angle less than 45 degrees.

FIG. 3

Figure 3:
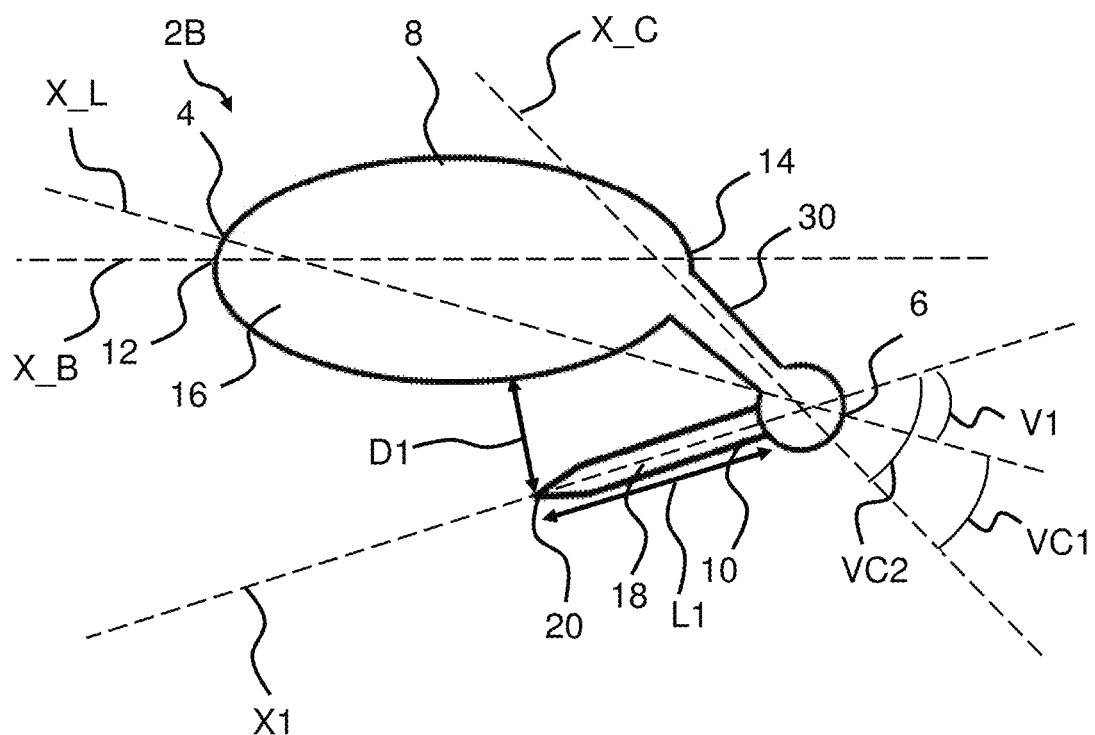
FIG. 3—schematically illustrates an exemplary delivery device

FIG. 3 shows an exemplary delivery device. The delivery device 2B has a conical tip at the first distal end 20 of the first attachment part 18.

FIG. 4

Figure 4:
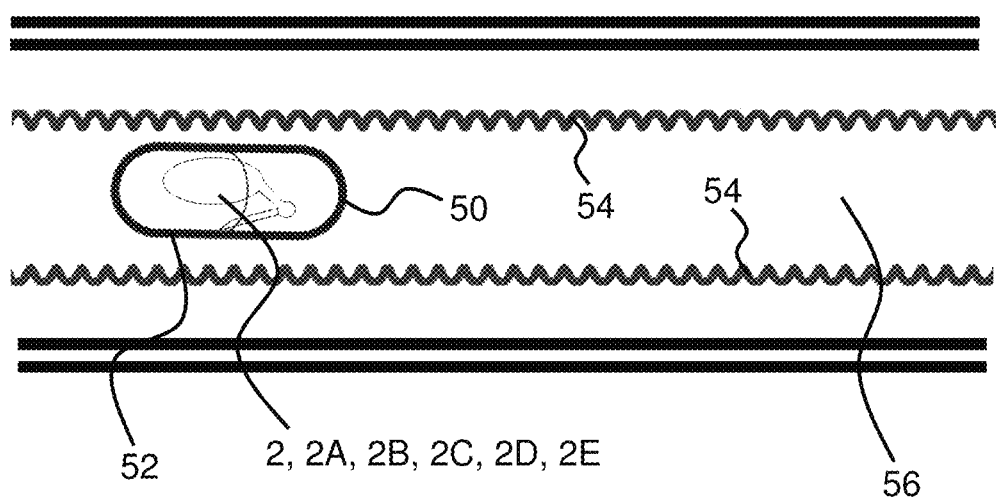
FIG. 4—illustrates a pharmaceutical composition in a gastrointestinal environment FIG. 5—illustrates a delivery device in a gastrointestinal environment FIG. 6—is a view of an exemplary delivery part FIG. 7—is a cross-sectional view of the delivery part of FIG. 6

FIG. 4 illustrates a composition in a gastrointestinal environment. The composition 50 comprise a carrier 52 and a delivery device 2A. Peristaltic movements of the gastrointestinal wall 54 moves the composition 50 in the gastrointestinal lumen 56, see also FIG. 5

FIG. 5

FIG. 5 illustrates the delivery device 2A in the gastrointestinal environment at a later stage. The carrier 52 has been dissolved and the delivery device 2A is pressed against the gastrointestinal wall 54 by the peristaltic movements of the gastrointestinal wall 54. The first distal end of the delivery device 2A has position itself in the inner surface of the gastrointestinal wall 54 to deliver an active drug substance to the gastrointestinal wall 54.

FIG. 6

Figure 6:
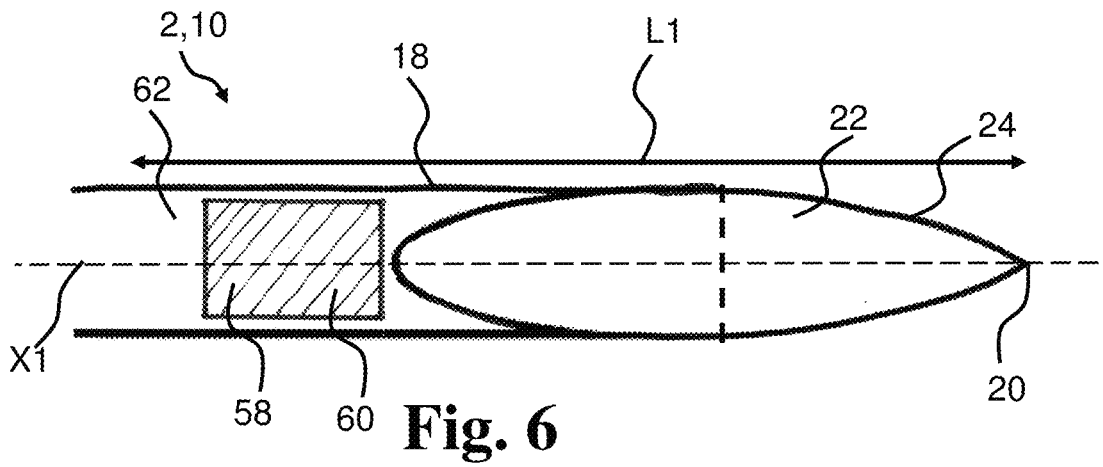

FIG. 6 is a first view of an exemplary delivery part. The delivery part 10 comprises a first attachment part 18 having a first distal end 20 configured to penetrate an internal surface of a subject. The first attachment part 18 extends along a first axis X1. The first attachment part has a length L1 of about 5 mm. The first attachment part 18 comprises a first bevel surface 22 forming a cutting edge 24 extending from the first distal end 20. The first bevel surface 22 has a first bevel normal 26 forming a first primary bevel angle VB1_1 with the first axis larger X1 than 20 degrees. The first bevel surface 22 is at least partly concave.

The exemplary first attachment part 10 defines a first cavity 58 for accommodating a payload comprising an active drug substance. The first cavity 58 may form one or more openings including a first opening 60 in the outer surface 62 of the first attachment part 10. The one or more openings in the first attachment part facilitates release of the active drug substance.

FIG. 7

Figure 7:
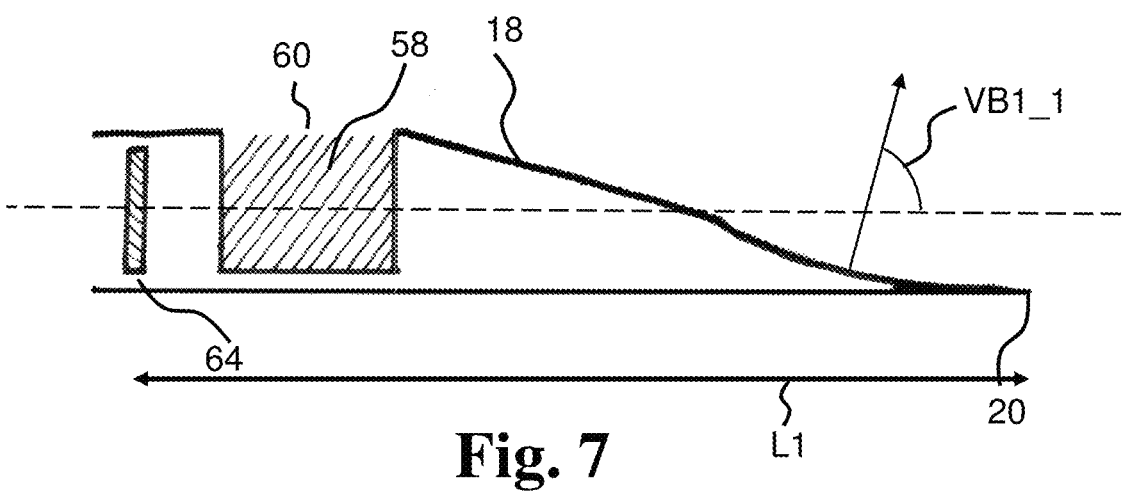

FIG. 7 is a cross-sectional view of delivery part in FIG. 6. The delivery device comprises a separation part 64 arranged between the body (not shown) and the first attachment part 18. The separation part 64 is configured to break upon attachment of the first attachment part 18 to the internal surface for separating the body and the first attachment part 18 upon attachment of the first attachment part.

FIG. 8

Figure 8:
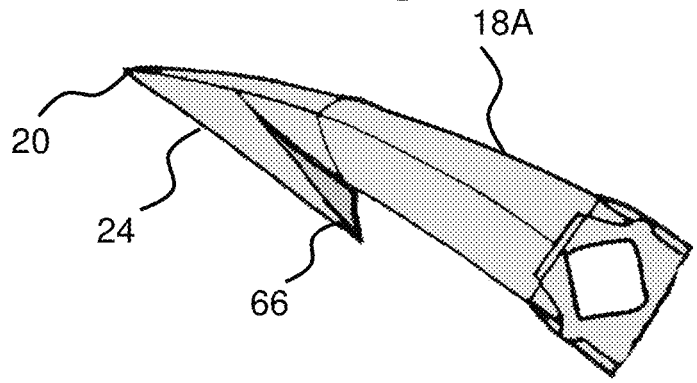
FIG. 8—is a view of an exemplary attachment part

FIG. 8 is a perspective view of an exemplary attachment part of a delivery device according to the present disclosure. The attachment part 18A comprises a first barb element 66 assistive in keeping the attachment part 18A secured or attached to the internal surface upon penetration of the internal surface. The attachment part 18A is curved and comprises a first bend within 2 mm from the first distal end 20 such that the first distal end 20 points in a first direction (not shown) forming a first primary bend angle with the longitudinal axis and/or a first secondary bend angle with the first axis.

FIG. 9

Figure 9:
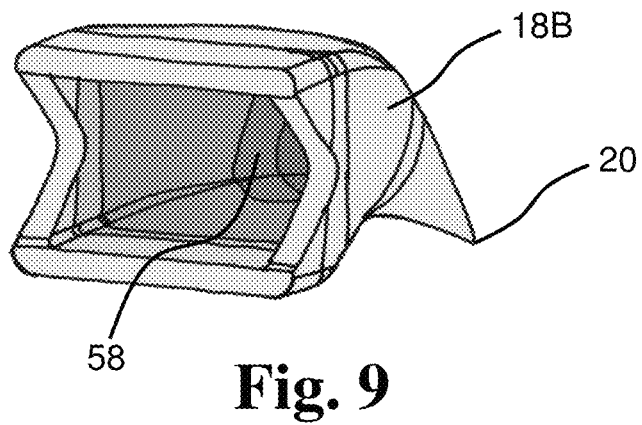
FIG. 9—is a view of an exemplary attachment part

FIG. 9 is a perspective view of an exemplary attachment part of a delivery device according to the present disclosure. The attachment part 18B comprises a first cavity 58 extending from a distance less than 2.0 mm from the first distal end 20 assistive in keeping the attachment part 18A secured or attached to the internal surface upon penetration of the internal surface. The attachment part 18A is curved and comprises a first bend within 2 mm from the first distal end 20.

FIG. 10

Figure 10:
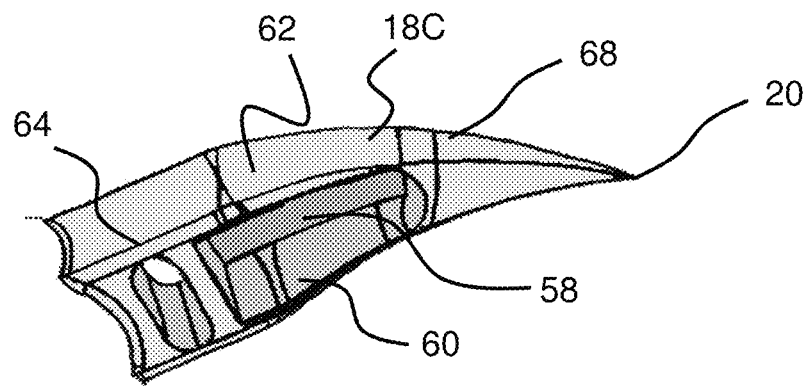
FIG. 10—is a view of an exemplary attachment part of a delivery device

FIG. 10 is a perspective view of a part of an exemplary delivery device according to the present disclosure. The delivery device comprises a first attachment part 18C comprising a first cavity 58 extending from a first opening 60 in the outer surface 62 of the first attachment part. The first attachment part 18C is curved and comprises a first bend 68 within 2 mm from the first distal end 20. A separation part 64 is formed by a through-going bore in the delivery device.

FIG. 11

Figure 11:
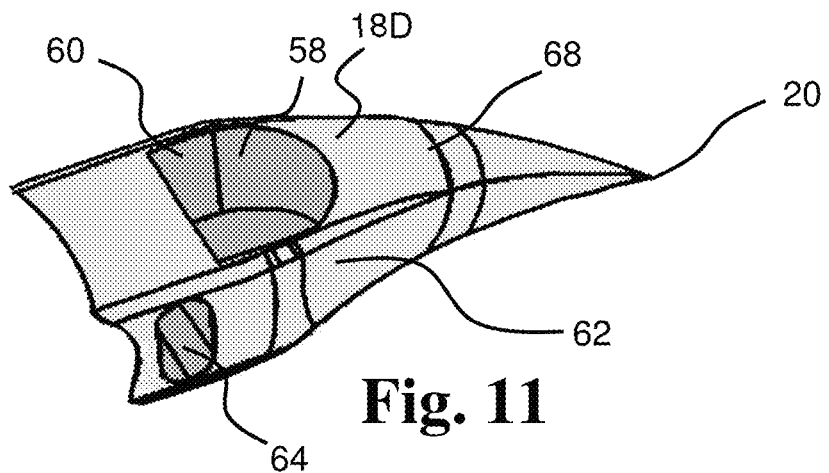
FIG. 11—is a view of an exemplary attachment part of a delivery device

FIG. 11 is a perspective view of a part of an exemplary delivery device according to the present disclosure. The delivery device comprises a first attachment part 18D comprising a first cavity 58 extending from a first opening 60 in the outer surface 62 of the first attachment part. The first attachment part 18D is curved and comprises a first bend 68 within 2 mm from the first distal end 20. A separation part 64 is formed by a through-going bore in the delivery device.

FIG. 17

Figure 17:
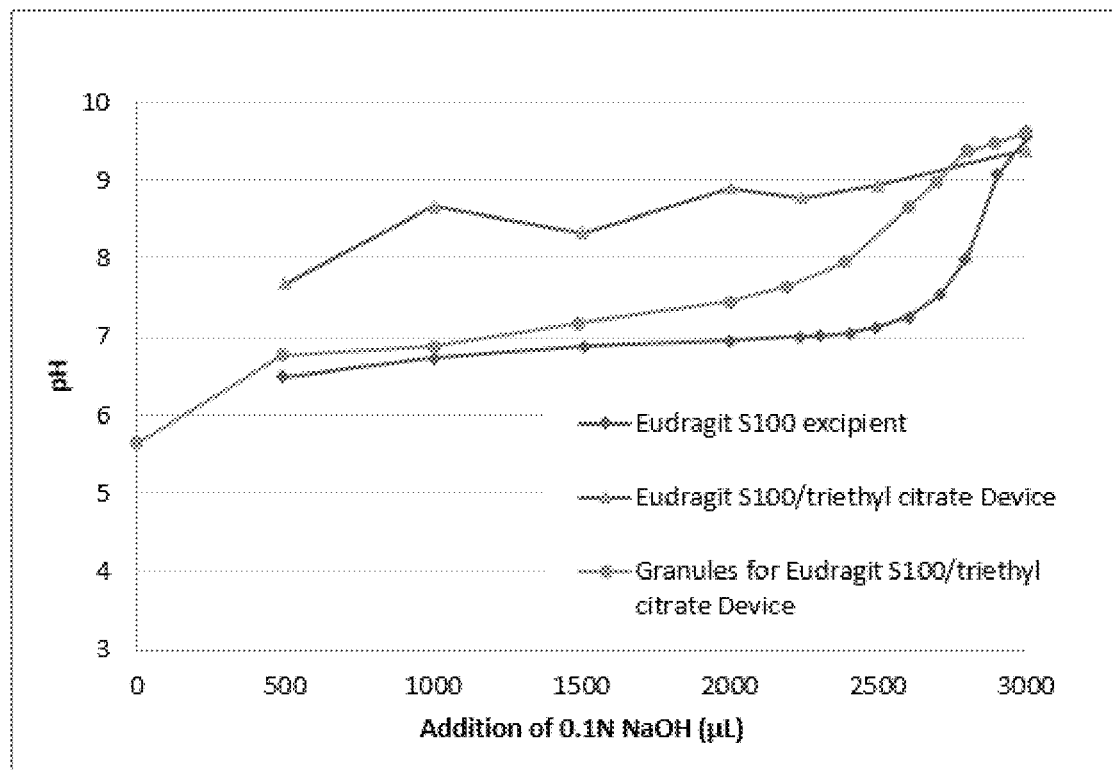
FIG. 17—is a view of pH/dissolution profile of Eudragit

FIG. 17 is a view and characterization of the pH at which Eudragit S100 dissolves and the amount of 0.1N needed in saline (0.9 NaCl w/v %) to dissolve 75 mg of the Eudragit S100 polymer either as the Eudragit S100 excipient, as granules made from Eudragit 5100/triethyl citrate, or as ground Eudragit 5100/triethyl citrate device as mentioned in example 6.

FIG. 18

Figure 18:
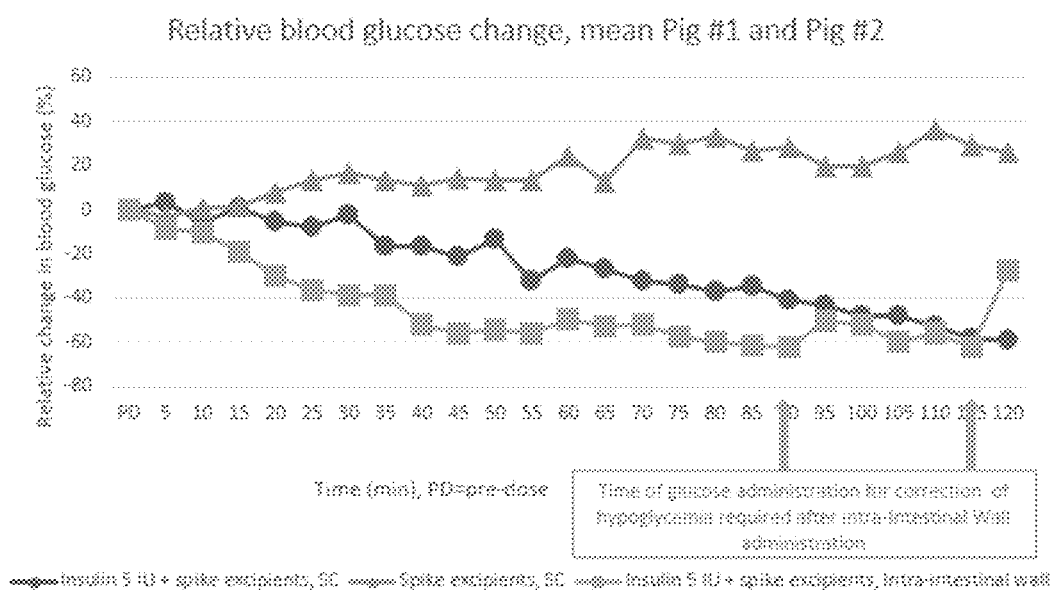
FIG. 18—is a view of blood glucose values

FIG. 18 is a view of the mean results of Pig #1 and Pig #2; blood glucose values for each composition and route of administration as mentioned in example 7.

Parameters for exemplary delivery devices A-I are set out in Table 1.

TABLE 1

|  | A | B | C | D | E | F | G | H | I |
| --- | --- | --- | --- | --- | --- | --- | --- | --- | --- |
| V1 (°) | 20-40 | 30-50 | 60-75 | 0-20 | 0-30 | 20-40 | 30-50 | 60-75 | 0-30 |
| D1 (mm) | 0.5-2 | 8-10 | 4-6 | 0.5-2 | 1-3 | 3-5 | 6-8 | 10-20 | 0.5-2 |
| L1 (mm) | 3-5 | 2-3 | 6-8 | 3-5 | 2-5 | 15-20 | 12-18 | 15-20 | 15-30 |

FIG. 12

Figure 12:
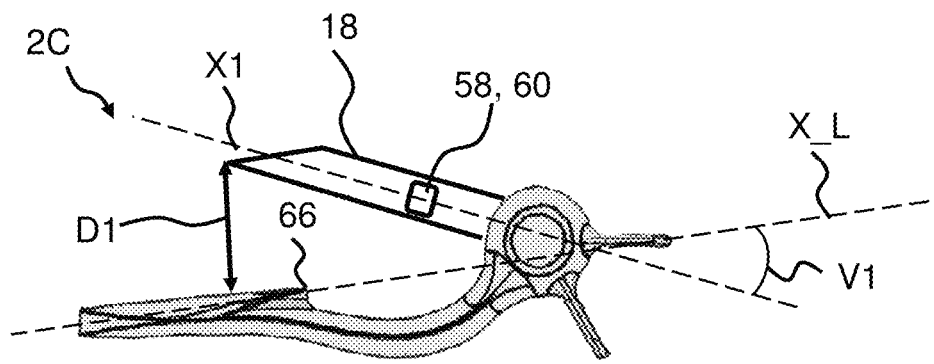
FIG. 12—is a view of an exemplary delivery device

FIG. 12 is a view of an exemplary delivery device 2C according to the present disclosure. The delivery device 2C comprises a first attachment part 18 comprising a first cavity 58 extending from a first opening 60 in the outer surface of the first attachment part. The first cavity accommodates a payload comprising an active drug substance.

FIG. 13

Figure 13:
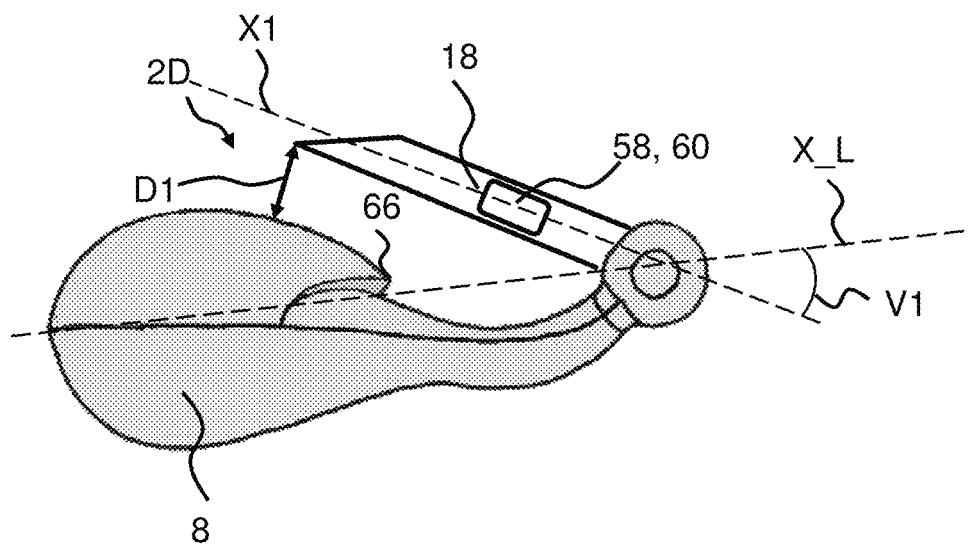
FIG. 13—is a view of an exemplary delivery device

FIG. 13 is a view of an exemplary delivery device 2D according to the present disclosure. The delivery device 2D comprises a first attachment part 18 comprising a first cavity 58 extending from a first opening 60 in the outer surface of the first attachment part 18. The first cavity 58 accommodates a payload comprising an active drug substance. The body 8 is drop-shaped and comprises a first barb element 66 assistive in keeping the delivery device 2D secured or attached to the internal surface upon penetration of the internal surface.

FIG. 14

Figure 14:
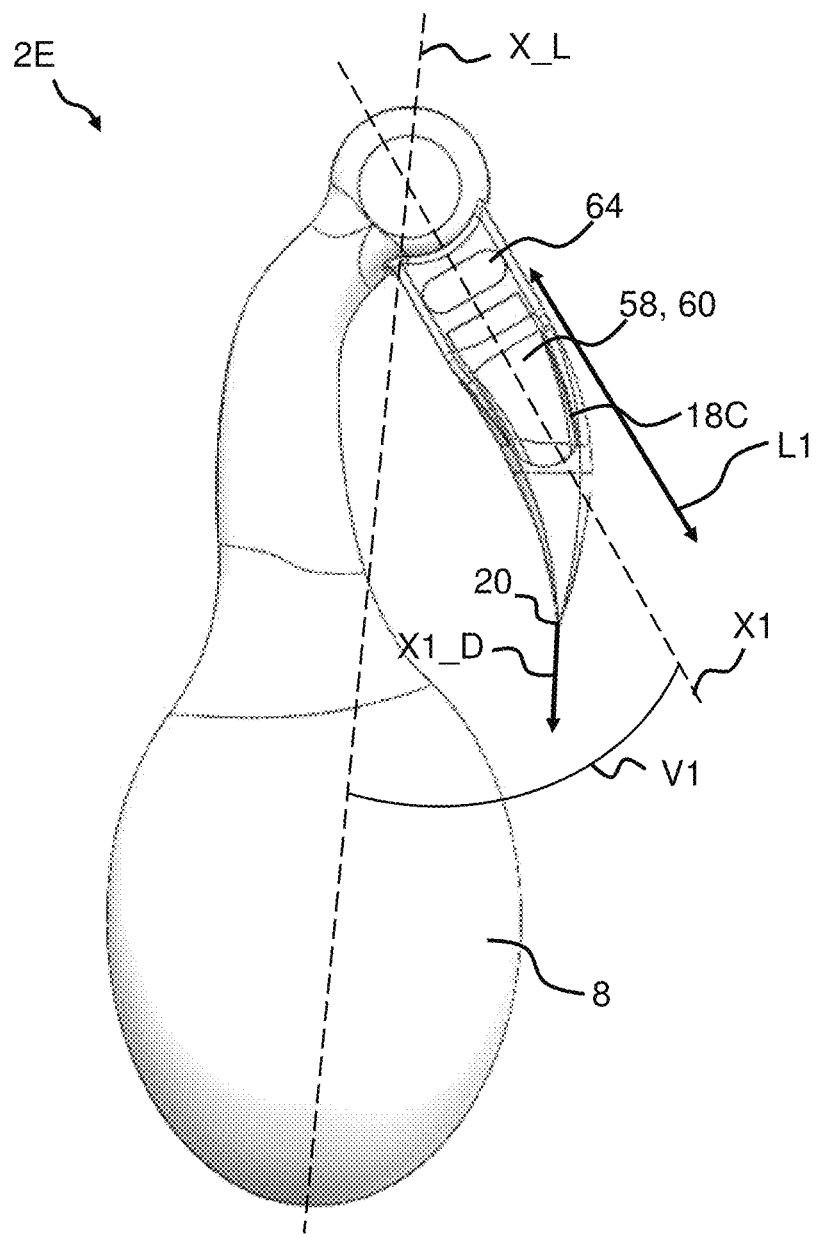
FIG. 14—is a view of an exemplary delivery device

FIG. 14 is a view of an exemplary delivery device 2E according to the present disclosure. The delivery device 2E comprises a first attachment part 18 comprising a first cavity 58 extending from a first opening 60 in the outer surface of the first attachment part 18. The first cavity 58 accommodates a payload comprising an active drug substance. The first distal end 20 points in a first direction X1_D forming a first primary bend angle with the longitudinal axis in the range from 0 to 20 degrees. The first direction X1_D forms a first secondary bend angle with the first axis X1 less than 60 degrees.

FIG. 15

Figure 15:
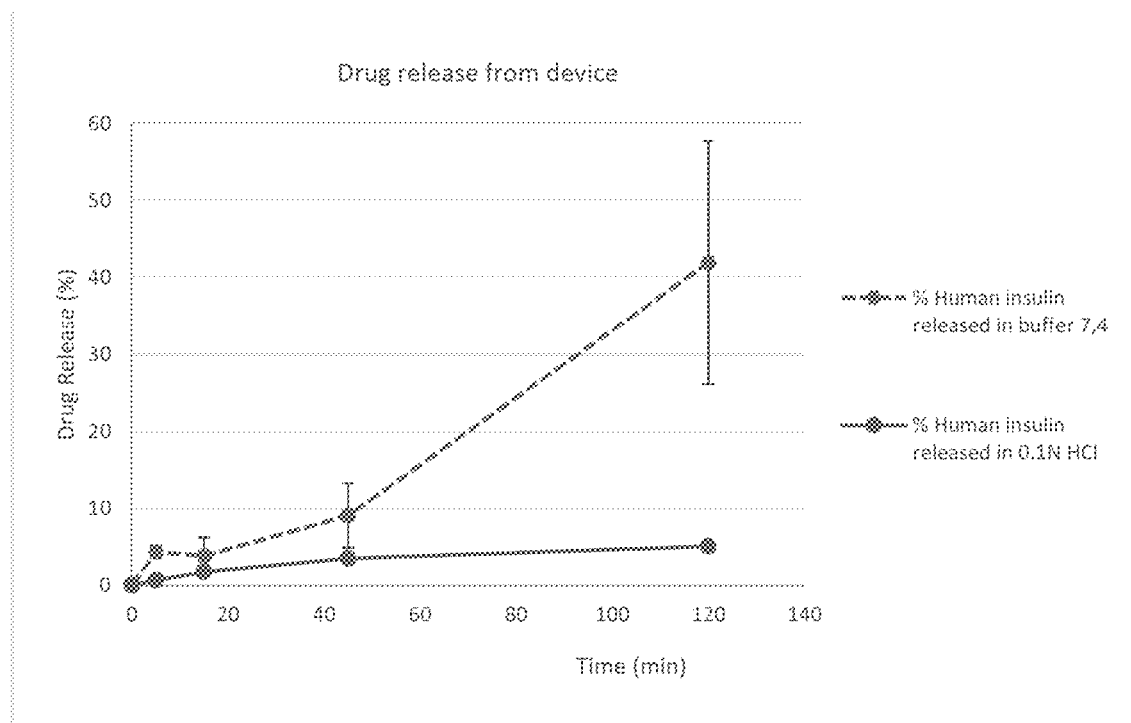
FIG. 15—is a view of a dissolution profile of Insulin

FIG. 15 is a view of the release of human insulin from the delivery device mentioned in example 3. Dissolution profile in either a phosphate buffer solution pH 7.4 or a dilute hydrochloric acid 0.1N dissolution medium is shown.

FIG. 16

Figure 16:
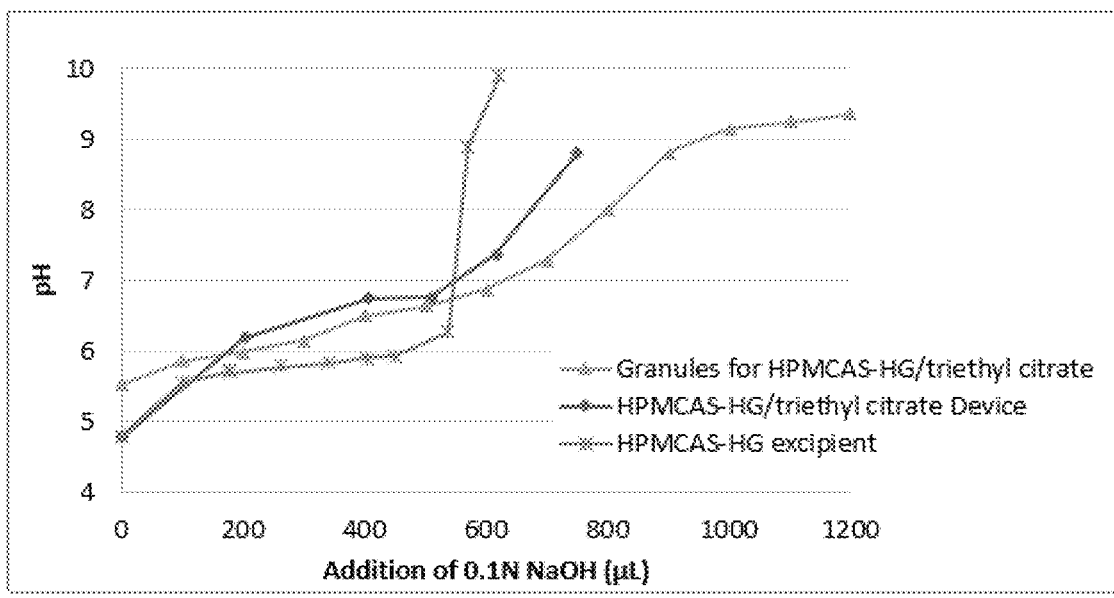
FIG. 16—is a view of pH/dissolution profile of HPMCAS

FIG. 16 is a view and characterization of the pH at which HPMCAS-HG dissolves and the amount of 0.1N needed in saline (0.9 NaCl w/v %) to dissolve 75 mg HPMCAS-HG polymer either as the HPMCAS-HG excipient, as granules made from HPMCAS-HG/triethyl citrate, or as ground HPMCAS-HG/triethyl citrate device as mentioned in example 5.

FIG. 19

Figure 19:
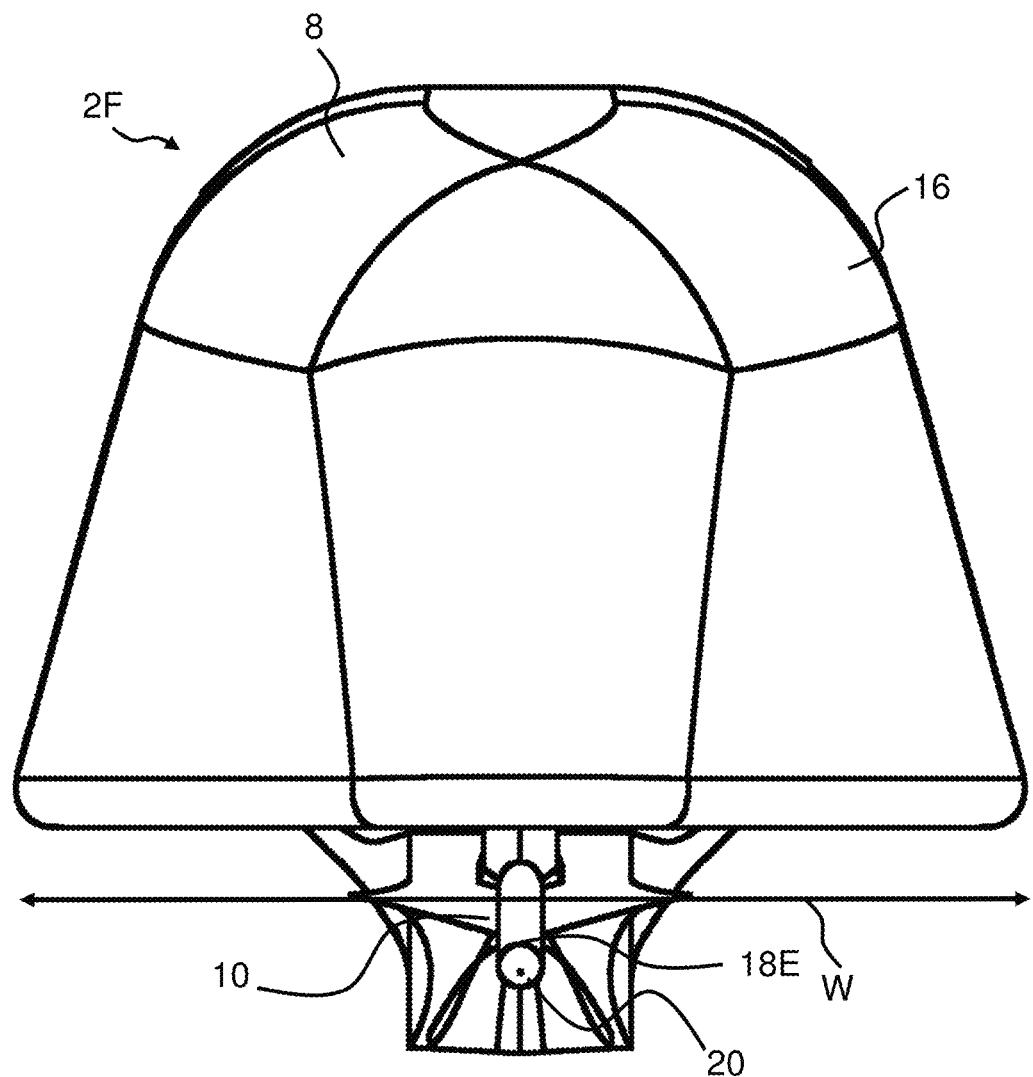
FIG. 19—is a view of an exemplary delivery device

FIG. 19 shows a first end view of an exemplary delivery device 2F. The delivery device 2F has a maximum width W in the range from 2 mm to 12 mm, such as about 7 mm. The delivery device 2F comprises a body 8 and a delivery part 10. The body 8 has a body surface 16. The delivery part 10 comprises a first attachment part 18E having a first distal end 20 configured to position itself in an internal surface of a subject. The delivery device 2F has a conical tip at the first distal end 20 of the first attachment part 18E.

FIG. 20

FIG. 20 shows a side view of the delivery part 2F. The first attachment part 18E extends along a first axis X1, wherein a first angle V1 between the first axis X1 and the longitudinal axis X_L is less than 75 degrees. The first distal end 20 is arranged at a distance D1 from the body surface 16, wherein the distance D1 is in the range from 0.5 mm to 5.0 mm such as about 1.3 mm. The first attachment part 18E has a length L1 of about 5.7 mm. The first attachment part 18E comprises a first bevel surface 22 forming a cutting edge 24. The first bevel surface 22 faces away from the body surface 16. The delivery part 10 comprises a first barb element 66 assistive in keeping the delivery device 2F secured or attached to the internal surface upon penetration of the internal surface.

FIG. 21

Figure 21:
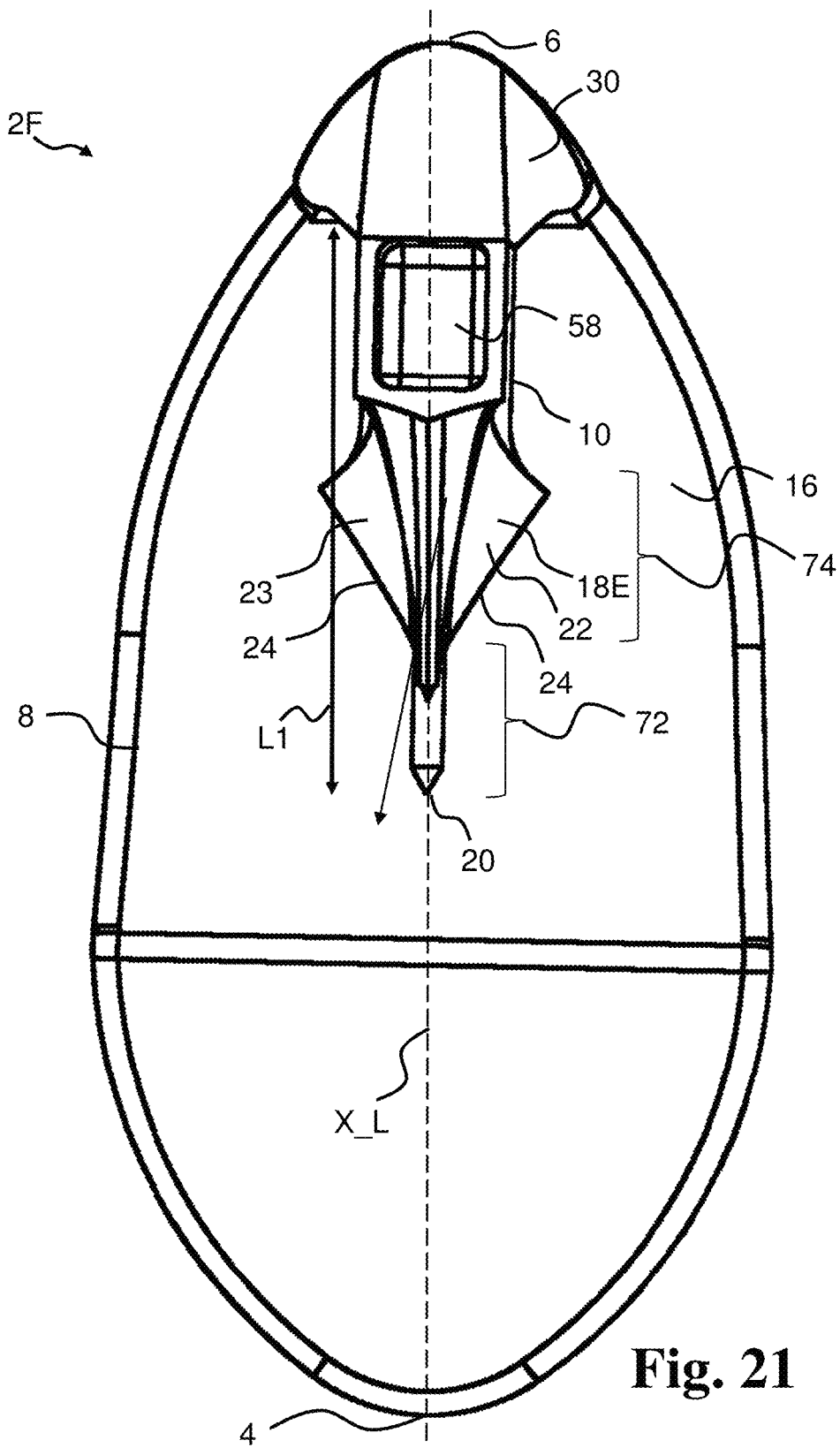
FIG. 21—is a view of an exemplary delivery device

FIG. 21 shows a side view of the delivery part 2F. The first attachment part 18E comprises second bevel surface 23 forming a cutting edge 24. The second bevel surface 23 faces away from the body surface 16. The delivery part 10 comprises first cavity 58 for accommodating a composition. The first attachment part 18E comprises a hooking zone 72 configured to hook the delivery device to the internal surface, and a cutting zone 74 configured to cut the internal surface for facilitating further penetration of the first attachment part 18E.

FIG. 22

Figure 22:
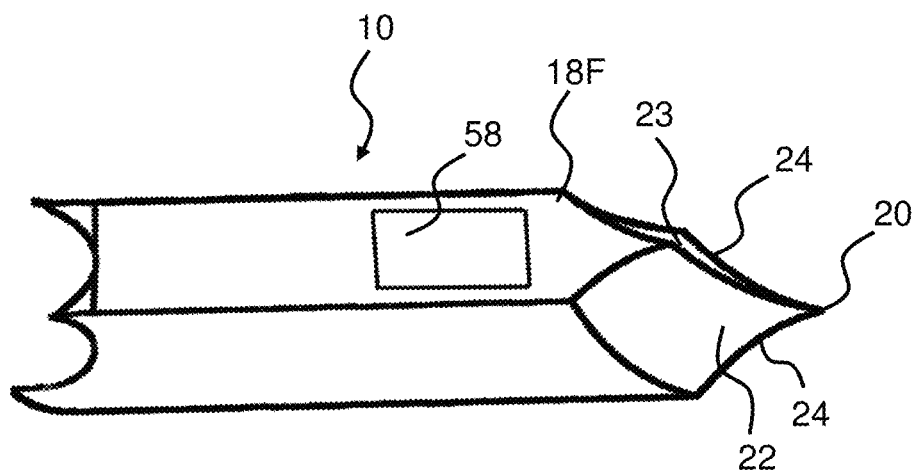
FIG. 22—is a view of an exemplary delivery part/attachment part

FIG. 22 shows a of an exemplary delivery part 10 with first attachment part 18F. The first attachment part 18F has first bevel surface 22 and second bevel surface 23 forming cutting edges 24. The first bevel surface 22 and the second bevel surface 23 are arranged to face away from the body surface of body (not shown). The delivery part 10 comprises first cavity 58 for accommodating a composition.

FIG. 23

Figure 23:
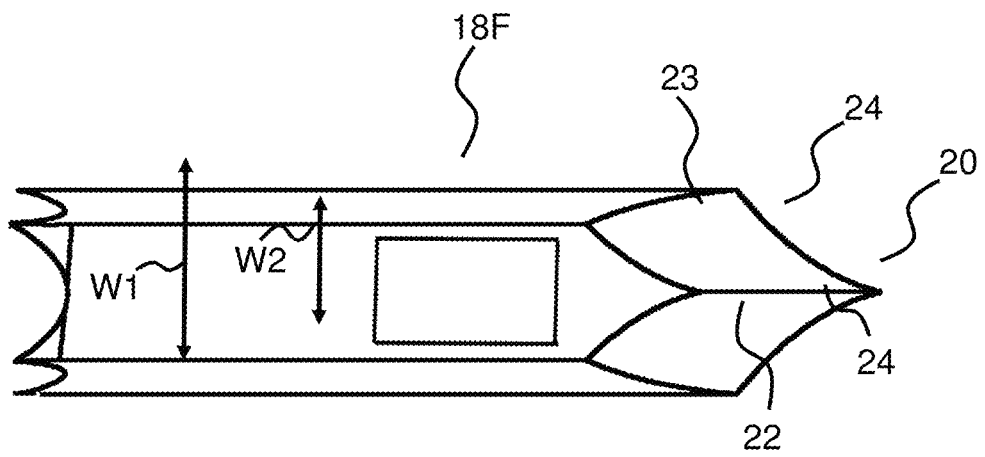
FIG. 23—is a view of an exemplary delivery part/attachment part

FIG. 23 shows a of an exemplary delivery part 10 with first attachment part 18F. The first attachment part 18F has first bevel surface 22 and second bevel surface 23 forming cutting edges 24. The cutting edges 24 extend from the first distal end 20. The first attachment part 18F has a maximum width W1 in the range from 1.0 mm to 2.0 mm and a minimum width W2 in the range from 0.5 mm to 1.5 mm.

FIG. 24

Figure 24:
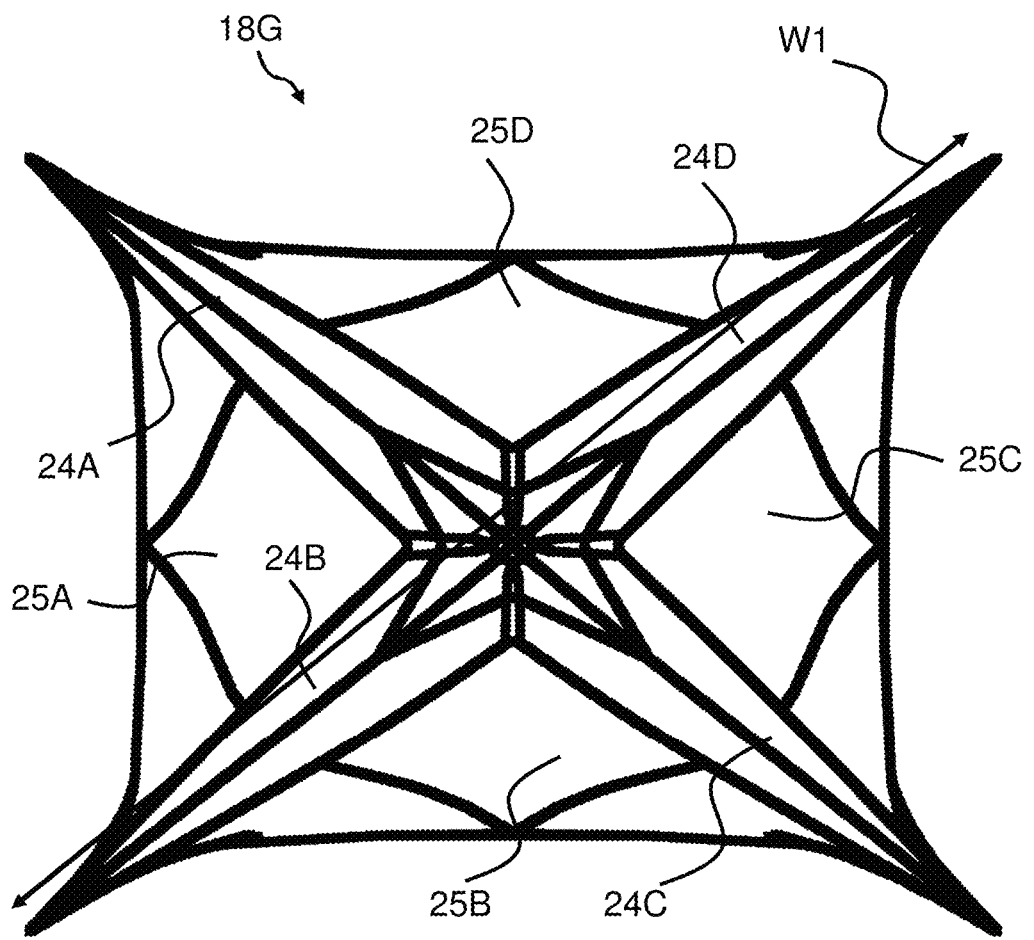
FIG. 24—is a view of an exemplary delivery part/attachment part

FIG. 24 is a distal end view of an exemplary first attachment part 18G. The attachment part 18G has a star-shaped cross-section and comprises four cutting edges 24A, 24B, 24C, 24D defined by four cut-outs 25A, 25B, 25C, 25D. The first attachment part 18G has a maximum width W1 in the range from 1.0 mm to 4 mm, such as about 2.4 mm.

FIG. 25

Figure 25:
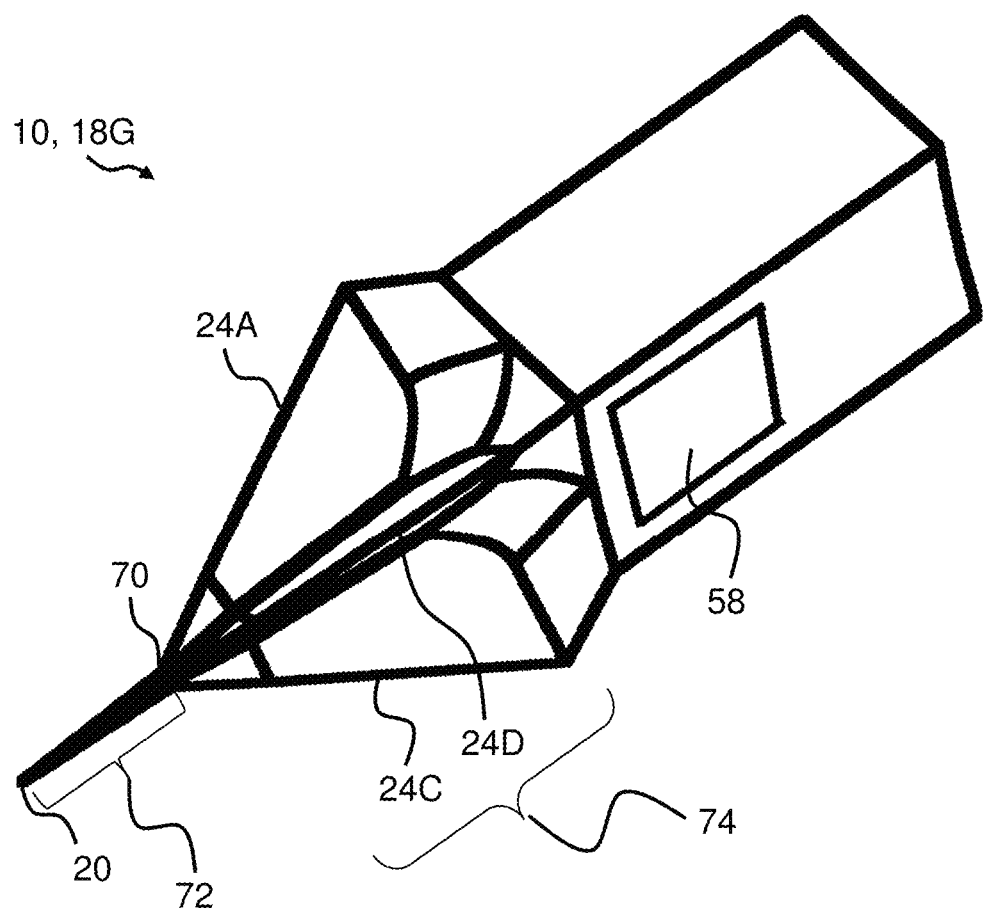
FIG. 25—is a view of an exemplary delivery part/attachment part

FIG. 25 is a view of the first attachment part 18G. The four cutting edges 24A, 24B, 24C, 24D extends from a position 70 within about 1.0 from the distal end 20 to form an initial penetration with the distal end followed by a cutting with the cutting edges when the first attachment part penetrates the internal surface.

EXAMPLES

Example 1—Point Sharpness of the Delivery Part

The below delivery devices (see FIG. 14) according to the disclosure were prepared from the following ingredients:

| Delivery device composition | % (w/w) |
|---|---|
| Polyethylene oxide 200000 | 100 |

| Delivery device composition Batch no. 2669-066 | % (w/w) |
|---|---|
| Hypromellose acetate succinate (AQOAT AS-HG) | 93 |
| Triethyl citrate | 7 |

| Delivery device composition Batch no. 2669-068 | % (w/w) |
|---|---|
| Hypromellose acetate succinate (AQOAT AS-HG) | 90 |
| Triethyl citrate | 10 |

| Delivery device composition Batch no. 17-0020-130 | % (w/w) |
|---|---|
| Poly(methacrylic acid, methyl methacrylate) (Eudragit S100) | 75 |
| Triethyl citrate | 25 |

The delivery device was prepared by load an accurate amount of polymer into a mixer followed by an accurate amount of plasticizer if any. The mixing was performed to secure a homogeneous blend. The blend was fed into an injection molding machine (Krauss Maffei) and molded into the delivery device, the body, connection part and the delivery part in one process.

The delivery part point sharpness may be defined as the first local maximum of the time/force curve related to the penetration of the delivery part point tip (first distal end) though for example a plastic foil. The delivery part point sharpness is measured in gram.

The delivery part point sharpness test was performed using a texture analyzer mounted with a 500 g load cell. The delivery part was cut off the body and mounted on a holder fitted on the load cell. The delivery part penetrates a plastic foil (50 micron LDPE film) with a velocity of 0.03 mm/sec was measured.

| The Point Sharpness of the delivery parts | Average (g) |
|---|---|
| 18G needle Blunt | 103 |
| Prototype (PEO-200.000) | 73 |
| Prototype (2669-066) | 26 |
| Prototype (2669-068) | 20 |
| Prototype (17-0020-130) | 30 |
| 18G needle | 10 |
| 25G needle | 6 |

Example 2—Preparation of a Delivery Device Containing a Payload

The human insulin was gently crushed to smaller particles using a pestle and mortar. Polyethylene glycol 6,000 was added into a glass beaker and heated to approximately 60-80° C. and human insulin was then added and stirred with a spatula until evenly dispersed in the melted polyethylene glycol 6,000. A 25-gauge needle was used to transfer and fill the human insulin dispersed in polyethylene glycol 6,000 into the cavity in the delivery part. Any excess in the cavity was removed by passing the cavity opening past a heated surface to secure even filling of the cavity. The opening to the delivery part cavity containing the payload was sealed with a painted layer of water insoluble nail polish.

The delivery device was prepared as described in example 1.

| Payload Batch No. 130-FDD-2017-07-11 | % (w/w) |
|---|---|
| Human Insulin | 21.2 |
| PEG 6,000 | 78.8 |

| Delivery device composition Batch no. 2669-068 | % (w/w) |
|---|---|
| Hypromellose acetate succinate (AQOAT AS-HG) | 90 |
| Triethyl citrate | 10 |

Example 3—Dissolution

A delivery device (batch No. 2669-068) from example 2 was subjected to the dissolution test described below.

Dissolution test was performed in a 5 mL headspace crimp neck vial, 38×20 mm (Labsolute®). The dissolution medium consisted either of phosphate buffer solution pH 7.4 or of dilute hydrochloric acid 0.1N heated to 37° C. The volume of the dissolution medium was 4.5 ml and rotation speed of the magnet stirrer was in position 5 (analogue hotplate stirrer IKA, model RT 15 P) throughout the dissolution run. Samples were withdrawn after 5, 15, 45, 120 min and analyzed for content of active drug substance by means of HPLC with UV-detector. The results are shown in FIG. 15.

Example 4—Content Uniformity

A delivery device (batch No. 17-0020-130) according to the disclosure was prepared from the following ingredients:

| Delivery device composition Batch no. 17-0020-130 | % (w/w) |
|---|---|
| Poly(methacrylic acid, methyl methacrylate) (Eudragit S100) | 75 |
| Triethyl citrate | 25 |

The delivery device was prepared as described in example 1 and the payload from example 2 was applied.

A 25-gauge needle was used to transfer and fill the payload into the cavity in the delivery part. Any excess in the cavity was removed by passing the cavity opening past a heated surface to secure even filling of the cavity.

|  | Weight, Empty delivery device (mg) | Weight, Delivery device with payload (mg) | Weight, payload (mg) | Human insulin in delivery device (mg) | Human insulin in payload (%) |
|---|---|---|---|---|---|
| Avearage (mg) | 99.473 | 100.886 | 1.412 | 0.303 | 21.6 |
| RSD (%) | 0.1 | 0.4 | 20.4 | 17.8 | 5.9 |

Content Uniformity test was performed by measuring assay and impurity by the following method; Assay and impurity testing samples and standards were diluted in 0.01M HCl. Human Insulin was used as a standard. Both samples and standards were injected onto a UPLC system using a flow rate of 0.3 ml/min and an injection volume of 2 µl, with a Kinetex 1.7 µm C8 100 Å 2.1×50 mm column (30° C.) and a UV detector operated at 214 nm. The mobile phase used was 62% 0.1M $KH_2PO_4$ buffer pH 3.1, 26% CAN and 12% Methanol.

|  | Stability, T = 0 days | | Stability, T = 11 days (5° C.) | | Stability, T = 11 days (25° C./65% RH) | |
|---|---|---|---|---|---|---|
|  | Assay (mg) | Desamido Insulin (mg) | Assay (mg) | Desamido Insulin (mg) | Assay (mg) | Desamido Insulin (mg) |
| Delivery device no. 1 | NA | <LOD | 18.0 | <LOD | 19.9 | <LOD |
| Delivery device no. 2 | NA | <LOD | 17.6 | <LOD | 19.3 | <LOD |
| Delivery device no. 3 | NA | <LOD | 20.2 | <LOD | 19.3 | <LOD |
| Average (n = 3) | 21.6 | <LOD | 18.6 | <LOD | 19.5 | <LOD |
| RSD | NA | | 7.7 | | 1.9 | |

* LOD: 2 µg/mL
NA: Data not available

Example 5—Solubility of AQOAT AS-HG Before and After Injection Molding

The pH dependent solubility of the polymer AQOAT AS-HG (hydroxypropyl methyl cellulose acetate succinate) before and after injection molding is described below. Procedure for characterization of the pH at which pH dependent polymer material dissolves and characterization of the buffer capacity of pH dependent polymer material was investigated.

15 ml saline was added to a 25 ml glass vial and stirred with a magnetic stirrer. pH was adjusted to approximately 7.4 with 0.1N NaOH or 0.1N HCl. The equivalent of 75.0 mg pH dependent polymer was added to the solution either in the form of the pure polymer, as granules or as ground delivery device (granules and ground delivery device applied from example 1). pH in the solution dropped as the pH dependent polymer started to dissolve until it reached the pH at which the pH dependent polymer stopped dissolving. 0.1N NaOH was then added sequentially to the solution while stirring. After each addition of NaOH the pH was measured when the pH stabilized. 0.1N NaOH was added sequentially until all pH dependent polymer was dissolved observed as a sharp increase in the pH. See FIG. 16.

The plasticizer (7% w/w triethyl citrate) had an impact on the pH at which granules of triethyl citrate and polymer AQOAT AS-HG (hydroxypropyl methyl cellulose acetate succinate) started to dissolve in a physiologically relevant medium (saline; 0.9 NaCl w/v %). The pH at which the granules dissolve was independent of subsequent injection molding.

Example 6—Solubility of Eudragit 5100 Before and After Injection Molding

The pH dependent solubility of the polymer Eudragit S100 (Methacrylic Acid and Methyl Methacrylate Copolymer (1:2)) before and after injection molding is described below.

Procedure for characterization of the pH at which pH dependent polymer material dissolves and characterization of the buffer capacity of pH dependent polymer material was investigated.

15 ml saline was added to a 25 ml glass vial and stirred with a magnetic stirrer. pH was adjusted to approximately 7.4 with 0.1N NaOH or 0.1N HCl. The equivalent of 75.0 mg pH dependent polymer was added to the solution either in the form of the pure polymer, as granules or as ground delivery device (granules and ground delivery device applied from example 1). pH in the solution dropped as the pH dependent polymer started to dissolve until it reached the pH at which the pH dependent polymer stopped dissolving. 0.1N NaOH was then added sequentially to the solution while stirring. After each addition of NaOH the pH was measured when the pH stabilized. 0.1N NaOH was added sequentially until all pH dependent polymer was dissolved observed as a sharp increase in the pH. See FIG. 17.

The plasticizer (25% w/w triethyl citrate) had not an impact on the pH at which granules of triethyl citrate add polymer Eudragit S100 (Methacrylic Acid and Methyl Methacrylate Copolymer (1:2)) started to dissolve in a physiologically relevant medium (saline; 0.9 NaCl w/v %). The subsequent injection molding of the granules changed pH at which the injection molded delivery device dissolved.

Example 7—Animal PK Study

The aim of the study was to monitor the blood glucose profiles as a function of a specific composition containing human insulin and delivery part/payload excipients administered in LYH pigs and to investigate blood glucose profiles as a function of site of delivery of the insulin composition i.e. SC injection in the abdominal wall vs injection into the intestinal wall.

Design

Three castrated male LYH pigs, approximately 75 kg body weight, received one composition containing insulin and delivery part/payload excipients that was administered both SC through injection under the skin of the abdominal wall and through injection into the intestinal wall. Each pig also received one placebo composition that was administered SC through injection under the skin of the abdominal wall. That is, each pig received a total of 3 injections. Blood samples were withdrawn and blood glucose measurements were conducted. Dosing of sequence no. 1 and no. 2 was followed by a wash out period.

Investigational Products

Two different compositions were prepared. One composition contained 5 IU insulin and delivery part/payload excipients. The insulin in the composition was derived from the commercial product Actrapid® (Human Insulin 100 IU/mL). The other composition contained only delivery part/payload excipients (placebo). Both compositions were dissolved in saline (0.9% NaCl w/v) and dosed in a volume of 1.0 mL.

The composition of the insulin and delivery part/payload excipients were prepared accordingly:

The delivery part/payload excipients solution was prepared by adding Eudragit S100 to saline (0.9% NaCl w/v) while stirring. The pH was then adjusted to 7.4 with 2M NaOH or 6M HCl until a clear solution was obtained. Triethyl citrate and polyethylene glycol 6,000 were added to the solution while stirring. The solution was additional stirred for 10 minutes. The delivery part/payload excipients solution was then mixed with 0.175 mL Actrapid® (Human Insulin 100 IU/mL) in a vial. The insulin composition is listed below:

| Component | Amount in 1.0 mL |
|---|---|
| Human Insulin | 5.00 IU |
| Eudragit S100 | 5.70 mg |
| Triethyl citrate | 1.43 mg |
| Polyethylene glycol 6,000 | 1.90 mg |

The delivery part/payload excipients composition (placebo) is listed below:

| Component | Amount in 1.0 mL |
|---|---|
| Eudragit S100 | 5.70 mg |
| Triethyl citrate | 1.43 mg |
| Polyethylene glycol 6,000 | 1.90 mg |

Experimental Procedure

On procedure days, the pigs were fasted overnight and in the morning feed was withheld. Tap water was available ad libitum.

Prior to each SC injection the pigs were anesthetized using intramuscular injection of Zoletil-mixture (0.1 mL/kg bw of a solution consisting of 12.5 mg/mL tiletamine, 12.5 mg/mL zolazepam, 12.5 mg/mL xylazine, 12.5 mg/mL ketamine and 2.5 mg/mL butorphanol). Anesthesia was maintained by re-administering the same solution in lower doses. Prior to each Intra-wall injection, the pigs were anesthetized using the zoletil-mixture with added methadone and a local infiltration of Xylocaine was done in the incision site.

A central venous catheter was placed in the jugular vein and used for the blood sampling procedures. After each of the blood sampling sessions in study sequence no. 1-2 the pigs were carefully observed and returned to normal conscious state. The wash out period was at least 48 hours.

A Luer-lock syringe with a 21 G needle was used for SC injection of the abdominal wall and a Luer-lock syringe with a 25 G needle for the injection into the intestinal wall.

SC injection of the abdominal wall was performed in the groin area.

Injection of jejunal mucosa was performed surgically by performing a laparotomy in the cranial abdominal midline using scalpel and scissors. The procedure was carried out under aseptic conditions. The jejunum was localized by following the intestine in aboral direction from the stomach until the end of the duodenum. The injection site was approximately 100 cm down the length of the jejunum, measured from the transition between the duodenum and the jejunum. At this site, and incision of approx. 3 cm (longitudinal) was made in the antimesenteric intestinal wall. The mucosal lining was accessed through the incision and the test substance was injected in the mucosa at least 2 cm from the incision to avoid any leaking of the test substance.

If hypoglycemia was observed (blood glucose concentration below 2.0 mmol/L), the blood glucose was corrected using intravenous bolus of glucose.

Blood samples were collected through the central venous catheter. Prior to every sampling the first 0.5-2 mL of blood drawn from the catheter was discarded. After each sampling the catheter was flushed with heparinized saline (10 IU/ml) to avoid clotting. Blood glucose was determined from the in-life blood samples immediately after withdrawal of the blood samples using a Bayer Contour XT glucose meter.

Results

Pig #1 and Pig #2 received all treatment sequences. Pig #3 did not receive all treatment sequences due to hypoglycemia on dosing day. No clinical signs were observed in any of the pigs during the study period.

The mean blood glucose values for each composition and route of administration for the two pigs is shown in FIG. 18.

Example 8—Point Sharpness of the Delivery Part

The below delivery devices (see FIG. 14 and FIGS. 19-21) according to the disclosure were prepared from the following ingredients:

| Delivery device composition | % (w/w) |
|---|---|
| Ultramid A3 EG10 | 100 |

The delivery device was prepared by load an accurate amount of polymer into a mixer followed by an accurate amount of plasticizer if any. The mixing was performed to secure a homogeneous blend. The blend was fed into an injection molding machine (Krauss Maffei) and molded into the delivery device, the body, connection part and the delivery part in one process.

Three different silicone solutions were tested to see if siliconation would lower the resistance to penetration of the delivery part and thereby lowering the point sharpness value.

The delivery part point sharpness may be defined as the first local maximum of the time/force curve related to the penetration of the delivery part point tip (first distal end) though for example a plastic foil. The delivery part point sharpness is measured in gram.

The delivery part point sharpness test was performed using a texture analyzer mounted with a 500 g loadcell. The delivery part was cut off the body and mounted on a holder fitted on the load cell. The delivery part penetrates a plastic foil (80 micron PU film) with a velocity of 0.1 mm/sec was measured.

| The Point Sharpness of the delivery parts | Average (g) |
|---|---|
| 18G needle Blunt | 146 |
| Prototype 1 (FIG. 14) Clean | 59 |
| Prototype 2 (FIG. 19-21) Clean | 139 |
| Prototype 2 (FIG. 19-21) coated with 360 Medical Fluid 12500 CST | 124 |
| Prototype 2 (FIG. 19-21) Coated with 5% (v/v) DC MDX4-4159 Fluid and cured 1 day at 70° C. | 115 |
| Prototype 2 (FIG. 19-21) Coated with 5% (v/v) DC MDX4-4159 Fluid and cured 1 day at 70° C. | 87 |
| Prototype 2 (FIG. 19-21) coated with 360 Medical Fluid 1000 CST | 74 |
| 18G needle | 30 |

LIST OF REFERENCES 2, 2A, 2B, 2C, 2D, 2E, 2F delivery device
4 first end
6 second end
8 body
10 delivery part
12 first body end
14 second body end
16 body surface
18, 18A, 18B, 18C, 18D, 18E, 18F, 18G first attachment part
20 first distal end
22 first bevel surface
23 second bevel surface
24, 24A, 24B, 24C, 24D cutting edge
25, 25A, 25B, 25C, 25D cut-outs
26 first bevel normal
30 connection part
50 composition
52 carrier
54 gastrointestinal wall
56 gastrointestinal cavity
58 first cavity
60 first opening in first attachment part
62 outer surface of first attachment part
64 separation part
66 first barb element
68 first bend
70 position where the cutting edges extend from
72 hooking zone
74 cutting zone
X_L longitudinal axis
X_B body axis
X_C connection axis
X1 first axis
X2 second axis
X1_D first direction
L1 length of first attachment part
D1 distance between the first distal end and the body surface
V1 first angle between first axis and longitudinal axis
VB1_1 first primary bevel angle
VB1_2 first secondary bevel angle
VC1 first connection angle
VC2 second connection angle
W1, W2 width Items 1. A delivery device for a composition, the delivery device having a first end and a second end with a longitudinal axis there between, and comprising a body and a delivery part, the body extending along a body axis from a first body end and having a body surface, the delivery part comprising a first attachment part, the first attachment part having a first distal end configured to position itself in an internal surface of a subject, wherein the first attachment part extends along a first axis, wherein a first angle between the first axis and the longitudinal axis is less than 75 degrees.

2. Delivery device according to item 1, the first distal end being arranged at a distance from the body surface, wherein the distance is at least 0.5 mm.

3. Delivery device according to any of items 1-2, wherein the first attachment part has a length in the range from 1.0 mm to 20 mm.

4. Delivery device according to any of items 1-3, wherein the first attachment part comprises a first bevel surface forming a cutting edge extending from the first distal end.

5. Delivery device according to item 4, wherein the first bevel surface is concave.

6. Delivery device according to any of items 4-5, wherein the first bevel surface has a first bevel normal, the first bevel normal forming a first primary bevel angle with the first axis larger than 20 degrees.

7. Delivery device according to any of items 4-6, wherein the first bevel surface has a first bevel normal, the first bevel normal forming a first secondary angle with the longitudinal axis larger than 45 degrees.

8. Delivery device according to any of items 1-7, wherein the first attachment part comprises a second bevel surface forming a cutting edge at the first distal end.

9. Delivery device according to item 8, wherein the second bevel surface is concave.

10. Delivery device according to any of items 1-9, wherein the first attachment part defines a first cavity for accommodating a payload comprising an active drug substance.

11. Delivery device according to any of items 1-10, the delivery part comprising a second attachment part, the second attachment part having a second distal end configured to position itself in an internal surface of a subject, the second distal end being arranged at a distance from the body surface, wherein the distance is at least 0.5 mm.

12. Delivery device according to any of items 1-11, wherein the first distal end of the first attachment part is arranged between the first body end and a second body end of the body.

13. Delivery device according to any of items 1-12, wherein the body is made of a material comprising one or more thermoplastic polymers.

14. Delivery device according to any of items 1-13, wherein the delivery part is made of a material comprising one or more thermoplastic polymers.

15. Delivery device according to item 14, wherein the material of the first attachment part comprises one or more active drug substances.

16. Delivery device according to any of items 1-15, wherein the delivery device comprises a separation part arranged between the body and the first attachment part, wherein the separation part is configured to break upon attachment of the first attachment part to the internal surface for separating the body and the first attachment part upon attachment of the first attachment part.

17. Delivery device according to any of items 1-16, wherein the body has a droplet shape with a wide end towards the first body end.

18. A composition comprising a carrier and a delivery device according to any of items 1-17.

19. A composition according to item 18, wherein the composition is an oral composition.

20. A composition according to any of items 18-19, wherein the composition is a pharmaceutical composition comprising an active drug substance.

21. A composition according to item 20, wherein the composition comprises a payload with the active drug substance, wherein the payload is accommodated in a cavity of the delivery device.

The invention claimed is:

1. A delivery device for a composition, the delivery device comprising a body and a delivery part, the body extending along a body axis from a first body end to a second body end and having a body surface, the delivery part comprising a first attachment part, the first attachment part having a first distal end, wherein the first attachment part comprises a first bend and extends along a first axis, wherein a first angle between the first axis and the body axis is less than 75 degrees.

2. The delivery device according to claim 1, wherein the first distal end is configured to position itself in an internal surface of a subject.

3. The delivery device according to claim 1, wherein the first attachment part has a length in the range from 1.0 mm to 20 mm.

4. The delivery device according to claim 1, the first distal end being arranged at a distance from the body surface, wherein the distance is at least 0.5 mm.

5. The delivery device according to claim 1, wherein the first attachment part comprises a first bevel surface forming a cutting edge extending from the first distal end.

6. The delivery device according to claim 5, wherein the first bevel surface faces the body surface.

7. The delivery device according to claim 1, wherein the first attachment part defines a first cavity for accommodating a payload comprising an active drug substance.

8. The delivery device according to claim 1, the delivery part comprising a second attachment part, the second attachment part having a second distal end configured to position itself in an internal surface of a subject.

9. The delivery device according to claim 1, wherein the first distal end of the first attachment part is arranged between the first body end and the second body end.

10. The delivery device according to claim 1, wherein the body is made of a material comprising one or more thermoplastic polymers.

11. The delivery device according to claim 1, wherein the delivery part is made of a material comprising one or more thermoplastic polymers.

12. The delivery device according to claim 1, wherein the material of the first attachment part comprises one or more active drug substances.

13. The delivery device according to claim 1, wherein the delivery device comprises a separation part arranged between the body and the first attachment part, wherein the separation part is configured to break upon attachment of the first attachment part to internal tissue for separating the body and the first attachment part upon attachment of the first attachment part.

14. A delivery device for a composition, the delivery device comprising a body and a delivery part, the body extending along a body axis from a first body end to a second body end and having a body surface, the delivery part comprising a first attachment part, the first attachment part having a first distal end configured to position itself in an internal surface of a subject, wherein the first attachment part comprises a first bend and has a length in the range from 1.0 mm to 20 mm.

15. The delivery device according to claim 14, the first distal end being arranged at a distance from the body surface, wherein the distance is at least 0.5 mm.

16. The delivery device according to claim 14, wherein the first attachment part defines a first cavity for accommodating a payload comprising an active drug substance.

17. The delivery device according to claim 14, wherein the first distal end of the first attachment part is arranged between the first body end and the second body end.

18. A delivery device for a composition, the delivery device comprising a body and a delivery part, the body extending along a body axis from a first body end to a second body end and having a body surface, the delivery part being curved and comprising a first attachment part, the first attachment part having a first distal end configured to position itself in an internal surface of a subject.

19. The delivery device according to claim 18, wherein the first distal end of the first attachment part is arranged between the first body end and the second body end.

20. The delivery device according to claim 18, wherein the first attachment part defines a first cavity for accommodating a payload comprising an active drug substance.

* * * * *